US009649371B2

(12) United States Patent
He

(10) Patent No.: US 9,649,371 B2
(45) Date of Patent: May 16, 2017

(54) RECOMBINANT MUMPS VIRUS VACCINE

(75) Inventor: Biao He, Bogart, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 14/001,228

(22) PCT Filed: Feb. 24, 2012

(86) PCT No.: PCT/US2012/026436
§ 371 (c)(1),
(2), (4) Date: Sep. 25, 2013

(87) PCT Pub. No.: WO2012/116253
PCT Pub. Date: Aug. 30, 2012

(65) Prior Publication Data
US 2014/0010840 A1    Jan. 9, 2014

Related U.S. Application Data

(60) Provisional application No. 61/446,619, filed on Feb. 25, 2011, provisional application No. 61/529,981, filed on Sep. 1, 2011.

(51) Int. Cl.
| | | |
|---|---|---|
| *A61K 39/165* | (2006.01) | |
| *A61K 39/12* | (2006.01) | |
| *A61K 39/155* | (2006.01) | |
| *C12N 7/00* | (2006.01) | |
| *C07K 16/10* | (2006.01) | |
| *C07K 16/24* | (2006.01) | |
| *A61K 39/00* | (2006.01) | |

(52) U.S. Cl.
CPC ............ *A61K 39/165* (2013.01); *A61K 39/12* (2013.01); *A61K 39/155* (2013.01); *C07K 16/1027* (2013.01); *C07K 16/241* (2013.01); *C12N 7/00* (2013.01); *A61K 2039/5254* (2013.01); *A61K 2039/5256* (2013.01); *A61K 2039/543* (2013.01); *C07K 2317/34* (2013.01); *C12N 2760/18534* (2013.01); *C12N 2760/18721* (2013.01); *C12N 2760/18734* (2013.01); *C12N 2760/18743* (2013.01); *C12N 2760/18762* (2013.01)

(58) Field of Classification Search
None
See application file for complete search history.

(56) References Cited

U.S. PATENT DOCUMENTS

| | | |
|---|---|---|
| 5,783,194 A | 7/1998 | Brown et al. |
| 7,361,496 B1 | 4/2008 | Clarke et al. |
| 2007/0253972 A1 | 11/2007 | Clarke et al. |
| 2013/0078281 A1 | 3/2013 | He et al. |
| 2014/0370050 A1 | 12/2014 | He et al. |
| 2015/0086588 A1 | 3/2015 | He et al. |

FOREIGN PATENT DOCUMENTS

| | | |
|---|---|---|
| EP | 2 123 755 A1 | 11/2009 |
| WO | WO 01/09309 A2 | 2/2001 |
| WO | WO 2008/096811 A1 | 8/2008 |
| WO | WO 2011/150320 A2 | 12/2011 |
| WO | WO 2011/150320 A3 | 5/2012 |
| WO | WO 2013/112690 A1 | 8/2013 |
| WO | WO 2013/112720 A1 | 8/2013 |

OTHER PUBLICATIONS

Takeuchi et al. The Mumps Virus SH Protein Is a Membrane Protein and Not Essential for Virus Growth. Virology 225, 156-162 (1996).*
Clarke et al. Rescue of Mumps Virus from cDNA. Journal of Virology, 2000, 74:4831-4838.*
Boddicker et al. Real-Time Reverse Transcription-PCR Assay for Detection of Mumps Virus RNA in Clinical Specimens. Journal of Clinical Microbiology, Sep. 2007, p. 2902-2908 vol. 45.*
GenBank: DQ661745.1. Mumps virus strain MUM/Iowa.US/2006 small hydrophobic protein mRNA, complete cds. http://www.ncbi.nlm.nih.gov/nuccore/DQ661745. Sep. 5, 2007.*
Wilson et al. Function of small hydrophobic proteins of paramyxovirus. J Virol. Feb. 2006;80(4):1700-9.*
GenBank: GU980052.1. Mumps virus strain Enders, complete genome. Apr. 25, 2010. http://www.ncbi.nlm.nih.gov/nuccore/GU980052.1.*
GenBank: JN012242.1. Mumps virus strain MuV-IA, complete genome. Feb. 3, 2012 http://www.ncbi.nlm.nih.gov/nuccore/JN012242.1.*
Xu et al. Prime-boost vaccination with recombinant mumps virus and recombinant vesicular stomatitis virus vectors elicits an enhanced human immunodeficiency virus type 1 Gag-specific cellular immune response in rhesus macaques. J Virol. Oct. 2009;83(19):9813-23. Epub Jul. 22, 2009.*
Schaap-Nutt et al. Human parainfluenza virus type 2 V protein inhibits interferon production and signaling and is required for replication in non-human primates. Virology 397 (2010) 285-298. Available online Dec. 7, 2009.*
Delenda et al. Normal Cellular Replication of Sendai Virus without the trans-Frame, Nonstructural V Protein. Virology 228, 55-62 (1997).*
Afzal et al., Evaluation of the neurovirulence test for mumps vaccines, Mar. 1999, *Biologicals* 27(1):43-49.
Amexis et al., Sequence diversity of Jeryl Lynn strain of mumps virus: quantitative mutant analysis for vaccine quality control, Sep. 2002, *Virology* 300(2):171-179.
Andrejeva et al., The V proteins of paramyxoviruses bind the IFN-inducible RNA helicase, mda-5, and inhibit its activation of the IFN-βpromoter, Dec. 2004, *Proc. Nat'l Acad. Sci. U.S.A.* 101(49):17264-17269.
Atrasheuskaya et al., Investigation of mumps vaccine failures in Minsk, Belarus, 2001-2003, Jun. 2007, *Vaccine* 25(24):4651-4658.

(Continued)

*Primary Examiner* — Nick Zou
(74) *Attorney, Agent, or Firm* — Mueting, Raasch & Gebhardt, P.A.

(57) ABSTRACT

The present invention provides the complete genomic sequence of the epidemic mumps virus (MuV) strain MuV$^{Iowa/us/06}$. Further, a reverse genetics system was constructed and used to rescue recombinant viral constructs that are attenuated compared to MuV$^{Iowa/us/06}$ and JL vaccine viruses. Such constructs include viral constructs lacking the open reading frame (ORF) of the SH gene (rMuVΔSH) and/or incapable of expressing the V protein (rMuVΔV).

24 Claims, 27 Drawing Sheets

(56) References Cited

OTHER PUBLICATIONS

Atrasheuskaya et al., Mumps vaccine failure investigation in Novosibirsk, Russia, 2002-2004, Jul. 2007, *Clin. Microbiol. Infect.* 13(7):670-676.
Ausubel et al. (eds.), *Current Protocols in Molecular Biology*, vols. 1-4, John Wiley & Sons, Inc., New York, NY, 1994-2001; title page, publisher's page and table of contents only (26 pages).
Baud et al., Signal transduction by tumor necrosis factor and its relatives, Sep. 2001, *Trends Cell Bio.* 11(9):372-377.
Bitsko et al., Detection of RNA of mumps virus during an outbreak in a population with a high level of measles, mumps, and rubella vaccine coverage, Mar. 2008, *J. Clin. Microbiol.* 46(3):1101-1103.
Carbone et al., "Mumps Virus," in *Fields Virology*. Knipe et al. (eds.) Lippincott, Williams, and Wilkins: Philadelphia, PA; 2001. Cover page, publisher's page, and pp. 1381-1400.
Centers for Disease Control and Prevention, Mumps epidemic—United Kingdom, 2004-2005, Feb. 24, 2006, *Morb. Mortal. Wkly Rep.* 55(7):173-175.
Centers for Disease Control and Prevention, Update: mumps outbreak—New York and New Jersey, Jun. 2009-Jan. 2010, Feb. 12, 2010, *Morb. Mortal. Wkly Rep.* 59(5):125-129.
Clarke et al., Rescue of mumps virus from cDNA, May 2000, *J. Virol.* 74(10):4831-4838.
Collins et al., "Respiratory syncytial virus," in *Fields Virology*. Knipe et al. (eds.) Lippincott, Williams, and Wilkins: Philadelphia, PA; 2001. Cover page, publisher's page, and pp. 1443-1485.
Colville et al., Withdrawal of a mumps vaccine, Jun. 1994, *Eur. J. Pediatr.* 153(6):467-468.
Cortese et al., Mumps vaccine performance among university students during a mumps outbreak, Apr. 2008, *Clin. Infect. Dis.* 46(18):1172-1180.
Cui et al., Analysis of the genetic variability of the mumps SH gene in viruses circulating in the UK between 1996 and 2005, Jan. 2009, *Infect. Genet. Evol.* 9(1):71-80.
Cusi et al., Nucleotide sequence at position 1081 of the hemagglutinin-neuraminidase gene in wild-type strains of mumps virus is the most relevant marker of virulence, Dec. 1998, *J. Clin. Microbiol.* 36(12):3743-3744.
Cusi et al., Comparative study of the immune response in mice immunized with four live attenuated strains of mumps virus by intranasal or intramuscular route, Jul. 2001, *Arch. Virol.* 146(7):1241-1248.
Date et al., Long-term persistence of mumps antibody after receipt of 2 measles-mumps-rubella (MMR) vaccinations and antibody response after a third MMR vaccination among a university population, Jun. 2008, *J. Infect. Dis.*197(12):1662-1668.
Dayan et al., Mumps outbreaks in vaccinated populations: are available mumps vaccines effective enough to prevent outbreaks?, Dec. 2008, *Clin. Infect. Dis.* 47(11):1458-1467.
Dillon et al., Role for the phosphoprotein P subunit of the paramyxovirus polymerase in limiting induction of host cell antiviral responses, Oct. 2007, *J. Virol.* 81(20):11116-11127.
Dourado et al., Outbreak of aseptic meningitis associated with mass vaccination with a Urabe-containing measles-mumps-rubella vaccine: implications for immunization programs, Mar. 2000, *Am. J. Epidemiol.* 151(5):524-530.
Elango et al., Molecular cloning and characterization of six genes, determination of gene order and intergenic sequences and leader sequence of mumps virus, Nov. 1988, *J. Gen. Virol.* 69:2893-2900.
Enders et al., Immunity in mumps: I. Experiments with monkeys (*Macacus mulatta*). The development of complement-fixing antibody following infection and experiments on immunization by means of inactivated virus and convalescent human serum, Jan. 1945, *J. Exp. Med.* 81(1):93-117.
Enders, Mumps: Techniques of laboratory diagnosis, tests for susceptibility, and experiments on specific prophylaxis, Aug. 1946, *J. Pediatr.* 29(2):129-142.
Foy et al., Isolation of mumps virus from children with acute lower respiratory tract disease, Nov. 1971, *Am. J. Epidemiol.* 94(5):467-472.
Fulginiti et al., Altered reactivity to measles virus. Atypical measles in children previously immunized with inactivated measles virus vaccines, Dec. 1967, *JAMA* 202(12):1075-1080.
Fulginiti et al., Respiratory virus immunization. I. A field trial of two inactivated respiratory virus vaccines; an aqueous trivalent parainfluenza virus vaccine and an alum-precipitated respiratory syncytial virus vaccine, Apr. 1969, *Am. J. Epidemiol.* 89(4):435-448.
Gordon et al., Response of ferrets to mumps virus, Apr. 1956, *J. Immunol.* 76(4):328-333.
He, Biao, "Pathogenesis of Mumps Virus," Grant Abstract, Grant No. 065795 [online]. National Institute of Allergy and Infectious Diseases; National Institutes of Health. Project dates Jun. 15, 2006 to Apr. 30, 2012 [retrieved on Jul. 16, 2014]. Retrieved from the Internet: <http://projectreporter.nih.gov/pr_Prj_info_desc_dtls.cfm?aid=7825421&icde=21056951&ddparam=&ddvalue=&ddsub=&cr=1&csb=default&cs=ASC&print=yes>; 2 pgs.
He et al., Phage RNA polymerase vectors that allow efficient gene expression in both prokaryotic and eukaryotic cells, Oct. 1995, *Gene* 164(1):75-79.
He et al., A mutant T7 RNA polymerase that is defective in RNA binding and blocked in the early stages of transcription, Jan. 1997, *J. Mol. Biol.* 265(3):275-288.
He et al., Rapid mutagenesis and purification of phage RNA polymerases, Feb. 1997, *Protein Exp. Purif.* 9(1):142-151.
He et al., Recovery of infectious SV5 from cloned DNA and expression of a foreign gene, Oct. 1997, *Virology* 237(2):249-260.
He et al., The paramyxovirus SV5 small hydrophobic (SH) protein is not essential for virus growth in tissue culture cells, Oct. 1998, *Virology* 250(1):30-40.
He et al., Effect of inserting paramyxovirus simian virus 5 gene junctions at the HN/L gene junction: analysis of accumulation of mRNAs transcribed from rescued viable viruses, Aug. 1999, *J. Virol.* 73(8):6228-6234.
He et al., The SH integral membrane protein of the paramyxovirus simian virus 5 is required to block apoptosis in MDBK cells, May 2001, *J. Virol.* 75(9):4068-4079.
He et al., Recovery of paramyxovirus simian virus 5 with a V protein lacking the conserved cysteine-rich domain: the multifunctional V protein blocks both interferon-β induction and interferon signaling, Nov. 2002, *Virology* 303(1):15-32.
Henle et al., Isolation of mumps virus from human beings with induced apparent or inapparent infections, Aug. 1948, *J. Exp. Med.* 88(2):223-232.
Hiebert et al., Identification and predicted sequence of a previously unrecognized small hydrophobic protein, SH, of the paramyxovirus simian virus 5, Sep. 1985, *J. Virol.* 55(3):744-751.
Hiebert et al., Cell surface expression and orientation in membranes of the 44-amino-acid SH protein of simian virus Jul. 5, 1988, *J. Virol.* 62(7):2347-2357.
Hilleman, Past, present, and future of measles, mumps, and rubella virus vaccines, Jul. 1992, *Pediatrics* 90(1):149-153.
Ilonen et al., Lymphocyte blast transformation and antibody responses after vaccination with inactivated mumps virus vaccine, Oct. 1981, *Acta Pathol. Microbiol. Scand. C* 89(5):303-309.
Iwaski et al., Toll-like receptor control of the adaptive immune responses, Oct. 2004, *Nat. Immunol.* 5(10):987-995.
Jin et al., Proposal for genetic characterisation of wild-type mumps strains: preliminary standardisation of the nomenclature, Sep. 2005,*Arch. Virol.* 150(9):1903-1909.
Julkunen et al., Antibody responses to mumps virus proteins in natural mumps infection and after vaccination with live and inactivated mumps virus vaccines, 1984, *J. Med. Virol.* 14(3):209-219.
Kapikian et al., An epidemiologic study of altered clinical reactivity to respiratory syncytial (RS) virus infection in children previously vaccinated with an inactivated RS virus vaccine, Apr. 1969, *Am. J. Epidemiol.* 89(4):405-421.
Kilham et al., Nonparalytic poliomyelitis and mumps meningoencephalitis: differential diagnosis, Jul. 1949, *JAMA* 140(9):934-936.
Kim et al., Respiratory syncytial virus disease in infants despite prior administration of antigenic inactivated vaccine, Apr. 1969, *Am. J. Epidemiol.* 89(4):422-434.

(56) References Cited

OTHER PUBLICATIONS

Kolakofsky et al., Paramyxovirus RNA synthesis and the requirement for hexamer genome length: the rule of six revisited, Feb. 1998, *J. Virol.* 72(2):891-899.
Krempl et al., Recombinant respiratory syncytial virus with the G and F genes shifted to the promoter-proximal positions, Dec. 2002, *J. Virol.* 76(23):11931-11942.
Kubota et al., C terminal CYS-RICH region of mumps virus structural V protein correlates with block of interferon α and γ signal transduction pathway through decrease of STAT 1-α, Apr. 2001, *Biochem. Biophys. Res. Commun.* 283(1):255-259.
Kubota et al., Association of mumps virus V protein with RACK1 results in dissociation of STAT-1 from the alpha interferon receptor complex, Dec. 2002, *J. Virol.* 76(24):12676-12682.
Kubota et al., Mumps virus V protein antagonizes interferon without the complete degradation of STAT1, Apr. 2005, *J. Virol.* 79(7):4451-4459.
LeBaron et al., Persistence of rubella antibodies after 2 doses of measles-mumps-rubella vaccine, Sep. 15, 2009, *J. Infect. Dis.* 200(6):888-899 (published online Aug. 6, 2009).
Li et al., *Beilong virus*, a novel paramyxovirus with the largest genome of non-segmented negative-stranded RNA viruses, Mar. 2006, *Virology* 346(1):219-228.
Li et al., Function of the small hydrophobic protein of J paramyxovirus, Jan. 2011, *J. Virol.* 85(1):32-42 (published online Oct. 27, 2010).
Lim et al., Hemagglutinin-neuraminidase sequence and phylogenetic analyses of mumps virus isolates from a vaccinated population in Singapore, Jun. 2003, *J. Med. Virol.* 70(2):287-292.
Lin et al., Induction of apoptosis by paramyxovirus simian virus 5 lacking a small hydrophobic gene, Mar. 2003, *J. Virol.* 77(6):3371-3383.
Lin et al., The role of simian virus 5 V protein on viral RNA synthesis, Aug. 2005, *Virology* 338(2):270-280.
Lin et al., Inhibition of interleukin-6 expression by the V protein of parainfluenza virus 5, Nov. 2007, *Virology* 368(2):262-272.
Lu et al., Select paramyxoviral V proteins inhibit IRF3 activation by acting as alternative substrates for inhibitor of κB kinase ε (IKKe)/TBK1, May 2008, *J. Biol. Chem.* 283(21):14269-14276.
Luthra et al., AKT1-dependent activation of NF-κB by the L protein of parainfluenza virus 5, Nov. 2008, *J. Virol.* 82(21):10887-10895.
Luthra et al., Activation of IFN-β expression by a viral mRNA through RNase L and MDA5, Feb. 1, 2011, *Proc. Nat'l Acad. Sci. U.S.A.* 108(5):2118-2123 (published online Jan. 18, 2011).
Marin et al., Mumps vaccination coverage and vaccine effectiveness in a large outbreak among college students—Iowa, 2006, Jul. 2008, *Vaccine* 26(29-30):3601-3607.
Matsumoto, Assembly of paramyxoviruses, Apr. 1982, *Microbiol. Immunol.* 26(4):285-320.
Nader et al., Reported neurologic disorders following live measles vaccine, May 1968, *Pediatrics* 41(5):997-1001.
National Center for Biotechnology Information, National Library of Medicine, National Institutes of Health, GenBank Locus AF280799, Accession No. AF280799, "Mumps virus strain Gloucl/UK96, complete genome," [online]. Bethesda, MD [retrieved on Jul. 1, 2014]. Retrieved from the Internet: <URL: http://www.ncbi.nlm.nih.gov/nuccore/AF280799>; 6 pgs.
National Center for Biotechnology Information, National Library of Medicine, National Institutes of Health, GenBank Locus AF314560, Accession No. AF314560, "Mumps virus isolate 87 1004, complete genome," [online]. Bethesda, MD [retrieved on Jul. 1, 2014]. Retrieved from the Internet: <URL: http://www.ncbi.nlm.nih.gov/nuccore/AF314560>; 6 pgs.
National Center for Biotechnology Information, National Library of Medicine, National Institutes of Health, GenBank Locus AF314558, Accession No. AF314558, "Mumps virus strain SIPAR 02, complete genome," [online]. Bethesda, MD [retrieved on Jul. 1, 2014]. Retrieved from the Internet: <URL: http://www.ncbi.nlm.nih.gov/nuccore/AF314558>; 6 pgs.
National Center for Biotechnology Information, National Library of Medicine, National Institutes of Health, GenBank Locus AF314561, Accession No. AF314561, "Mumps virus strain Biken, complete genome," [online]. Bethesda, MD [retrieved on Jul. 1, 2014]. Retrieved from the Internet: <URL: http://www.ncbi.nlm.nih.gov/nuccore/AF314561>; 6 pgs.
National Center for Biotechnology Information, National Library of Medicine, National Institutes of Health, GenBank Locus AF314562, Accession No. AF314562, "Mumps virus isolate 87 1005, complete genome," [online]. Bethesda, MD [retrieved on Jul. 1, 2014]. Retrieved from the Internet: <URL: http://www.ncbi.nlm.nih.gov/nuccore/AF314562>; 6 pgs.
National Center for Biotechnology Information, National Library of Medicine, National Institutes of Health, GenBank Locus AF314559, Accession No. AF314559, "Mumps virus, complete genome," [online]. Bethesda, MD [retrieved on Jul. 1, 2014]. Retrieved from the Internet: <URL: http://www.ncbi.nlm.nih.gov/nuccore/AF314559>; 6 pgs.
National Center for Biotechnology Information, National Library of Medicine, National Institutes of Health, GenBank Locus FJ375177, Accession No. FJ375177, "Mumps virus isolate 1004-10/2, complete genome," [online]. Bethesda, MD [retrieved on Jul. 1, 2014]. Retrieved from the Internet: <URL: http://www.ncbi.nlm.nih.gov/nuccore/FJ375177>; 6 pgs.
National Center for Biotechnology Information, National Library of Medicine, National Institutes of Health, GenBank Locus FJ375178, Accession No. FJ375178, "Mumps virus isolate Gw7, complete genome," [online]. Bethesda, MD [retrieved on Jul. 1, 2014]. Retrieved from the Internet: <URL: http://www.ncbi.nlm.nih.gov/nuccore/FJ375178>; 6 pgs.
National Center for Biotechnology Information, National Library of Medicine, National Institutes of Health, GenBank Locus AB470486, Accession No. AB470486, "Mumps virus genomic RNA, complete genome, Hoshino vaccine strain," [online]. Bethesda, MD [retrieved on Jul. 1, 2014]. Retrieved from the Internet: <URL: http://www.ncbi.nlm.nih.gov/nuccore/AB470486>; 6 pgs.
National Center for Biotechnology Information, National Library of Medicine, National Institutes of Health, GenBank Locus NC_002200, Accession No. NC_002200, "Mumps virus, complete genome," [online]. Bethesda, MD [retrieved on Jul. 1, 2014]. Retrieved from the Internet: <URL: http://www.ncbi.nlm.nih.gov/nuccore/NC_002200>; 7 pgs.
National Center for Biotechnology Information, National Library of Medicine, National Institutes of Health, GenBank Locus AB040874, Accession No. AB040874, "Mumps virus genomic RNA, complete genome," [online]. Bethesda, MD [retrieved on Jul. 1, 2014]. Retrieved from the Internet: <URL: http://www.ncbi.nlm.nih.gov/nuccore/AB040874>; 6 pgs.
National Center for Biotechnology Information, National Library of Medicine, National Institutes of Health, GenBank Locus AB576764, Accession No. AB576764, "Mumps virus cRNA, complete genome, strain: Y213," [online]. Bethesda, MD [retrieved on Jul. 1, 2014]. Retrieved from the Internet: <URL: http://www.ncbi.nlm.nih.gov/nuccore/AB576764>; 7 pgs.
National Center for Biotechnology Information, National Library of Medicine, National Institutes of Health, GenBank Locus AY309060, Accession No. AY309060, "Mumps virus isolate Dg1062/Korea/98, complete genome," [online]. Bethesda, MD [retrieved on Jul. 1, 2014]. Retrieved from the Internet: <URL: http://www.ncbi.nlm.nih.gov/nuccore/32172464>; 6 pgs.
National Center for Biotechnology Information, National Library of Medicine, National Institutes of Health, GenBank Locus AY508995, Accession No. AY508995, "Mumps virus strain L3/Russia/Vector, complete genome," [online]. Bethesda, MD [retrieved on Jul. 1, 2014]. Retrieved from the Internet: <URL: http://www.ncbi.nlm.nih.gov/nuccore/AY508995>; 6 pgs.
National Center for Biotechnology Information, National Library of Medicine, National Institutes of Health, GenBank Locus AY685921, Accession No. AY685921, "Mumps virus strain L-Zagreb master seed, complete genome," [online]. Bethesda, MD [retrieved on Jul. 1, 2014]. Retrieved from the Internet: <URL: http://www.ncbi.nlm.nih.gov/nuccore/AY685921>; 6 pgs.

(56) References Cited

OTHER PUBLICATIONS

National Center for Biotechnology Information, National Library of Medicine, National Institutes of Health, GenBank Locus AY685920, Accession No. AY685920, "Mumps virus strain L-Zagreb vaccine strain, complete genome," [online]. Bethesda, MD [retrieved on Jul. 1, 2014]. Retrieved from the Internet: <URL: http://www.ncbi.nlm.nih.gov/nuccore/AY685920>; 6 pgs.

National Center for Biotechnology Information, National Library of Medicine, National Institutes of Health, GenBank Locus EU370206, Accession No. EU370206, "Mumps virus strain 9218/Zg98, complete genome," [online]. Bethesda, MD [retrieved on Jul. 1, 2014]. Retrieved from the Internet: <URL: http://www.ncbi.nlm.nih.gov/nuccore/299766355>; 6 pgs.

National Center for Biotechnology Information, National Library of Medicine, National Institutes of Health, GenBank Locus AY669145, Accession No. AY669145, "Mumps virus genotype C, complete genome," [online]. Bethesda, MD [retrieved on Jul. 1, 2014]. Retrieved from the Internet: <URL: http://www.ncbi.nlm.nih.gov/nuccore/50404164>; 6 pgs.

National Center for Biotechnology Information, National Library of Medicine, National Institutes of Health, GenBank Locus AY681495, Accession No. AY681495, "Mumps virus strain MuVi/Novosibirsk.RUS/10.03-H, complete genome," [online]. Bethesda, MD [retrieved on Jul. 1, 2014]. Retrieved from the Internet: <URL: http://www.ncbi.nlm.nih.gov/nuccore/AY681495>; 6 pgs.

National Center for Biotechnology Information, National Library of Medicine, National Institutes of Health, GenBank Locus AF467767, Accession No. AF467767, "Mumps virus isolate 88-1961, complete genome," [online]. Bethesda, MD [retrieved on Jul. 1, 2014]. Retrieved from the Internet: <URL: http://www.ncbi.nlm.nih.gov/nuccore/af467767>; 6 pgs.

National Center for Biotechnology Information, National Library of Medicine, National Institutes of Health, GenBank Locus EU370207, Accession No. EU370207, "Mumps virus strain Du/CRO05, complete genome," [online]. Bethesda, MD [retrieved on Jul. 1, 2014]. Retrieved from the Internet: <URL: http://www.ncbi.nlm.nih.gov/nuccore/eu370207>; 6 pgs.

National Center for Biotechnology Information, National Library of Medicine, National Institutes of Health, GenBank Locus FJ556896, Accession No. FJ556896, "Mumps virus strain SP-A, complete genome," [online]. Bethesda, MD [retrieved on Jul. 1, 2014]. Retrieved from the Internet: <URL: http://www.ncbi.nlm.nih.gov/nuccore/FJ556896>; 6 pgs.

National Center for Biotechnology Information, National Library of Medicine, National Institutes of Health, GenBank Locus EU884413, Accession No. EU884413, "Mumps virus strain SP, complete genome," [online]. Bethesda, MD [retrieved on Jul. 1, 2014]. Retrieved from the Internet: <URL: http://www.ncbi.nlm.nih.gov/nuccore/eu884413>; 6 pgs.

National Center for Biotechnology Information, National Library of Medicine, National Institutes of Health, GenBank Locus DQ649478, Accession No. DQ649478, "Mumps virus strain strain SP, complete genome," [online]. Bethesda, MD [retrieved on Jul. 1, 2014]. Retrieved from the Internet: <URL: http://www.ncbi.nlm.nih.gov/nuccore/dq649478>; 6 pgs.

National Center for Biotechnology Information, National Library of Medicine, National Institutes of Health, GenBank Locus AF345290, Accession No. AF345290, "Mumps virus (Strain Jeryl-Lynn) live vaccine minor component JL2, complete genome," [online]. Bethesda, MD [retrieved on Jul. 1, 2014]. Retrieved from the Internet: <URL: http://www.ncbi.nlm.nih.gov/nuccore/AF345290.1>; 7 pgs.

National Center for Biotechnology Information, National Library of Medicine, National Institutes of Health, GenBank Locus FN431985, Accession No. FN431985, "Mumps virus strain Jeryl Lynn complete genome, genomic RNA, sub strain JL2," [online]. Bethesda, MD [retrieved on Jul. 1, 2014]. Retrieved from the Internet: <URL: http://www.ncbi.nlm.nih.gov/nuccore/FN431985.1>; 7 pgs.

National Center for Biotechnology Information, National Library of Medicine, National Institutes of Health, GenBank Locus GU980052, Accession No. GU980052, "Mumps virus strain Enders, complete genome," [online]. Bethesda, MD [retrieved on Jul. 1, 2014]. Retrieved from the Internet: <URL: http://www.ncbi.nlm.nih.gov/nuccore/GU980052.1>; 6 pgs.

National Center for Biotechnology Information, National Library of Medicine, National Institutes of Health, GenBank Locus AF338106, Accession No. AF338106, "Mumps virus (Strain Jeryl-Lynn) live vaccine major component, complete genome," [online]. Bethesda, MD [retrieved on Jul. 1, 2014]. Retrieved from the Internet: <URL: http://www.ncbi.nlm.nih.gov/nuccore/AF338106>; 7 pgs.

National Center for Biotechnology Information, National Library of Medicine, National Institutes of Health, GenBank Locus AF201473, Accession No. AF201473, "Mumps virus, complete genome," [online]. Bethesda, MD [retrieved on Jul. 1, 2014]. Retrieved from the Internet: <URL: http://www.ncbi.nlm.nih.gov/nuccore/AF201473>; 6 pgs.

National Center for Biotechnology Information, National Library of Medicine, National Institutes of Health, GenBank Locus FJ211586, Accession No. FJ211586, "Mumps virus strain JL1, complete genome," [online]. Bethesda, MD [retrieved on Jul. 1, 2014]. Retrieved from the Internet: <URL: http://www.ncbi.nlm.nih.gov/nuccore/fj211586>; 6 pgs.

National Center for Biotechnology Information, National Library of Medicine, National Institutes of Health, GenBank Locus FJ211585, Accession No. FJ211585, "Mumps virus strain RIT4385, complete genome," [online]. Bethesda, MD [retrieved on Jul. 1, 2014]. Retrieved from the Internet: <URL: http://www.ncbi.nlm.nih.gov/nuccore/FJ211585>; 6 pgs.

National Center for Biotechnology Information, National Library of Medicine, National Institutes of Health, GenBank Locus FJ211584, Accession No. FJ211584, "Mumps virus strain RIT4385, complete genome," [online]. Bethesda, MD [retrieved on Jul. 1, 2014]. Retrieved from the Internet: <URL: http://www.ncbi.nlm.nih.gov/nuccore/FJ211584>; 6 pgs.

National Center for Biotechnology Information, National Library of Medicine, National Institutes of Health, GenBank Locus JN012242, Accession No. JN012242, "Mumps virus strain MuV-IA, complete genome," [online]. Bethesda, MD [retrieved on Jul. 1, 2014]. Retrieved from the Internet: <URL: http://www.ncbi.nlm.nih.gov/nuccore/338784246>; 7 pgs.

National Center for Biotechnology Information, National Library of Medicine, National Institutes of Health, GenBank Locus DQ661745, Accession No. DQ661745, "Mumps virus strain MUM/Iowa.US/2006 small hydrophobic protein mRNA, complete cds," [online]. Bethesda, MD [retrieved on Jul. 25, 2014]. Retrieved from the Internet: <URL: http://www.ncbi.nlm.nih.gov/nuccore/DQ661745>; 1 pg.

Nishio et al., The carboxyl segment of the mumps virus V protein associates with Stat proteins in vitro via a tryptophan-rich motif, Aug. 2002, *Virology* 300(1):92-99.

Niwa et al., Efficient selection for high-expression transfectants with a novel eukaryotic vector, Dec. 1991, *Gene* 108(2):193-199.

Nöjd et al., Mumps virus neutralizing antibodies do not protect against reinfection with a heterologous mumps virus genotype, Feb. 2001, *Vaccine* 19(13-14):1727-1731.

Norrby et al., Differences in antibodies to the surface components of mumps virus after immunization with formalin-inactivated and live vaccines, Nov. 1978, *J. Infect. Dis.* 138(5):672-676.

Okazaki et al., Molecular cloning and sequence analysis of the mumps virus gene encoding the L protein and the trailer sequence, Jun. 1992, *Virology* 188(2):926-930.

Örvell et al., Characterization of genotype-specific epitopes of the HN protein of mumps virus, Dec. 1997, *J. Gen. Virol.* 78(12):3187-3193.

Örvell et al., Antigenic relationships between six genotypes of the small hydrophobic protein gene of mumps virus, Oct. 2002, *J. Gen. Virol.* 83(10):2489-2496.

Otto et al., Ongoing outbreak of mumps affecting adolescents and young adults in Bavaria, Germany, Aug. to Oct. 2010, Dec. 16, 2010, *Euro Surveil.* 15(50):pii=19748.

(56) References Cited

OTHER PUBLICATIONS

Palese, Genetic engineering of infectious negative-strand RNA viruses, Apr. 1995, *Trends Microbiol.* 3(4):123-125.
Parisien et al., A shared interface mediates paramyxovirus interference with antiviral RNA helicases MDA5 and LGP2, Jul. 2009, *J. Virol.* 83(14):7252-7260 (published online Apr. 29, 2009).
Paterson et al., RNA editing by G-nucleotide insertion in mumps virus P-gene mRNA transcripts, Sep. 1990, *J. Virol.* 64(9):4137-4145.
Pekosz et al., Reverse genetics of negative-strand RNA viruses: closing the circle, Aug. 1999, *Proc. Natl. Acad. Sci. USA* 96(16):8804-8806.
Poole et al., The V proteins of simian virus 5 and other paramyxoviruses inhibit induction of interferon-β, Nov. 2002, *Virology* 303(1):33-46.
Puri et al., A point mutation, E95D, in the mumps virus V protein disengages STAT3 targeting from STAT1 targeting, Jul. 2009, *J. Virol.* 83(13):6347-6356 (published online Apr. 22, 2009).
Ramachandran et al., Dissociation of paramyxovirus interferon evasion activities: universal and virus-specific requirements for conserved V protein amino acids in MDA5 interference, Nov. 2010, *J. Virol.* 84(21):11152-11163 (published online Aug. 18, 2010).
Rima et al., Polypeptide synthesis in mumps virus-infected cells, Feb. 1980, *J. Gen. Virol.* 46(2):501-505.
Roberts et al., Recovery of negative-strand RNA viruses from plasmid DNAs: a positive approach revitalizes a negative field, Jul. 1998, *Virology* 247(1):1-6.
Rosas-Murrieta et al., Interaction of mumps virus V protein variants with STAT1-STAT2 heterodimer: experimental and theoretical studies, Oct. 11, 2010, *Virol. J.* 7:263.
Rota et al., Investigation of a mumps outbreak among university students with two measles-mumps-rubella (MMR) vaccinations, Virginia, Sep.-Dec. 2006, Oct. 2009, *J. Med. Virol.* 81(10):1819-1825.
Ruah et al., Measles immunization with killed virus vaccine. Serum antibody titers and experience with exposure to measles epidemic, Mar. 1965, *Am. J. Dis. Child.* 109:232-237.
Rubin et al., The mumps virus neurovirulence safety test in Rhesus monkeys: a comparison of mumps virus strains, Aug. 1999, *J. Infect. Dis.* 180(2):521-525.
Rubin et al., Evaluation of a neonatal rat model for prediction of mumps virus neurovirulence in humans, Jun. 2000, *J. Virol.* 74(11):5382-5384.
Rubin et al., The rat-based neurovirulence safety test for the assessment of mumps virus neurovirulence in humans: an international collaborative study, Apr. 2005, *J. Infect. Dis.* 191(7):1123-1128.
Rubin et al., Serological and phylogenetic evidence of monotypic immune responses to different mumps virus strains, Mar. 2006, *Vaccine* 24(14):2662-2668.
Rubin et al., Antibody induced by immunization with the Jeryl Lynn mumps vaccine strain effectively neutralizes a heterologous wild-type mumps virus associated with a large outbreak, Aug. 2008, *J. Infect. Dis.* 198(4):508-515.
Rubin et al., Neurovirulence safety testing of mumps vaccines—Historical perspective and current status, Apr. 5, 2011, *Vaccine* 29(16):2850-2855 (published online Feb. 18, 2011).
Saito et al., Isolation and characterization of mumps virus strains in a mumps outbreak with a high incidence of aseptic meningitis, Apr. 1996, *Microbiol. Immunol.* 40(4):271-275.
Šantak et al., Mumps virus strains isolated in Croatia in 1998 and 2005: Genotyping and putative antigenic relatedness to vaccine strains, May 2006, *J. Med. Virol.* 78(5):638-643.
Sauder et al., Gene-specific contributions to mumps virus neurovirulence and neuroattenuation, Jul. 2011, *J. Virol.* 85(14):7059-7069 (published online May 4, 2011).
Schaap-Nutt et al., Human parainfluenza virus type 2 V protein inhibits interferon production and signaling and is required for replication in non-human primates, Feb. 20, 2010, *Virology* 397(2):285-298 (published online Dec. 7, 2009).
Shramek et al., Development of an attenuated mumps virus vaccine. II. Immune response of animals to vaccination with inactivated and live attenuated mumps viruses, Apr. 1969, *J. Immuol.* 102(4):1093-1098.
Stokes et al., Immunity in mumps: VI. Experiments on the vaccination of human beings with formolized mumps virus, Nov. 1946, *J. Exp. Med.* 84(5):407-428.
Stratton et al., Adverse events associated with childhood vaccines other than pertussis and rubella. Summary of a report from the Institute of Medicine, May 1994, *JAMA* 271(20):1602-1605.
Ströhle et al., A new mumps virus lineage found in the 1995 mumps outbreak in western Switzerland identified by nucleotide sequence analysis of the SH gene, Mar. 1996, *Arch. Virol.* 141(3-4):733-741.
Sun et al., Conserved cysteine-rich domain of paramyxovirus simian virus 5 V protein plays an important role in blocking apoptosis, May 2004, *J. Virol.* 78(10):5068-5078.
Sun et al., PLK1 down-regulates parainfluenza virus 5 gene expression, Jul. 24, 2009, *PLOS Pathog.* 5(7):e1000525.
Sun et al., Identification of a phosphorylation site within the P protein important for mRNA transcription and growth of parainfluenza virus 5, Aug. 2011, *J. Virol.* 85(16):8376-8385 (published online Jun. 15, 2011).
Takeuchi et al., Detection and characterization of mumps virus V protein, Sep. 1990, *Virology* 178(1):247-253.
Takeuchi et al., Variations of nucleotide sequences and transcription of the SH gene among mumps virus strains, Mar. 1991, *Virology* 181(1):364-366.
Takeuchi et al., The mumps virus SH protein is a membrane protein and not essential for virus growth, Nov. 1996, *Virology* 225(1):156-162.
Tanabayashi et al., Expression of mumps virus glycoproteins in mammalian cells from cloned cDNAs: both F and HN proteins are required for cell fusion, Apr. 1992, *Virology* 187(2):801-804.
Tatusova et al., Blast 2 Sequences, a new tool for comparing protein and nucleotide sequences, May 1999, *FEMS Microbiol. Lett.* 174(2):247-250.
Timani et al., A single amino acid residue change in the P protein of parainfluenza virus 5 elevates viral gene expression, Sep. 2008, *J. Virol.* 82(18):9123-9133.
Tompkins et al., Recombinant parainfluenza virus 5 (PIV5) expressing the influenza A virus hemagglutinin provides immunity in mice to influenza A virus challenge, May 2007, *Virology* 362(1):139-150.
Ulane et al., STAT3 ubiquitylation and degradation by mumps virus suppress cytokine and oncogene signaling, Jun. 2003, *J. Virol.* 77(11):6385-6393.
Utz et al., Phylogenetic analysis of clinical mumps virus isolates from vaccinated and non-vaccinated patients with mumps during an outbreak, Switzerland 1998-2000, May 2004, *J. Med. Virol.* 73(1):91-96.
Watson-Creed et al., Two successive outbreaks of mumps in Nova Scotia among vaccinated adolescents and young adults, Aug. 2006, *CMAJ* 175(5):483-488.
Waxham et al., Cloning and sequencing of the mumps virus fusion protein gene, Aug. 1987, *Virology* 159(2):381-388.
Weibel et al., Live attenuated mumps-virus vaccine. 3. Clinical and serologic aspects in a field evaluation, Feb. 1967, *N. Eng. J. Med.* 276(5):245-251.
Whelan et al., Ongoing mumps outbreak in a student population with high vaccination coverage, Netherlands, 2010, Apr. 29, 2010, *Euro Surveill.* 15(17):pii=19554.
Wilson et al., Function of small hydrophobic proteins of paramyxovirus, Feb. 2006, *J. Virol.* 80(4):1700-1709.
Xu et al., "Study of the Function of Mumps Virus Small Hydrophobic Protein," Abstract, Georgia Veterinary Scholars Program Research Day, Oct. 10, 2010, (University of Georgia, College of Veterinary Medicine) Athens, Georgia; 1 pgs.
Xu et al., "Study of the Function of Mumps Virus Small Hydrophobic Protein," Abstract, 2010 American Society for Virology Annual Conference, Bozeman, Montana, Jul. 17-21, 2010, available online Jun. 1, 2010; 1 pgs.
Xu et al., "Study of the Function of Mumps Virus Small Hydrophobic Protein," Poster, 2010 American Society for Virology Annual Conference, Bozeman, Montana, Jul. 17-21, 2010.

(56) References Cited

OTHER PUBLICATIONS

Xu et al., Rescue of wild-type mumps virus from a strain associated with recent outbreaks helps to define the role of the SH ORF in the pathogenesis of mumps virus, Aug. 15, 2011, *Virology* 417(1):126-136 (published online Jun. 14, 2011).
Xu et al., The V protein of mumps virus plays a critical role in pathogenesis, Feb. 2012, *J. Virol*. 86(3):1768-1776 (published online Nov. 16, 2011).
Yamanishi et al., Studies on live mumps virus vaccine. V. Development of a new mumps vaccine "AM 9" by plaque cloning, Dec. 1973, *Biken J*. 16(4):161-166.
Yates et al., Antigenic and genetic variation of the HN protein of mumps virus strains, Oct. 1996, *J. Gen. Virol*. 77(10):2491-2497.
Yin et al., Structure of the parainfluenza virus 5 F protein in its metastable, prefusion conformation, Jan. 2006, *Nature* 439:38-44.
Yokosawa et al., C-terminal region of STAT-1α is not necessary for its ubiquitination and degradation caused by mumps virus V protein, Dec. 2002, *J. Virol*. 76(24):12683-12690.
Patent Application No. PCT/US2012/026436, filed Feb. 24, 2012; International Search Report (PCT/ISA/210) mailed Jan. 2, 2013.
Patent Application No. PCT/US2012/026436, filed Feb. 24, 2012; Written Opinion (PCT/ISA/237) mailed Jan. 2, 2013.
Patent Application No. PCT/US2012/026436, filed Feb. 24, 2012; International Preliminary Report on Patentability (PCT/IB/373) issued Aug. 27, 2013.
Partial Supplementary European Search Report issued on Apr. 20, 2016, for European Application No. 12 75 0134.4, filed Aug. 26, 2013; 10 pages.
Carr et al., "Molecular Epidemiological Evaluation of the Recent Resurgence in Mumps Virus Infections in Ireland" J Clin Microbiol, Sep. 2010; 48(9):3288-94.
Garcia-Sastre et al., "Genetic Manipulation of Negative-Strand RNA Virus Genomes" Annu Rev Microbiol, 1993; 47:765-90.
Kunkel et al., "Differentiation of Vaccine and Wild Mumps Viruses by Polymerase Chain Reaction and Nucleotide Sequencing of the SH Gene: Brief Report" J Med Virol, 1995; 45:121-6.
Malik et al., "Discrimination of Mumps Virus Small Hydrophobic Gene Deletion Effects from Gene Translation Effects on Virus Virulence" J Virol, Jun. 2011; 85(12):6082-5.
Muhlemann, "The molecular epidemiology of mumps virus" Infect Genet Evol, Sep. 2004; 4(3):215-9.

* cited by examiner

*Figure 1A*

| Strain | SH Protein Sequence |
|---|---|
| Glouc1/UK96* | MPAIQPPLY LTFLLLILLYLIITLYVWIILTI TYKTAVRHAALYQRSFFHWSFDHSL |
| UK01-22 | MPAIQPPLY LTFLLLILLYLIITSYVWIILTI TYKTAVRHAALYQRSFFHWSFDHSL |
| MuV-IA | MPAIQPPLY LTFLLLILLYLIITLYVWIILTV TYKTAVRHAALYQRSFFHWSFDHSL |

*Figure 1C*

| Gene | Nucleotide identities | | Amino Acid identities |
|------|----------------------|-----------|----------------------|
| NP   | 94%                  |           | 98%                  |
| P/V  | 93%                  | P Protein | 94%                  |
|      |                      | V Protein | 93%                  |
| M    | 94%                  |           | 99%                  |
| F    | 94%                  |           | 95%                  |
| SH*  | 87%                  |           | 85%                  |
| HN   | 92%                  |           | 94%                  |
| L    | 94%                  |           | 98%                  |

```
               PX5F →                    1106bp           ← PX5R
rMuV    [NP] [GE/GS] [P/V]    GGGGGGGCCGGG    [P/V] AA           [GE/GS] [M]

Nhe I
rMuVΔV  [NP] [GE/GS] [P/V]    GAGGAGGGCCGGG   [P/V] AGCTAGCTAGCA [GE/GS] [M]
               PX5F →              1108bp        ← PX6R
```

| virus strain | Number of rescue | Negative control | Positive control | Nucleotide change | Amino acid residue change | Region |
|---|---|---|---|---|---|---|
| px2-sp-2 | 1 | - | + | 13704 C>A | A1750D | L gene |
| px2-sp-48 | 4 | - | + | 1899 A>T | No | NP gene end |
| px2-sp-51 | 5 | - | + | 1913 C>T | No | P/V gene start |
| Px2-sp-61 | 6 | - | + | 1899 A>G | No | NP gene end |
| PX2-SP-81 | 8 | - | + | 1899 A>G | No | NP gene end |
| PX2-SP-91 | 9 | - | + | 1896T>G | No | NP gene end |
| PX2-SP-101 | 10 | - | + | 1899A>G | No | NP gene end |
| PX2-SP-106 | 11 | - | + | 1897T>G | No | NP gene end |

*Figure 10B*

```
                          Gene End        Intergenic     Gene Start
(+)                         (GE)             (IG)           (GS)
┌────────┬──────┐   ─────────────────   ─────────    ──────────────   ┌──────┬───────┐
│ NP ORF │ 3'UTR│   AGTCTTTAAGAAAAAA      TT         AGGCCCGGAAAGAA   │ 5'UTR│ P ORF │
└────────┴──────┘                                                     └──────┴───────┘
                            ↑                                             ↑
                   1891th in plasmid px2                         1922th in plasmid px2
```

| Virus strain | Sequence | | Mutation site |
|---|---|---|---|
| | NP GE | P/V GS | |
| PX2-SP-48 | AGTCTTTA*T*GAAAAAA  TT | AGGCCCGGAAAGAA | 1899 A-T |
| PX2-sp-51 | AGTCTTTAAGAAAAAA  TT | AGGCT*C*GGAAAGAA | 1913 C-T |
| PX2-sp-61 | AGTCTTTA*G*GAAAAAA  TT | AGGCT*C*GGAAAGAA | 1899 A-G |
| PX2-sp-81 | AGTCTTTA*G*GAAAAAA  TT | AGGCCCGGAAAGAA | 1899 A-G |
| PX2-sp-91 | AGTCT*G*TAAGAAAAAA  TT | AGGCCCGGAAAGAA | 1896 T-G |
| PX2-sp-101 | AGTCTTTA*G*GAAAAAA  TT | AGGCCCGGAAAGAA | 1899 A-G |
| PX2-sp-106 | AGTCTT*G*AGAAAAAA  TT | AGGCCCGGAAAGAA | 1897 T-G |

ELISA of Mouse Sera (1:1024 dilution)

*Figure 19*

RECOMBINANT MUMPS VIRUS VACCINE

CONTINUING APPLICATION DATA

This application is the §371 U.S. National Stage of International Application No. PCT/US2012/026436, filed 24 Feb. 2012, which claims the benefit of U.S. Provisional Application Ser. No. 61/446,619, filed Feb. 25, 2011, and U.S. Provisional Application Ser. No. 61/529,981, filed Sep. 1, 2011, each of which is incorporated by reference herein.

GOVERNMENT FUNDING

This invention was made with government support under Grant No. K02AI065795, awarded by the National Institutes of Health. The Government has certain rights in the invention.

BACKGROUND

Mumps virus (MuV), a paramyxovirus, causes acute parotitis in humans, characterized by lateral or bilateral swelling of the salivary glands. MuV is also notable as a highly neurotropic and neurovirulent agent causing a number of central nervous system (CNS) manifestations ranging from mild meningitis to severe, and occasionally fatal, encephalitis. Mumps virus infection was the most common cause of viral meningitis and encephalitis until the arrival of mass immunization with mumps virus vaccine. The incidence of mumps and its complications were dramatically reduced following the introduction of measles, mumps, rubella vaccine (MMR) in 1971. MMR vaccine containing the Jeryl Lynn (JL) strain, an attenuated strain of MuV, is highly efficacious and produces few adverse reactions. Currently, mumps virus vaccination is a part of a two dose MMR (mumps, measles, and rubella) vaccine regimen that is administrated to children at one and five years of age in the United States.

In recent years, MuV has caused epidemics among highly vaccinated populations. In 2006, the U.S. experienced the largest mumps epidemic in nearly 20 years (Marin et al., 2008, *Vaccine;* 26(29-30):3601-3607). The outbreak originated at a university in Iowa and spread to eleven other states. Over 5000 mumps cases were reported in 2006 compared to an average of approximately 250 cases/year in the previous decade. In 2009-2010, a mumps outbreak occurred in the State of New York and the State of New Jersey in the US in which 88% of the patients had one-dose of mumps vaccine and 75% of the patients had two doses of vaccine (*MMWR Morb Mortal Wkly Rep;* 59(5):125-129, 2010).

While definitive causes for these recent outbreaks are not known, possible reasons (not mutually exclusive) for these outbreaks include waning immunity, high velocity of infection, and vaccine failure due to emerging of a new mumps virus strain. See, for example, (Crowley and Afzal, 2002, *Commun Dis Public Health;* 5(4):311-313; Lim et al., 2003, *J Med Virol;* 70(2):287-292; Otto et al., 2010, *Euro Surveill;* 15(50); Strohle et al., 1996, *Arch Virol;* 141(3-4):733-741; Utz et al., 2004, *J Med Virol;* 73(1):91-96; and Whelan et al., 2010, *Euro Surveill;* 15(17). The results of a large study to examine the efficacy of the two-dose MMR against mumps virus by CDC indicate that titers of anti-MuV dropped dramatically 12 years after the second dose of MMR (17 years of age), to the level of pre-second dosage inoculation. Furthermore, neutralizing antibody titers are low in adults: out of 101 sera tested, 74 were positive using ELISA and only one had neutralization antibody titer higher than 1:8. This is consistent with the fact that in the 2006 outbreak, the most affected population was 18 to 24 years of age. In the 2010 outbreak, most affected patients were 13 to 14 years of age. Both recent outbreaks occurred in high-density populations (college campus and religious school). High velocity infection (for example, large quantity of infectious virions transmitted from one to another due to close contact) may have overwhelmed the anti-MuV immunity in recent outbreaks.

The current vaccine Jeryl Lynn (JL) is based in MuV genotype A, while recent outbreaks have been caused by genotype G. It is possible that vaccine generated immunity based on strain A is ineffective in preventing infection of strain G, leading to the outbreak. Because of re-emerging of mumps virus outbreaks even in vaccinated populations, mumps virus has been listed as a high priority pathogen by National Institute of Allergy and Infectious Diseases (see "Emerging and Re-emerging Infectious Diseases" on the worldwide web at niaid.nih.gov/topics/emerging/list.htm). Currently, live attenuated MuV vaccines are obtained through serial passages in embryonic eggs and cells. This is a time consuming process and a strategy with a poor record of generating safe vaccines.

Thus, there is a need for new and improved mumps vaccines, including the development of vaccines directed at the genotype G and a need for new and improved methods for developing mumps vaccines.

SUMMARY OF THE INVENTION

The present invention includes an isolated nucleotide sequence including a cDNA sequence encoding the full length RNA genome of a mumps virus, wherein the isolated nucleotide sequence encodes a mumps virus unable to express a small hydrophobic (SH) protein product and/or unable to express a V protein product, and fragments and derivatives thereof.

In some aspects, an isolated nucleotide sequence including a cDNA sequence encoding the full length RNA genome of a mumps virus unable to express a small hydrophobic (SH) protein product includes a deletion of the open reading frame (ORF) encoding the SH protein, a mutation converting a start codon into a stop codon, or a mutation in the region between F protein ORF and the SH protein ORF that disrupts transcription of the SH gene. In some aspects, a deletion of the open reading frame (ORF) encoding the SH protein includes a deletion of 156 nucleotides of the ORF encoding the SH protein.

In some aspects, an isolated nucleotide sequence including a cDNA sequence encoding the full length RNA genome of a mumps virus unable to express a V protein product includes one or more mutations to the V/I/P gene abrogating expression of the V protein. In some aspects, one or more mutations to the V/I/P gene abrogating expression of the V protein include the nucleotide sequence GAGGAGGG at the editing site in the P/V gene.

In some aspects, an isolated nucleotide sequence including a cDNA sequence encoding the full length RNA genome of a mumps virus includes a deletion of the open reading frame (ORF) encoding the SH protein or a mutation converting a start codon into a stop codon and includes one or more mutations to the V/I/P gene abrogating expression of the V protein. In some aspects, the one or more mutations to the V/I/P gene abrogating expression of the V protein include the nucleotide sequence GAGGAGGG at the editing site in the P/V gene.

The present invention also includes an isolated nucleotide sequence including a cDNA sequence encoding the full length RNA genome of a mumps virus as described herein, including one or more further mutations and/or deletions. In some aspects, a further mutation or deletion may include a mutation or deletion effecting phosphorylation of the P protein. In some aspects, a further mutation or deletion effecting phosphorylation of the P protein may include a mutation or deletion at T147 and/or S307 of the P protein.

The present invention also includes an isolated nucleotide sequence including a cDNA sequence encoding the full length RNA genome of a mumps virus as described herein, further including expression of an I protein product and/or further including mutations in the L protein product.

The present invention also includes an isolated nucleotide sequence including a cDNA sequence encoding the full length RNA genome of a mumps virus as described herein, wherein the mumps genome further encodes a heterologous polypeptide.

In some aspects, an isolated nucleotide sequence including a cDNA sequence encoding the full length RNA genome of a mumps virus belongs to genotype G.

In some aspects, an isolated nucleotide sequence including a cDNA sequence encoding the full length RNA genome of a mumps virus is MuV/IowaUS/2006 (MuV-IA). In some aspects, MuV/IowaUS/2006 (MuV-IA) includes SEQ ID NO:1.

The present invention includes an isolated nucleotide sequence including a cDNA sequence encoding the full length RNA genome of the MUV/IowaUS/2006 (MuV-IA) strain of the mumps virus, and fragments and derivatives thereof. In some aspects, the nucleotide sequence includes SEQ ID NO:1.

The present invention includes a recombinant mumps virus (rMuV) having an isolated nucleotide acid sequence including a cDNA sequence encoding a full length RNA genome of a mumps virus, as described herein, or a fragment or derivative thereof.

The present invention includes a plasmid encoding a measles virus genome (pMuV) including a cDNA sequence encoding a full length RNA genome of a mumps virus, as described herein, or a fragment or derivative thereof.

The present invention includes a viral expression vector including an isolated nucleotide sequence including a cDNA sequence encoding the full length RNA genome of a mumps virus as described herein, or a fragment or derivative thereof.

The present invention includes an infectious viral particle including an isolated nucleotide sequence or plasmid as described herein.

The present invention includes a composition including an isolated nucleotide sequence, plasmid, pMuV, rMuV, or infectious viral particle as described herein. In some embodiments, a composition further includes a rubella and/or measles antigenic determinant. In some embodiments, the composition is formulated for intranasal, oral, intradermal, or intramuscular administration.

The present invention includes a method of inducing an immune response to mumps virus in a subject, the method including administering an effective amount of an isolated nucleotide sequence plasmid, pMuV, rMuV, viral particle, or composition as described herein, to the subject. In some embodiments, administration includes intranasal, oral, intradermal, or intramuscular administration.

The present invention includes a method of vaccinating a subject against mumps, the method including administering an effective amount of an isolated nucleotide sequence plasmid, pMuV, rMuV, viral particle, or composition as described herein to the subject. In some embodiments, administration includes intranasal, oral, or intramuscular administration.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1A-1C. Analysis of MuV-IA genome. FIG. 1A is an alignment of the SH proteins. SH protein sequences of three strains, Glouc1/UK96 (SEQ ID NO:4), UK01-22 (SEQ ID NO:5) and MuV-IA (SEQ ID NO:6) are shown. MuV-IA was different from Glouc1/UK96* and UK01-22 for only five nucleotides and two amino acids respectively. The transmembrane domain of mumps virus SH protein, outlined in rectangular box, was predicted using TMHMMserver v.2.0 (CBS; Denmark). FIG. 1B is a sequence comparison of different mumps viruses. The genome sequences of 32 strains of mumps viruses were obtained from NCBI Genbank and aligned with genome sequence of MuV-IA using MEGA4 version 4.0.2. The 32 MuV Strains were (accession numbers are given in the brackets): 87-1004 (AF314560), SIPAR 02 (AF314558), Biken (AF314561), 87-1005 (AF314562), MuV (2001) (AF314559), Urabe 1004-10/2 (FJ375177), Urabe Gw7 (FJ375178), Hoshino (AB470486), Miyahara (1992) (NC_002200), MuV Miyahara (1992) (2) (AB040874), Y213(AB576764), Dg1062/Korea/98 (32172464), L3/Russia/Vector (AY508995), L-Zagreb master seed (AY685921), L-Zagreb vaccine strain (AY685920), 9218/Zg98 (299766355), Novosbrisk genotype C (50404164), PetroNov genotype H (AY681495), 88-1961 (AF467767), Glouc1/UK96(AF280799), Du/CRO05 (EU370207), SP-A (FJ556896), SP (EU884413), SP (2006) (DQ649478), JL2 (AF345290.1), Jeryl Lynn sub strain (FN341985), Enders (GU980052.1), Jeryl Lynn major component (AF338106), MuV (2000) (AF201473), JL1 (FJ211586), RIT4385 (FJ211585), RIT4385(2) (FJ211584). FIG. 1C is a sequence comparison between MuV-IA and Jeryl Lynn (JL) strain (major component). The gene and protein sequences of NP, P/V (encoding P protein and V protein), M, F, SH, HN and L of MuV-IA and Jeryl Lynn live vaccine major component were aligned using NCBI BLAST program. Nucleotide identities and amino acid identities were shown above. *The SH genes were aligned using MEGA 4.0.2.

FIGS. 2A-2D. Analysis of rMuV, rMuV-EGFP and rMuV-RL. FIG. 2A shows the growth rate of rMuV. rMuV was obtained by transfecting BSRT-7 cells with pMuV-IA, pCA-GGS-NP, pCAGGS-P and pCAGGS-L. Growth rates of rMuV (empty square) and MuV-IA (filled triangle) were compared. FIG. 2B shows viral protein expression levels of rMuV and MuV-IA. Six well plates of Vero cell were infected with mock, rMuV or MuV-IA at a MOI of 0.5. Cell lysates were subjected to immunoblotting with anti-NP, P or V. FIG. 2C shows rescue of rMuV-EGFP. rMuV-EGFP was rescued in a similar manner as described for rMuV. Vero cell in six well plates were infected with mock or rMuV-EGFP at a MOI of 0.05 and photographed at 2 dpi. FIG. 2D shows rescue of rMuV-RL. rMuV-RL was recovered from cloned DNA as described for rMuV. 24 well plates of Vero cell were infected with mock or rMuV-RL at MOI of 0.1. At 2 dpi, cells were assayed for renilla luciferase activity.

FIG. 3A is a schematic of the production of rMuVΔSH. The SH ORF (SEQ ID NO:7) was replaced with a 5 amino acid coding sequence containing an Nhe I site (SEQ ID NO:8; restriction site is underlined). FIG. 3B is confirmation of rMuVΔSH by RT-PCR. After plaque purification, viral RNA was extracted and was subjected to RT-PCR, in which two primers flanking the SH gene were used to perform a PCR to confirm the deletion. Lane 1 and Lane 6 are 100 bp and 1 kb DNA ladder respectively; Lane 2 is the negative control—PCR without polymerase. Lane 3, 4 and 5 are PCR products from rMuVΔSH, rMuV and wtMuV-infected cells respectively. FIG. 3C is confirmation of rMuVΔSH by sequencing. PCR products were sequenced (SEQ ID NO:9). The inserted sequence is underlined. FIG. 3D shows expression of SH in MuV-IA, rMuV and rMuVΔSH-infected cells. Vero cells were mock infected or infected with MuV-IA, rMuV or rMuVΔSH. Cell lysates were subjected to immunoblotting with anti-NP, P or SH.

FIGS. 4A-4D. Growth rates and viral protein expression of rMuVΔSH and rMuV. FIG. 4A shows growth rates of rMuVΔSH and rMuV. Vero cell were infected with rMuVΔSH (filled diamond) and rMuV (empty square) at MOI of 0.01. Supernatants were used for plaque assay. FIG. 4B shows viral protein expression levels in rMuVΔSH and rMuV infected cells. Vero cells were mock infected or infected with rMuVΔSH or rMuV at a MOI of 0.5. FIG. 4C shows HN expression level in rMuVΔSH and rMuV infected cells. Vero cells were mock infected or infected with rMuVΔSH or rMuV at a MOI of 0.5. Cells were collected at 24 hpi and expression levels of total HN and NP were examined using flow cytometry. Mean fluorescence intensity (MFI) of HN and NP were calculated. Y-axis represents the relative ratio of MFI of HN normalized by MFI of NP. FIG. 4D shows HN mRNA level in rMuVΔSH or rMuV infected Vero cells. Viral RNA was extracted from rMuVΔSH or rMuV-infected Vero cells, reverse transcribed with oligodT and used for real time PCR. HN and F mRNA levels were calculated and RN mRNA level was normalized by F mRNA level. Y-axis represents ratio of HN mRNA verses F mRNA.

FIGS. 5A-5C. Induction of cell death by rMuVΔSH. FIG. 5A shows cytopathic effects of rMuVΔSH or rMuV in tissue culture cell lines. Vero cells, MDBK cells or HeLa cells were mock infected or infected with rMuVΔSH or rMuV at MOI of 0.01 and photographed at 1 dpi. FIG. 5B shows cytopathic effects of rMuVΔSH infection in L929 cells. L929 cells were mock infected, or infected with rMuVΔSH, or rMuV at a MOI of 3 and were photographed at 1 dpi and 2 dpi. FIG. 5C shows rMuVΔSH infection induced apoptosis in L929 cells. L929 cells were infected as in FIG. 5B. At 1 dpi, both floating cells and attached cells were collected, fixed, permeabilized and used for TUNEL assay.

FIGS. 6A-6D. The role of TNF-α in rMuVΔSH-mediated cell death. FIG. 6A shows rMuVΔSH infection activated P65 in L929 cells. L929 cells on glass cover slips were infected with mock, rMuVΔSH or rMuV at a MOI of 10. At 1 dpi, L929 cells on the cover slips were stained with anti-P65. FIG. 6B shows rMuVΔSH infection in L929 cells induced TNF-α production. L929 cells were mock infected or infected with rMuVΔSH, or rMuV at a MOI of 5. TNF-α in the media was measured using ELISA. FIG. 6C shows treatment with anti-TNF-α antibody reduced CPE in rMuVΔSH infected L929 cells. L929 cells were mock infected or infected with rMuVΔSH or rMuV at a MOI of 5. Cells were cultured in media containing TNF-α neutralizing antibody or control antibody and were photographed at 1 dpi. FIG. 6D shows TNF-α antibody treatment inhibited apoptosis in rMuVΔSH infected L929 cells. L929 cells in 6 well plates were infected and treated as in FIG. 6C. At one day and two days post infection, cells were collected and used for TUNEL assay.

FIG. 8. Neurotoxicity of MuVΔSH in vivo. Newborn rats were infected intracerebrally with rMuV or rMuVΔSH. The animals were sacrificed at 30 days post infection. The brains of the animals were sectioned, stained and neurotoxicity scores were calculated based on relative hydrocephalus score as described in the Material and Methods.

FIGS. 9A-9D. Generation of a MuV$^{Iowa/US/06}$ lacking V protein (rMuV$^{Iowa/US/06}$ΔV). FIG. 9A is a schematic of rMuV$^{Iowa/US/06}$ΔV. The GGGGGG (nucleotides 1-6 of SEQ ID NO:14) editing site in the P/V gene of MuV$^{Iowa/US/06}$ was changed to GAGGAGGG (nucleotides 1-8 of SEQ ID NO:15) to eliminate expression of the V protein. To maintain the genome length of rMuV$^{Iowa/US/06}$ΔV to be a multiple of six, four basepairs (bp) were added to the P/V gene 3' UTR (SEQ ID NO:16). FIG. 9B shows confirmation of the rescue of rMuV$^{Iowa/US/06}$ΔV. Viral RNAs extracted from rMuV$^{Iowa/US/06}$ΔV- and rMuV$^{Iowa/US/06}$-infected cells were reverse transcribed into cDNA, followed by reverse transcription (RT)-PCR using two primers flanking the P/V gene. Lane 1 is 100-bp DNA ladder; lane 2 is negative control (PCR without polymerase); lanes 3 and 4 are PCR products from rMuV$^{Iowa/US/06}$ΔV- and rMuV$^{Iowa/US/06}$-infected cells, respectively. FIG. 9C is confirmation of rMuV$^{Iowa/US/06}$ΔV. The PCR products shown in FIG. 9B were sequenced (SEQ ID NO:17). FIG. 9D shows expression of the V protein in rMuV$^{Iowa/US/06}$ΔV- and rMuV$^{Iowa/US/06}$-infected cells. Vero cells were mock infected or infected with rMuV$^{Iowa/US/06}$ΔV or rMuV$^{Iowa/US/06}$. Cell lysates were immunoblotted using anti-NP, -P, or -V.

FIGS. 10A and 10B. Whole-genome sequencing of rescued rMuV$^{Iowa/US/06}$ΔV. FIG. 10A is a summary of changes found in rescued rMuV$^{Iowa/US/06}$ΔV. The leftmost panel shows the names of individual rMuV$^{Iowa/US/06}$ΔV strains from eight successful virus rescues. FIG. 10B is a schematic of the changes that occurred in the NP GE and P/V GS regions. Changes that occurred during virus rescue of rMuV$^{Iowa/US/06}$ΔV are indicated as bold, italic letters. The NP GE and P/V GS sequence in the plasmid is shown (SEQ ID NO:18). The NP GE and P/V GS mutated sequences are shown for the following virus strains: PX2-SP-48 (SEQ ID NO:19), PX2-sp-51 (SEQ II) NO:20), PX2-sp-61 (SEQ ID NO:21), PX2-sp-81 (SEQ ID NO:22), PX2-sp-91 (SEQ ID NO:23), PX2-sp-101 (SEQ ID NO:24), and PX2-sp-106 (SEQ ID NO:25). The "TT" in the middle of the sequence alignment is the gene junction sequence between the NP and P/V genes in MuV$^{Iowa/US/06}$.

FIGS. 11A-11E. Growth rates and viral protein expression of rMuV$^{Iowa/US/06}$ΔV, rMuV$^{Iowa/US/06}$, and MuV$^{Iowa/US/06}$. FIG. 11A shows growth rates of rMuV$^{Iowa/US/06}$ΔV and rMuV$^{Iowa/US/06}$ in Vero cells. Vero cells were mock infected or infected with rMuV$^{Iowa/US/06}$ΔV or rMuV$^{Iowa/US/06}$ at an MOI of 0.01. Supernatants were collected for plaque assay. FIG. 11B shows plaques of rMuV$^{Iowa/US/06}$ΔV and rMuV$^{Iowa/US/06}$ in Vero cells. rMuV$^{Iowa/US/06}$ΔV or rMuV$^{Iowa/US/06}$ was plated onto Vero cells. The plaques were stained with Giemsa at 6 dpi. FIG. 11C shows viral protein expression of rMuV$^{Iowa/US/06}$ΔV and rMuV$^{Iowa/US/06}$ in Vero cells. Vero cells were infected as in FIG. 11A. Viral protein levels were examined by immunoblotting with anti-NP and P. β-Actin was used as a loading control. FIG. 11D presents growth rates of rMuV$^{Iowa/US/06}$ΔV and rMuV$^{Iowa/US/06}$ in HeLa cells. HeLa cells were infected as FIG. 11A. FIG. 11E presents growth rates of rMuV$^{Iowa/US/06}$ΔV and rMuV$^{Iowa/US/06}$ in 293T cells. 293T cells were mock infected or infected with rMuV$^{Iowa/US/06}$ΔV or rMuV$^{Iowa/US/06}$ at an MOI of 0.5. Supernatants were collected for plaque assay.

FIGS. 12A-12D. Ratios of NP and P in rMuV$^{Iowa/US/06}$ΔV-infected cells. FIG. 12A shows NP and P expression levels in rMuV$^{Iowa/US/06}$ΔV- and rMuV$^{Iowa/US/06}$-infected Vero cells during early time points postinfection. Vero cells were mock infected or infected with rMuV$^{Iowa/US/06}$ΔV or rMuV$^{Iowa/US/06}$ at an MOI of 0.5. Vero cells were collected and examined for NP and P expression using flow cytometry. Ratios of mean fluorescence intensity (MFI) of P over NP are shown. P values of rMuV$^{Iowa/US/06}$ versus rMuV$^{Iowa/US/06}$ΔV at 12 and 16 hpi were calculated using Student's t test and are less than 0.05. FIG. 12B shows NP and P expression levels in rMuV$^{Iowa/US/06}$ΔV- and rMuV$^{Iowa/US/06}$-infected Vero cells during late time points postinfection. Ratios of MFI of P over NP at multiple time points postinfection were examined as in FIG. 12A. P values of rMuV$^{Iowa/US/06}$ versus rMuV$^{Iowa/US/06}$ΔV at 24 and 48 hpi are less than 0.05. FIG. 12C shows NP and P expression ratios of rMuV$^{Iowa/US/06}$ΔV (P GS). Ratios of MFI of P over NP in rMuV$^{Iowa/US/06}$ΔV (P GS)-infected Vero cells, at an MOI of 0.5, were examined at 24 hpi. P values of rMuV$^{Iowa/US/06}$ versus rMuV$^{Iowa/US/06}$ΔV (P GS) are less than 0.05. FIG. 12D shows NP and P expression ratio of rMuV$^{Iowa/US/06}$ (L gene). Ratios of MFI of P over NP in rMuV$^{Iowa/US/06}$ΔV (L gene)-infected Vero cells, at an MOI of 0.5, were examined at 24 hpi. P values of rMuV$^{Iowa/US/06}$ versus rMuV$^{Iowa/US/06}$ΔV (L gene) are less than 0.05.

FIG. 13. HN expression level in rMuV$^{Iowa/US/06}$ΔV. Vero cells were mock infected or infected with rMuVΔV or rMuV at an MOI of 0.5. Cells were collected at 24 hpi and stained for BIN using flow cytometry.

FIGS. 14A-14C. Induction of cell death by rMuV$^{Iowa/US/06}$ΔV. In FIG. 14A, rMuV$^{Iowa/US/06}$ΔV induced a greater cytopathic effect in cell lines. HeLa cells, MDBK cells, or Vero cells were mock infected or infected with rMuV$^{Iowa/US/06}$ΔV or rMuV$^{Iowa/US/06}$ at an MOI of 0.5 and photographed at 72 hpi. FIG. 14B shows induction of apoptosis by rMuVΔV in HeLa cells. HeLa cells were infected as in FIG. 14A. At 24 hpi, cells were collected for TUNEL assay. Percentages of TUNEL-positive cells out of total cells are shown. The P value of rMuV$^{Iowa/US/06}$ versus rMuV$^{Iowa/US/06}$ΔV is less than 0.05. FIG. 14C shows induction of apoptosis in Vero cells. The Vero cells were infected with 0.5 MOI of viruses and processed for TUNEL assay as in FIG. 14B. P values between the wild type and rMuV$^{Iowa/US/06}$ΔV are less than 0.05.

FIGS. 15A and 15B. Degradation of STAT1 and STAT3 in MuV$^{Iowa/US/06}$-infected cells. As shown in FIG. 15A, rMuV$^{Iowa/US/06}$ΔV failed to degrade STAT1 in Vero cells. Vero cells were infected at an MOI of 0.5. Cell lysates were immunoblotted with anti-NP, -P, -V, and anti-STAT1 recognizing both STAT1 isoforms (STAT1α and STAT1β). β-Actin was used as a loading control. As shown in FIG. 15B, rMuV$^{Iowa/US/06}$ΔV failed to degrade STAT3 in Vero cells. Cell lysates were immunoblotted with anti-NP, -P, -V, -STAT3, and -STAT2.

FIGS. 16A and 16B. Induction of IFN-β and IL-6 by rMuV$^{Iowa/US/06}$ΔV. FIG. 16A shows induction of IFN-β production by rMuV$^{Iowa/US/06}$ΔV virus. 293T cells were infected with wild-type PIV5, rPIV5V C, rMuV$^{Iowa/US/06}$, or rMuV$^{Iowa/US/06}$ΔV or mock infected. The cellular supernatants were collected at 24 and 48 hpi and analyzed for IFN-β production by ELISA. The graph shows the average of three independent experiments, and error bars represent the standard deviation (SD). P values of rMuV$^{Iowa/US/06}$ versus rMuV$^{Iowa/US/06}$ΔV at 24 and 48 hpi are less than 0.05. FIG. 16B shows induction of IL-6 production by rMuV$^{Iowa/US/06}$ΔV virus. HeLa cells were infected with wild-type PIV5, rPIV5V C, rMuV$^{Iowa/US/06}$, or rMuV$^{Iowa/US/06}$ΔV or mock infected. The cellular supernatants were collected at 24 and 48 hpi and analyzed for IL-6 production by ELISA. The test samples were diluted to 1:10 in a sample diluent provided in the kit. The graph shows the average of two independent experiments, and error bars represent the SD. P values of rMuV$^{Iowa/US/06}$ versus rMuV$^{Iowa/US/06}$ΔV at 24 and 48 hpi are less than 0.05.

FIG. 17. Neurotoxicity of rMuV$^{Iowa/US/06}$ΔV in vivo. The severity of hydrocephalus in rats inoculated with rMuV$^{Iowa/US/06}$ or rMuV$^{Iowa/US/06}$ΔV was measured as described in Example 2. rMuVΔV-1 is rMuV$^{Iowa/US/06}$ΔV rescue #4 (PX2-SP-48) and rMuVΔV-2 is rMuV$^{Iowa/US/06}$ΔV rescue #5 (PX2-SP-51); as detailed in FIG. 10). P values of rMuV versus rMuVΔV-1 or rMuVΔV-2 are less than 0.05. The P value of rJL versus rMuVΔV-1 is less than 0.05. n=36 for MuV, n=16 for rMuVΔV-1, and n=18 for rMuVΔV-2.

FIGS. 18A and 18B. Titers of anti-MuV antibodies in the sera measured using ELISA. FIG. 18A shows titers measured at serial dilutions of the sera. FIG. 18B shows titers at a dilution of 1:1024.

FIG. 19. Schematics of MuV-F and F-MuV RSV F can be inserted between F and SH to give rise to MuV-F or between leader sequence and NP to give rise to F-MuV. The insert is a more detailed diagram of F insertion. Sequences of gene start (GS), intergenic region (I) and gene end (GE), which are important for initiation and termination of viral mRNA synthesis, are indicated.

DETAILED DESCRIPTION

Figure 1B:
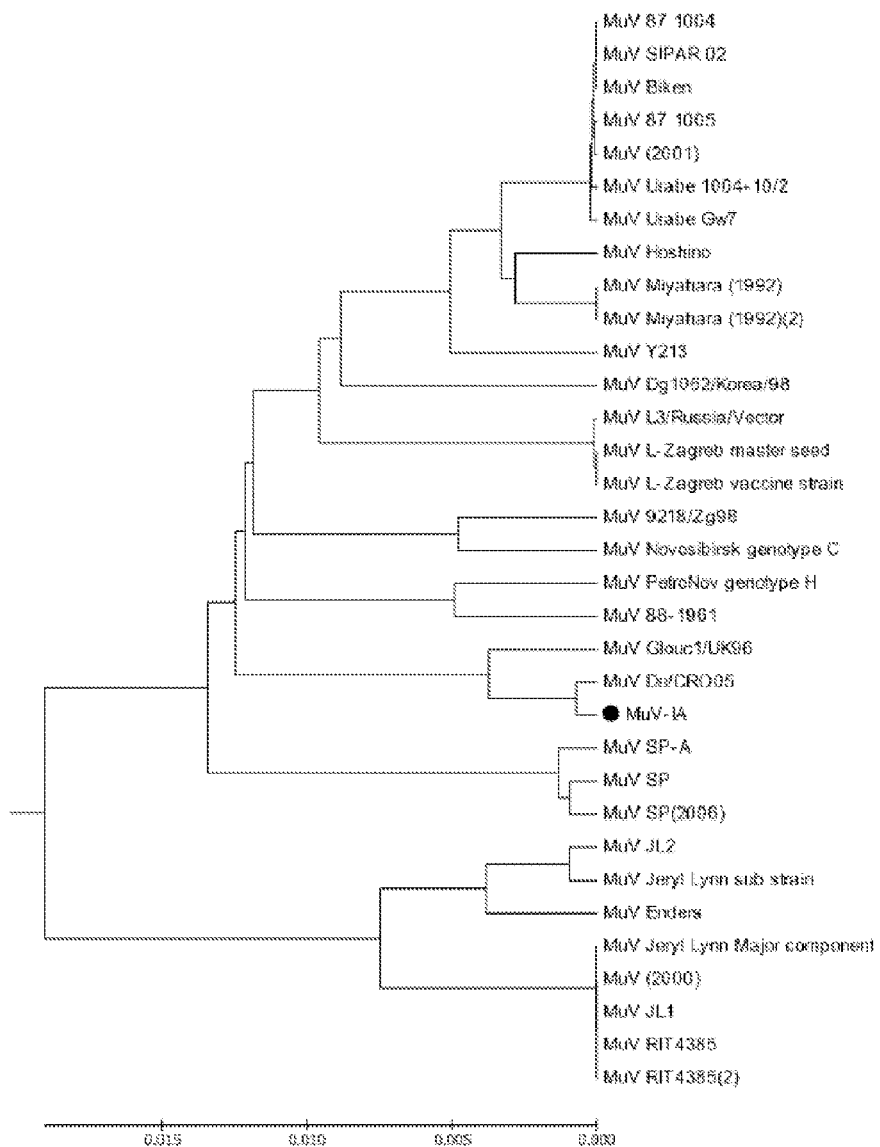

In 2006, the U.S. experienced the largest mumps epidemic in nearly 20 years (Marin et al., 2008, *Vaccine;* 26(29-30):

3601-3607). The outbreak originated at a university in Iowa and spread to eleven other states. With the present invention, the sequence of the complete genome of a clinical wild-type isolate from the Iowa mumps epidemic has been determined. This isolate, the Iowa strain, also referred to herein as MuV-IA, rMuV$^{Iowa/US/06}$, MuV Iowa/US/06, MuV-Iowa/US/06, or MuV (Iowa/US/06) is a member of genotype G, not genotype A of the widely used Jeryl Lynn (JL) mumps vaccine. A reverse genetics system was generated for this mumps virus, and using this reverse genetics system, various recombinant MuV constructs were generated, including, but not limited to, recombinant MuV lacking the expression of the viral proteins SH (rMuVΔSH) and/or V (rMuVΔV). These recombinant viruses grow well in tissue culture cells such as Vero cells, which are WHO-approved cell line for vaccine production, but are attenuated in an animal model, demonstrating lower neurotoxicity than even the JL vaccine. These recombinant viruses and their derivatives are suitable for a new generation of MuV vaccines.

Mumps virus (MuV), a member of the family Paramyxoviridae, is a negative stranded, non-segmented RNA virus with a genome of 15,384 nucleotides. The viral genome has seven genes but encodes nine known viral proteins. The nucleocapsid protein (NP), phosphoprotein (P) and large RNA polymerase (L) protein are important for transcription and replication of the viral RNA genome (Elango et al., 1988, *J Gen Virol;* 69(Pt 11):2893-2900; Okazaki et al., 1992, *Virology;* 188:926-930; and Rima et al., 1980, *J Gen Virol;* 46(2):501-505). The V/P gene encodes three proteins, I, V and P (Paterson and Lamb, 1990, *J Virol;* 64:4137-4145). Mutations in the P gene have been associated with increased virulence of mumps virus (Saito et al., 1996, *Microbiol Immunol;* 40(4):271-275). The V protein plays important roles in inhibiting interferon signaling in infected cells (Kubota et al., 2002, *J Virol;* 76(24):12676-12682; Takeuchi et al., 1990, *Virology;* 178:247-253; Ulane et al., 2003, *J Virol;* 77(11):6385-6393; and Yokosawa et al., 2002, *J Virol;* 76(24):12683-12690). The fusion (F) protein, a glycoprotein, mediates both cell-to-cell and virus-to-cell fusion in a pH-independent manner that is essential for virus entry into cells (Waxham et al., 1987, *Virology;* 159:381-388). The hemagglutinin-neuraminidase (HN), another viral glycoprotein, is also involved in virus entry (Tanabayashi et al., 1992, *Virology;* 187:801-804) and mutations in the HN gene have been implicated in mumps virus virulence (Cusi et al., 1998, *J Clin Microbiol;* 36(12):3743-3744). The matrix (M) protein plays an important role in virus assembly (Matsumoto, 1982, *Microbiol Immunol;* 26(4):285-320). The small hydrophobic (SH) protein is a 57-residue type 1, hydrophobic integral membrane protein (Elango et al., 1988, *J Gen Virol;* 69(Pt 11):2893-2900).

The present invention includes an isolated polynucleotide sequence representing a mumps viral genome as described herein, and fragments and derivatives thereof. Such mumps viral genomes include, but are not limited to, the wild type MuV-IA genome or a mumps viral genome lacking expression of the viral proteins SH (rMuVΔSH) and/or V (rMuVΔV), and derivatives and fragments thereof. MuV, as a member of the family Paramyxoviridae, has a negative stranded, non-segmented RNA genome. Thus, in preferred embodiments, an isolated polynucleotide sequence encoding the MuV-IA genome is a complementary DNA (cDNA). One such a cDNA sequence is represented by SEQ ID NO:1. The genomic sequence of the MuV-IA virus, as well as the amino acid sequence of each encoded protein may be found on the National Center for Biotechnology Information (NCPI) website (available on the world wide web at ncbi.nlm.hih.gov) under GenBank Accession No. JN012242; Version JN012242.1 (GI:338784246), which is herein incorporated by reference in its entirety. In some embodiments, an isolated polynucleotide representing the MuV-IA genome is an RNA molecule. An isolated polynucleotide representing the MuV-IA genome may be genome or antigenome RNA or cDNA. An isolated polynucleotide representing the MuV-IA genome may be a positive-sense version of the MuV genome corresponding to the replicative intermediate RNA, also referred to as an antigenome.

Also included in the present invention are derivatives of an isolated polynucleotide described herein. In some embodiments, a derivative thereof may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to a polynucleotide sequence described herein. For example, a derivative thereof may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:1, or a fragment thereof. In some embodiments, a derivative thereof may encode an amino acid sequence with at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to an amino acid sequence described herein, or encoded by a mumps viral genome described herein. For example, a derivative thereof may encode a polypeptide sequence having at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity a polypeptide sequence encoded by SEQ ID NO:1. Two polynucleotide sequences may be compared using the Blastn program of the BLAST 2 search algorithm, as described by Tatusova and Madden, 1999, *FEMS Microbiol Lett;* 174:247-250), and available on the world wide web at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on.

In some embodiments, a derivative thereof hybridizes under "stringent conditions," also referred to herein as "high stringency conditions," to a polynucleotide sequence described herein. For example, a derivative thereof may hybridizes under stringent conditions to SEQ ID NO:1. Such a derivative thereof may further exhibit one or more of the various functional traits described herein. Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995). "Stringent conditions" or "high stringency conditions," as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

In some aspects, a derivative thereof includes the deletion and/or addition of nucleotide sequences so that the derivative nucleotide sequences complies with "the rule of six." See, for example, Kolakofsky et al., 1998, *J Virol;* 72:891-899.

Also included in the present invention are fragments of isolated polynucleotides, and derivatives thereof. Such fragments may include only a portion of the MuV genome, for example, encoding only one, two, three, four, five, six, seven, or eight of the nine mumps viral proteins. In some aspects, a fragment may serve as a primer or probe.

A fragment thereof may include a fragment of a mumps virus genome determined by any of the primer pairs described in Table 1 or Table 2. For example the fragment determined by any one of PX1F, PX3F, PX5F, PX7F, PX9F, PX11F, PX13F, PX15F, PX17F, PX19F, PX21F, PX23F, PX25F, PX27F, PX29F, PX31F, or PX33F paired with any one of PX2R, PX4R, PX6R, PX8R, PX10R, PX12R, PX14R, PX16R, PX18R, PX20R, PX22R, PX24R, PX26R, PX28R, PX30R, PX32R, or PX34R used as a primer pair in a PCR reaction with a polynucleotide sequence described herein as a template. For example, a fragment of the present invention may represent the PCR product obtained when any one of PX1F, PX3F, PX5F, PX7F, PX9F, PX11F, PX13F, PX15F, PX17F, PX19F, PX21F, PX23F, PX25F, PX27F, PX29F, PX31F, or PX33F is used as a forward primer, and any one of PX2R, PX4R, PX6R, PX8R, PX10R, PX12R, PX14R, PX16R, PX18R, PX20R, PX22R, PX24R, PX26R, PX28R, PX30R, PX32R, or PX34R is used as a reverse primer on SEQ ID NO:1, or another mumps virus genome, including, but not limited to, any of those described herein.

An isolated polynucleotide, derivative, or fragment thereof may include additional sequences not of mumps origin. Such heterologous sequences may, for example, encode additional antigenic determinants or other additional components, such as promoter, transcription initiation, and/or and termination sequences.

Included with the present invention are vectors and other constructs that incorporate an isolated polynucleotide sequence encoding a mumps virus genome, such as MuV-IA, or a derivative, or fragment thereof. Such a vector may be an expression vector. One such vector construct is a plasmid that includes the polynucleotide sequence encoding the complete genome of MuV, such as the MuV-IA. Such a plasmid is referred to herein as a "pMuV." The present invention includes a pMuV including any of mumps genomes described herein. In some embodiments, the genome sequence may be a cDNA sequence.

The present invention includes a reverse genetics system including a mumps virus described herein, such as the MuV-IA genomic sequence, or a mutant, or derivative thereof. Reverse genetics systems, as described in more detail in the examples included herewith, can be used to generate in vitro infectious virus particles. See also, He et al., 1997, *Virology;* 237(2):249-60 and Tompkins et al., 2007, *Virology;* 362(1):139-50. Such infectious viral particles are referred to herein as recombinant MuV, also referred to herein as rMuV. A rMuV is produced by recombinant means and is, thus, not naturally occurring. A rMuV may function as an infectious viral particle. Included in the present invention are rMuV that express any of the mumps viral genomes described herein. For example, a mumps viral genome unable to express a small hydrophobic (SH) protein product and/or unable to express a V protein product, including, but not limited to, the rMuVΔSH, rMuVΔV, or rMuVΔSHΔV constructs described herein.

A mumps viral genome as described herein, may belong to the G serotype or the A serotype. A mumps viral genome may, for example, be the mumps virus strain MuV-IA, Glouc1/UK96(AF280799), UK01-22, 87-1004 (AF314560), SIPAR 02 (AF314558), Biken (AF314561), 87-1005 (AF314562), MuV (2001) (AF314559), Urabe 1004-10/2 (FJ375177), Urabe Gw7 (FJ375178), Hoshino (AB470486), Miyahara (1992) (NC_002200), MuV Miyahara (1992) (2) (AB040874), Y213(AB576764), Dg1062/Korea/98 (32172464), L3/Russia/Vector (AY508995), L-Zagreb master seed (AY685921), L-Zagreb vaccine strain (AY685920), 9218/Zg98 (299766355), Novosbrisk genotype C (50404164), PetroNov genotype H (AY681495), 88-1961 (AF467767), Du/CRO05 (EU370207), SP-A (FJ556896), SP (EU884413), SP (2006) (DQ649478), JL2 (AF345290.1), Jeryl Lynn sub strain (FN341985), Enders (GU980052.1), Jeryl Lynn major component (AF338106), MuV (2000) (AF201473), JL1 (FJ211586), RIT4385 (FJ211585), or RIT4385(2) (FJ211584). In some preferred embodiments, the mumps viral genome is MuV-IA.

A mumps viral genome unable to express a small hydrophobic (SH) protein product may include a deletion of the open reading frame (ORF) encoding the SH protein or a mutation converting a start codon into a stop codon. For example, the deletion of the open reading frame (ORF) encoding the SH protein may include a deletion of about 156 nucleotides of the ORF encoding the SH protein.

A mumps viral genome unable to express a V protein product may include one or more mutations to the V/I/P gene abrogating expression of the V protein. In some aspects, one or more mutations to the V/I/P gene abrogating expression of the V protein may include the nucleotide sequence GAGGAGGG at the editing site in the P/V gene.

A genome of a mumps virus of the present invention may include one or more further mutations and/or deletions. In some aspects, a further mutation or deletion may include a mutation or deletion effecting phosphorylation of the P protein. In some aspects, a further mutation or deletion effecting phosphorylation of the P protein may include a mutation or deletion at T147 and/or S307 of the P protein. Also included in the present invention is a mumps virus genome, as described herein, further including sequences that allow for the expression of an I protein product. In some aspects, a further mutation or deletion may include a mutation or deletion of the L gene. IN some aspects, a further deletions and/or mutations may be selected from any of those know to one of skill in the art.

The present invention also includes a mumps virus genome as described herein, wherein the mumps genome further encodes a heterologous polypeptide. Such a heterologous polypeptide may be for example, an antigenic polypeptide of non-mumps origin, or a detectable marker, such as, for example GFP or luciferase.

Also included in the present invention are compositions including one or more of the isolated polynucleotide sequences, pMuV, rMuV, vector constructs, infections viral particles, and/or viral constructs, as described herein. Such a composition may include a pharmaceutically acceptable carrier. As used, a pharmaceutically acceptable carrier refers to one or more compatible solid or liquid fillers, diluents or encapsulating substances which are suitable for administration to a human or other vertebrate animal. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water, aqueous buffer (such as buffered saline), alcohols, and polyols (such as glycerol). Such compositions and/or carriers may be pyrogen free.

Compositions of the invention may include an adjuvant, including, but not limited to aluminum hydroxide; aluminum phosphate; QS-21 Stimulon; 3-O-deacylated monophosphoryl lipid A; IL-12; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to a MTP-PE); cholera toxin; and non-toxic derivatives of cholera toxin, including its B subunit; procholeragenoid, and fungal polysaccharides.

Compositions of the present invention may include additional active immunogens, including other immunologically active antigens against other pathogenic species. The other immunologically active antigens may be replicating agents or non-replicating agents. Replicating agents include, for example, attenuated forms of measles virus, rubella virus, variscella zoster virus (VZV), Parainfluenza virus (PIV), and Respiratory Syncytial virus (RSV). Such an additional agent may be one or more of those currently used in the combination measles-mumps-rubella (MMR) and measles-mumps-rubella-varicella (MMRV) vaccines. The formulation of such compositions is well known in the art.

The present invention also includes methods of making and using the viral vectors and compositions described herein. The compositions of the present disclosure may be formulated in pharmaceutical preparations in a variety of forms adapted to the chosen route of administration. One of skill will understand that the composition will vary depending on mode of administration and dosage unit. The agents of this invention can be formulated for administration in a variety of ways, including, but not limited to, intravenous, topical, oral, intranasal, subcutaneous, intraperitoneal, intramuscular, and intratumor deliver. In some aspects, a composition is formulated for needle-less administration to the mucosa, for example for intranasal administration to the upper respiratory tract. It is expected that mucosal administration of the pharmaceutical composition to a mammalian subject will stimulate an immune response in mucosal tissues, including mucosal tissues that are remote from the site of administration, in addition to producing a systemic immune response in the subject.

The present invention also includes methods of inducing an immune response in a subject by administering an isolated polynucleotide sequences, pMuV, rMuV, vector constructs, infections viral particles, viral constructs, or composition, as described herein to the subject. The immune response may or may not confer protective immunity. An immune response may include, for example, a humoral response and/or a cell mediated response. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein. The induction of an immune response may include the priming and/or the stimulation of the immune system to a future challenge with an infectious agent, providing immunity to future infections. The induction of such an immune response may serve as a protective response, generally resulting in a reduction of the symptoms. The immune response may enhance an innate and/or adaptive immune response. Immunogenicity may be assayed in any of a variety of animal models, including, but not limited to, mouse, ferret, and/or non-human primates model systems.

The isolated polynucleotide sequences, pMuV, rMuV, vector constructs, infections viral particles, viral constructs, or composition of the present invention may demonstrate reduced neurotoxicity when administered to a subject, for example, in comparison to mumps vaccines in current use, such as, for example, the JL vaccine. Neurotoxicity may be assayed by any of a variety of methods, including, but not limited to, those in conventional use and any of those described herein, including a neurotoxicity test involving intracerebral inoculation into neonatal rats (Rubin et al., 2000, *J Virol;* 74:5382-5384).

The present invention also includes methods of vaccinating a subject by administering an isolated polynucleotide sequences, pMuV, rMuV, vector constructs, infections viral particles, viral constructs, or composition, as described herein to the subject. Such vaccination may result in a reduction or mitigation of the symptoms of future infection and may prevent a future infection. Preferably, these compositions have therapeutic and prophylactic applications as immunogenic compositions in preventing and/or ameliorating mumps infection. In such applications, an immunologically effective amount of at least one attenuated recombinant mumps virus of this invention is employed in such amount to cause a substantial reduction in the course of the normal mumps infection. Again, immunogenicity may be assayed in any of a variety of animal models, including, but not limited to, mouse, ferret, and/or non-human primates model systems. The isolated polynucleotide sequences, pMuV, rMuV, vector constructs, infections viral particles, viral constructs, or composition of the present invention may demonstrate reduced neurotoxicity when administered to a subject, for example, in comparison to mumps vaccines in current use, such as, for example, the JL vaccine. Neurotoxicity may be assayed by any of a variety of methods, including, but not limited to, those in conventional use and any of those described herein, including a neurotoxicity test involving intracerebral inoculation into neonatal rats (Rubin et al., 2000, *J Virol;* 74:5382-5384).

With the methods of the present invention, any of a variety of modes of administration may be used. For example, administration may be intravenous, topical, oral, intranasal, subcutaneous, intraperitoneal, intramuscular, or intratumor. In some aspects, administration is the needleless administration to a mucosal membrane, for example, by the intranasal administration to the upper respiratory tract by spray, droplet or aerosol An agent of the present disclosure may be administered at once, or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

By a "therapeutically effective amount" is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

As used herein, the term "subject" includes, but is not limited to, humans and non-human vertebrates. In preferred embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, ferrets, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

As used herein, an "isolated" substance is one that has been removed from its natural environment, produced using recombinant techniques, or chemically or enzymatically synthesized. For instance, a polypeptide, a polynucleotide, or a cell can be isolated. Preferably, a substance is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "the," and "at least one" are used interchangeably and mean one or more than one.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The description exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Rescue of Wild-Type Mumps Virus from a Strain Associated with Recent Outbreaks Defines Role of the SH ORF in the Pathogenesis of Mumps Virus With this example, the complete genome of a representative strain from the epidemic (MuV-IA) was sequenced. MuV-IA is a member of genotype G, the same genotype of MuV that was associated with the outbreak in the UK in 2004-2005. A reverse genetics system was constructed for MuV-IA (rMuV-IA) and used to rescue a virus lacking the open reading frame (ORF) of the SH gene (rMuVΔSH). rMuVΔSH infection in L929 cells induced increased NF-κB activation, TNF-α production and apoptosis compared to rMuV-IA. rMuVΔSH was attenuated in an animal model. These results indicated that the SH ORF of MuV plays a significant role in interfering with TNF-α signaling and viral pathogenesis during virus infection.

Results

Sequence of the complete genome of MuV-IA. To better understand the genetic characteristics of viruses associated with recent outbreaks in the U.S., the complete genomic sequence of a representative isolate from the Iowa outbreak was determined. It is available as GENBANK Accession No. JN012242. A set of primers was designed based on the consensus sequence derived from comparison of the genomic sequences of Jeryl Lynn, Urabe, 88.1961 and PetroNov. These primers are shown in Table 1. Viral RNA of MuV-IA was reverse-transcribed into cDNA using random hexamers, PCR reactions were then carried out using the set of primers and the products were sequenced using the corresponding primers. A second set of primers based on the sequencing results were then used to perform RT-PCR and the products overlapping with those of first round of sequencing fragments were sequenced using the primers. This second set of primers is shown in Table 2. Leader and trailer sequences were determined by performing 5'/3' RACE.

TABLE 1

Mumps virus specific primers

| Primer | Approximate genomic location | primer sequence (5' → 3') | SEQ ID NO: |
|---|---|---|---|
| PX1F | 100-300 | ATGTCGTCCGTGCTCAAAG | 48 |
| PX2R | 1100-1300 | CGGTCTCAACCCCAATCTG | 49 |
| PX3F | | GGGGGCTACCCATTGATATT | 50 |
| PX4R | 2100-2300 | GAAAAGGGGCTCAGGAATCT | 51 |
| PX5F | | TTCAGTACCCCACTGCATCA | 52 |
| PX6R | 3100-3300 | GGCTGGATTGGACTTGTGTT | 53 |
| PX7F | | CGAGGATGCCCTGAATGATA | 54 |
| PX8R | 4100-4300 | GCATAGTCTGAGCCCTGGAG | 55 |
| PX9F | | CACATTCCGACAACTGCAAA | 56 |
| PX10R | 5100-5300 | TGAACCACTGCAGGTGTCAT | 57 |
| PX11F | | GCTTGCAACCTCCCTAGGAT | 58 |
| PX12R | 6100-6300 | TGGCACTGTCCGATATTGTG | 59 |
| PX13F | | GTGTCGATGATCTCATCAGGTACT | 60 |
| PX14R | 7100-7400 | ACCTCAAAGCACGCTGATCT | 61 |
| PX15F | | GGGAATTGGGCTACTTTGGT | 62 |
| PX16R | 7900-8300 | GTGCATGAACCTGGGATTCT | 63 |
| PX17F | | GATACCGGTGATGCTAGTGTG | 64 |
| PX18R | 9100-9300 | GAAAGAAAGCCAGGGTCTTCA | 65 |
| PX19F | | GCTCTACTCATGGGGGACAA | 66 |
| PX20R | 10100-10300 | ATCAAGGTCAAGTTGGGTAGGA | 67 |
| PX21F | | CCAAGTCATCATCCCCTTTG | 68 |
| PX22R | 11100-11500 | TTGCTGACAATGGTCTCACC | 69 |
| PX23F | | CATGCCCAATATACATTGATGG | 70 |
| PX24R | 12100-12300 | TGAAGGGTACAGGAAGCAAAG | 71 |
| PX25F | | CTGGCCTTGCTTTAATTGAGA | 72 |
| PX26R | 13100-13300 | AGAGATGCTGATTCGGATGAA | 73 |
| PX27F | | GAACCAAAATTAACTGCCTACCC | 74 |
| PX28R | 14100-14300 | CCGCCTGAAGGATAATGTTG | 75 |
| PX29F | | CCCTGAATGAACAGGGGTTT | 76 |
| PX30R | 15100-15300 | CTTTTGCTGGCCTTTTGCT | 77 |
| PX31F | | CTGCTAACAAAGCCCGAAAG | 78 |
| PX32R | 16100-16300 | AAGTTGCAGGACCACTTCTG | 79 |
| PX33F | | TGACTCCCCGTCGTGTAGAT | 80 |
| PX34R | 17100-17300 | AGACGTCAGGTGGCACTTTT | 81 |

TABLE 2

MuV-IA primers

| Primer | Location | Sequence (5' → 3') | SEQ ID NO: |
|---|---|---|---|
| 5F | Iowa-L-upstream-1 | TGAATCATAGTGAATGCAGCAGG | 26 |
| 6F | Iowa-L-upstream-2 | GCCCTATTGGCGTGTCTCA | 27 |
| 7R | Iowa-L-downstream | TGGTGACGTATCGTGCCAGA | 28 |
| 10F | Iowa-NP-F | AACAGTAAGCCCGGAAGTG | 29 |
| 11R | Iowa-NP-R | CCAATGAGTACTGGTGCAAC | 30 |
| 12F | Iowa-P-F | GCGACTGGGATGAGTAAA | 31 |
| 13R | Iowa-P-R | TGGATTGGACTTGTGTTCG | 32 |
| 14F | Iowa-M-F | GCGAGACATCATACGAAG | 33 |
| 15R | Iowa-M-R | AAGCTTGACCACTATGTAGG | 34 |
| 16F | Iowa-F-F | CCTCAATGAGCAACCTATG | 35 |
| 17R | Iowa-F-R | TTAGTACCTGATGAGATCATCG | 36 |
| 18F | Iowa-SH-F-EcoRI | GAATTCATGCCGGCGATCCAAC | 37 |
| 19R | Iowa-SH-R-NheI | GCTAGCTTAGAGTGAGTGATCGAAAC | 38 |
| 20F | Iowa-HN-F | ATGGAGCCCTCGAAATTCT | 39 |
| 21R | Iowa-HN-R | AACGATGGGTGAGTTTAAATG | 40 |
| 22F | Iowa-NP-F2 | GGCTTGGGTGATGGTCTGTA | 41 |
| 23R | Iowa-NP-R2 | CATTTTGGAATCCTGCACCT | 42 |
| 24F | Iowa-HN-F2 | TGCAAGGACCATACTTCGTC | 43 |
| 25R | Iowa-HN-R2 | GAGTTCATACGGCCACCAG | 44 |
| 26F | Iowa-P-F2 | CTCAACGCCGGTAACAGAAT | 45 |
| 27F | Iowa-F-F2 | ATGAAGGTTCCTTTAGTTACTTGC | 46 |
| 28F | Iowa-P-F3 | AGCCAACTGCTCAAATCCAC | 47 |

There is only one conserved change in the putative transmembrane domain of the SH protein when the SH protein sequence of MuV-IA was compared to other strains of mumps virus in genotype G (FIG. 1A), confirming that MuV-IA belongs to genotype G (Rota et al., 2009, J Med Virol; 81(10):1819-1825). To further study the genomic divergence of MuV-IA, a phylogenetic tree was generated using the genomic sequence of MuV-IA and 32 full length genomic sequences from Genbank (FIG. 1B). Phylogenetic analysis indicated that MuV-IA is most closely related to the sequence of MuV Du/CRO05, a genotype G virus, which was isolated in Croatia in 2005 (Santak et al., 2006, J Med Virol; 78(5):638-643). A comparison of the predicted amino acid sequences between the protein coding regions of MuV-IA and Jeryl Lynn vaccine (major component) showed that while NP, M and L protein sequences are highly conserved with an identity of over 98%, there was more divergence among V, P, F, SH and HN proteins (FIG. 1C). The predicted SH protein sequences had only 85% identity.

Generation of an infectious cDNA clone for MuV-IA. To study the pathogenesis of MuV-IA, a reverse genetics system was derived. Because RNA viruses exist as a quasispecies, the consensus sequence of the genome was used as the base for the recombinant MuV. A plasmid containing a mini-genome with luciferase (Luc) reporter gene for mumps virus (pT7-MuV-Mini-Luc) similar to the PIV5 mini-genome expressing plasmid was constructed using rMuV-IA trailer and leader sequences (Lin et al., 2005, Virology; 338(2):270-280). In addition, plasmids encoding NP, P and L in the pCAGGS vector have been obtained and confirmed by sequencing. To test the functionality of the plasmids, the plasmids were transfected into BSRT7 cells. At 2 dpi, the cells were harvested and Luciferase (Luc) assays were performed. Luc activity was detected in the cell transfected with all plasmids, not ones missing P or L, indicating that the plasmids expressed functional P and L proteins. RT-PCR was conducted to amplify DNA fragments representing the complete genome and inserted into individual plasmid vectors before being assembled into a full-length genome. The plasmid with the full length genome of MuV-IA expressed under the control of a T7 (pMuV-IA) promoter (pMuV-IA) was similar to the plasmid used to generate infectious PIV5 (He et al., 1997, Virology; 237:249-260). pMuV-IA had changes in two nucleotides within the L ORF compared with consensus sequence of MuV-IA at positions of 11863 (T to C) and 12028 (C to T). However, neither of these nucleotide changes resulted in changes in the predicted L protein sequence. A recombinant MuV (rMuV-IA) was rescued using the plasmid containing the full-length genome of MuVIA. BSRT-7 cells were co-transfected with pMuV-IA and plasmids expressing viral RNA polymerase components. Individual plaques were selected and amplified in Vero cells. The entire genome of the rescued virus was sequenced and found to match the input cDNA genome sequence.

To compare time course of the growth of rMuV and MuV-TA, a multi-cycle growth assay was performed (FIG. 2A). Both viruses grew to similar peak titers in Vero cells. Viral titers in the supernatant of the infected cells increased exponentially during the first two days after infection, and reached a titer of $10^7$ pfu/ml at 48 hpi. The growth of both viruses in HeLa cells (a human cell line), MDBK cells (a bovine cell line), and L929 cells (a murine cell line) was also compared, and no obvious differences between these two viruses were observed. The viral protein expression levels in cells were also examined using Western blot (FIG. 2B) and the protein levels were similar at different time points after infection, indicating that the replication of rMuV resembles MuV-IA in tissue culture cells.

In addition, infectious recombinant viruses expressing either EGFP or Renila Luciferase (RL) protein as an extra gene were rescued. pMuVEGFP was constructed by inserting an EGFP gene, flanked by gene start (GS) of SH and gene end (GE) of NP, between F gene and SH gene in pMuV-IA, pMuV-RL was constructed through substitution of coding sequence of EGEP with that of renilla luciferase (RL) in pMuV-EGFP. Expression of EGFP or RL in the infected Vero cells was detected (FIGS. 2C and 2D).

Figure 3A:
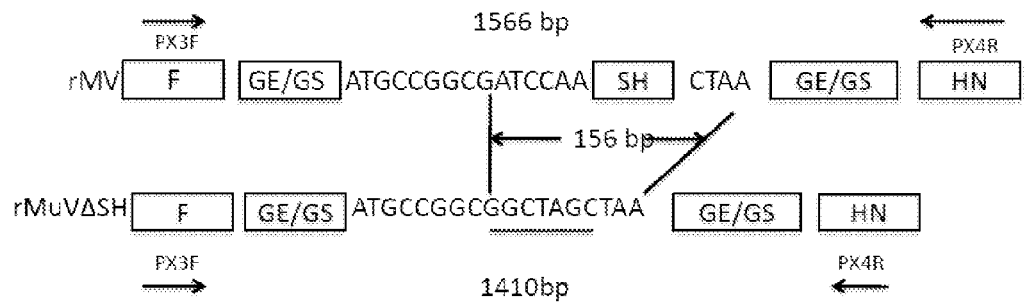
FIGS. 3A-3D. Generation of a MuV lacking SH (rMuVΔSH).
Figure 3B:
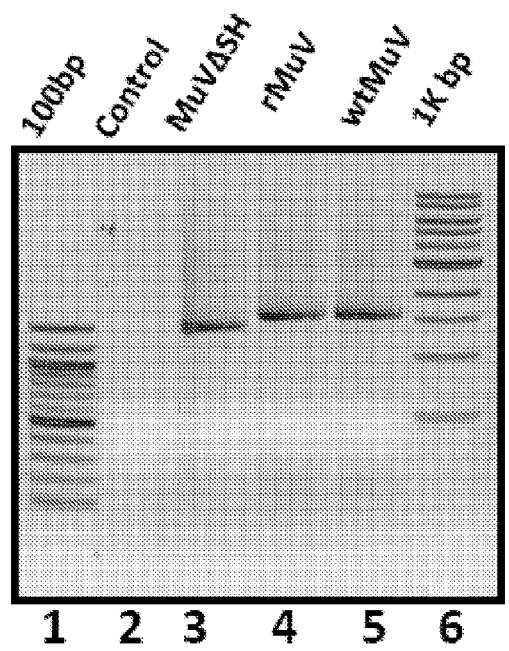
Figure 3C:
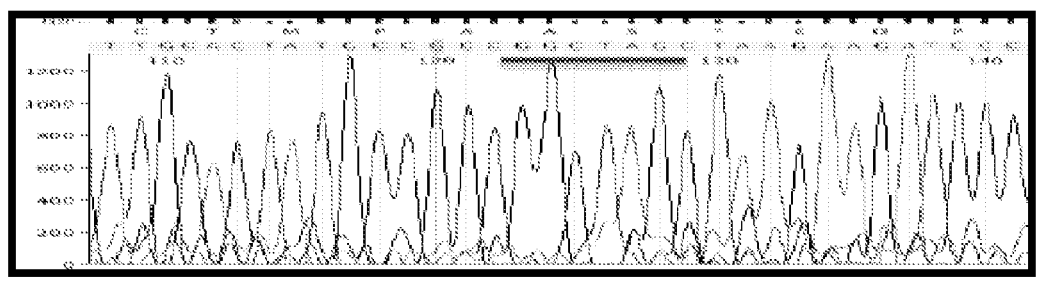
Figure 3D:
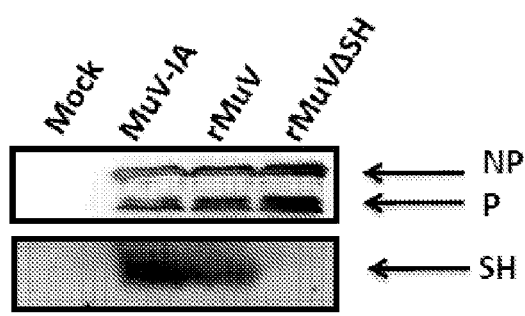

Rescue of a recombinant mumps virus lacking the SH ORF. To study the function of the SH protein of MuV, 156 nucleotides in the SH gene open reading frame (ORF) of the SH gene were deleted from pMuV-IA. The truncated SH ORF contained a short ORF encoding five amino acid residues flanked by the original SH ORF start and gene end (pMuV-IAΔSH, FIG. 3A). An infectious MuV lacking the SH ORF was rescued (rMuVΔSH) (FIGS. 3B and 3C) and the genome was sequenced, which matched the input cDNA sequence. The rMuVΔSH genome was of 15,228 nt in size, complying with "the rule of six" (Kolakofsky et al., 1998, *J Virol;* 72:891-899). To confirm that wtMuV and rMuV did express a SH protein and that rMuVΔSH did not, cell lysates of infected Vero cells were examined by immunoblotting with anti-SH as well as anti-NP and anti-P (FIG. 3D). SH was detected in MuV-IA and rMuV-infected cells, but not in rMuVΔSH-infected cells, confirming the lack of the SH protein expression in rMuVΔSH-infected cells.

Figure 4D:
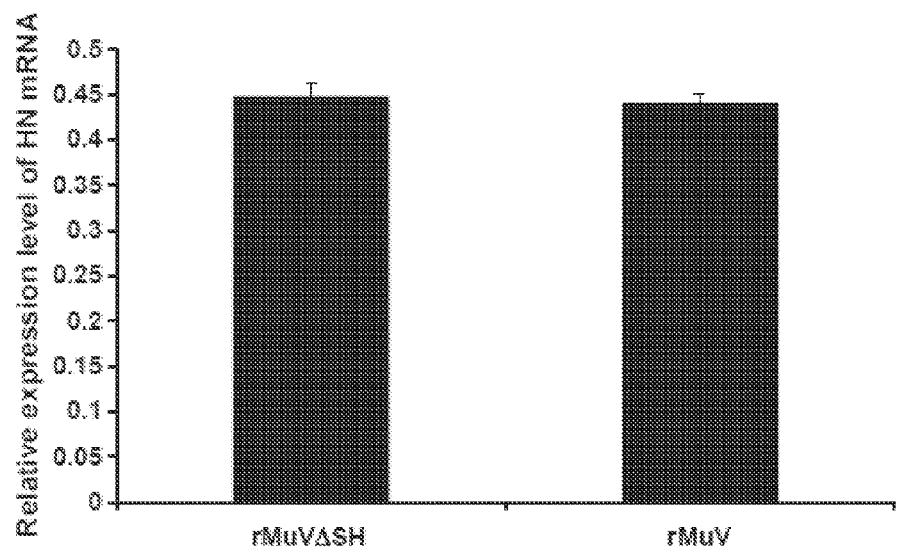
Figure 5A:
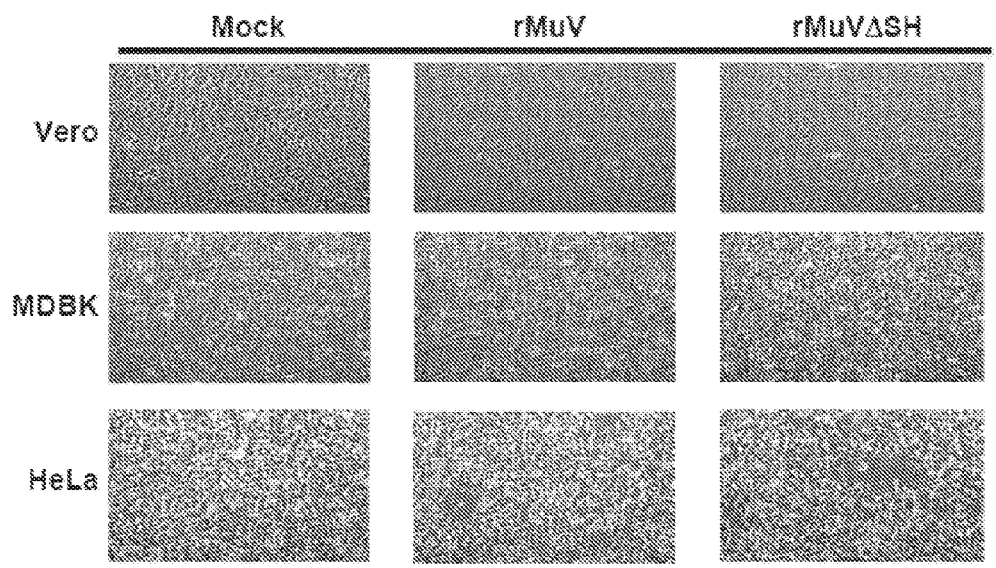

Analysis of rMuV and rMuVΔSH. To investigate the growth rate of rMuVΔSH, a multiple-cycle growth curve and protein expression levels were examined in Vero cells, and the titers of the viruses released from rMuVΔSH-infected Vero cells remained similar to rMuV-infected Vero cells at all time points (FIG. 4A). When the infected cells were lysed and viral protein expression levels were compared using Western blot, the protein levels of NP and P in rMuVΔSH and rMuV-infected cells were similar (FIG. 4B), indicating that the SH ORF was not essential for viral gene expression, or virus release in Vero cells, consistent with the previous findings. The HN gene is downstream of the SH gene. To examine whether there is any significant impact of the deletion of the SH ORF on the expression level of HN, expression levels of HN and NP of infected cells were examined using flow cytometry. As shown in FIG. 4C, relative expression level of HN in rMuV-infected cells and in rMuVΔSH-infected cells were similar, suggesting that the deletion of the SH ORF sequence did not affect expression of the HN protein. Furthermore, mRNA expression levels of HN were examined using real-time RT-PCR. No significant difference was observed between rMuV and rMuVΔSH (FIG. 4D). Interestingly, rMuVSH formed larger plaques in Vero cells compared to rMuV (FIG. 4A).

rMuVΔSH induced cytopathic effect in L929 cells. We compared infection of Vero, MDBK and HeLa cells with rMuVΔSH and rMuV. At one day post infection, there were no observable differences in rMuVΔSH- or rMuV-infected Vero and MDBK cells. Previous studies in our lab showed that the SH ORFs of PIV5 and RSV played a role in blocking TNF-α signaling. To test the hypothesis that mumps virus SH ORF has a role in regulating the TNF-α signaling pathway, the phenotype of rMuVΔSH in L929 cells, which undergo apoptosis after TNF-α treatment, was investigated. rMuVΔSH infection led to significantly more cell death than infections with rMuV or wtMuV. The phenotype was evident at 2-day post infection (FIG. 5B). To investigate whether the cytopathic effects (CPE) observed in rMuVΔSH infected L929 cells was caused by apoptosis, TUNEL assay was performed. At 1 dpi, infection with rMuVΔSH resulted in a higher percentage of infected cells with apoptosis than rMuV (FIG. 5C), indicating that the lack of SH led to increased apoptosis in infected cells.

Figure 6C:
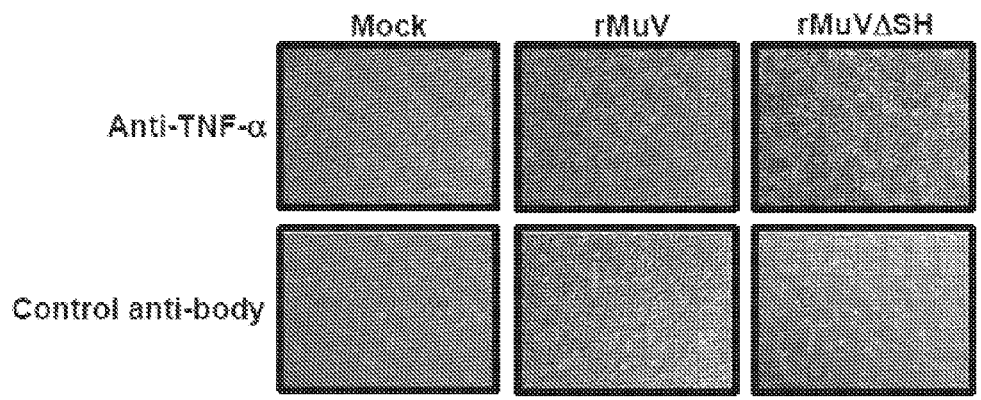
Figure 6D:
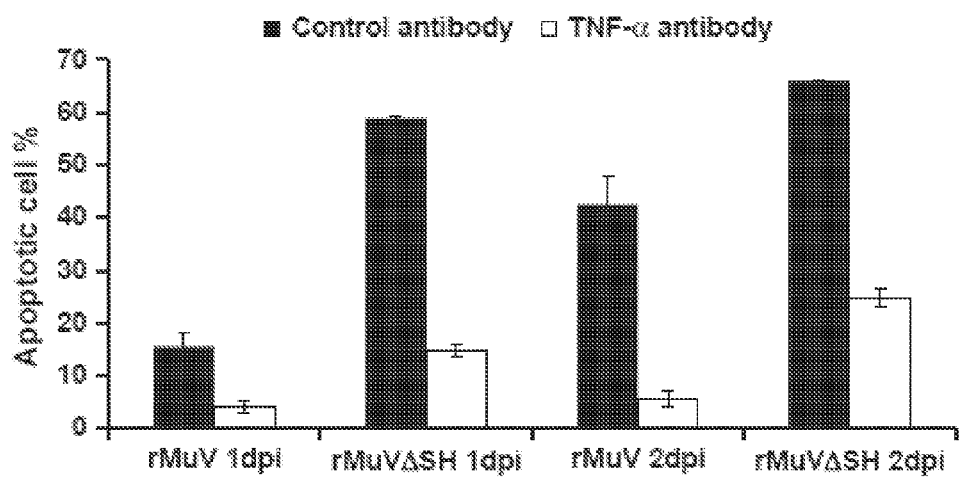

TNF-α played a critical role in rMuVΔSH-induced apoptosis. To test whether apoptosis in rMuVΔSH infected L929 cells resulted from an elevated TNF-α, the activation of NF-κB in rMuVΔSH-infected L929 cells was examined by examining nuclear translocation of p65, a key subunit of NF-κB. NF-κB factors are localized in the cytoplasm. On activation, for example by TNF-α stimulation, p65 is translocated into the nucleus (Baud and Karin, 2001, *Trends Cell Biol;* 11(9):372-377). A higher level of p65 nuclear localization was observed in rMuVΔSH-infected L929 cells (FIG. 6A), indicating activation of NF-κB. To investigate whether the production of TNF-α was increased in rMuVΔSH-infected cells, supernatants of infected were collected and levels of TNF-α were measured using ELISA. TNF-α production level was up regulated in rMuVΔSH-infected cells (FIG. 6B). To determine whether the increased TNF-α played a role in increased apoptosis in rMuVΔSH infected cells, the infected cells were treated with neutralizing antibody against TNF-α. Anti-TNF-α reduced CPE in rMuVΔSH infected cells, while the control antibody had no effect (FIG. 6C), indicating that TNF-α played a critical role in rMuVΔSH induced cell death. This was confirmed with TUNEL assay (FIG. 6D). At 1 dpi, with control antibody treatment, rMuVΔSH induced almost 4-fold higher apoptotic rate than rMuV. Treatment of anti-TNF-α antibody effectively blocked cell death in infected cells (FIGS. 6C, D).

Figure 7A:
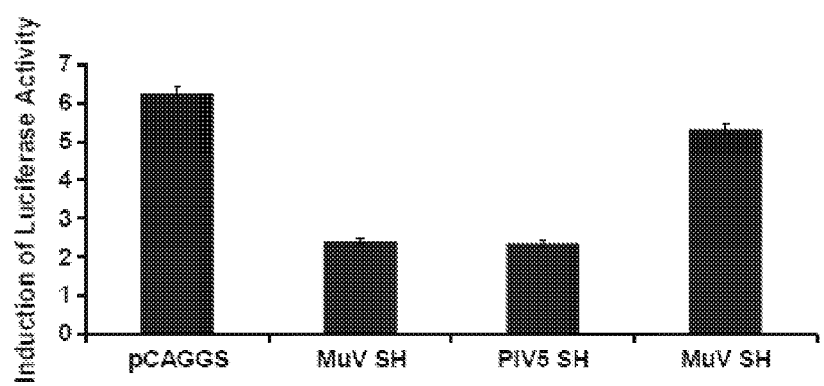
FIGS. 7A and 7B. MuV-IA SH inhibited TNF-α activation of NF-κB. L929 cells were transfected with a reporter plasmid (pκB-TATA-FL) and pCAGGS-MuV SH, pCA-GGS-PIV5 SH or pCAGGSMuV-NP (FIG. 7A). At one day post-transfection, cells were treated with TNF-α at 10 ng/ml for four hours and then assayed for fire fly luciferase activity. Similarly, the effect of the sequence of the SH ORF was examined using a plasmid encoding the SH ORF sequence without expressing the SH polypeptide due to in-frame stop codon insertion downstream of the start codon of the SH ORF (FIG. 7B).
Figure 7B:
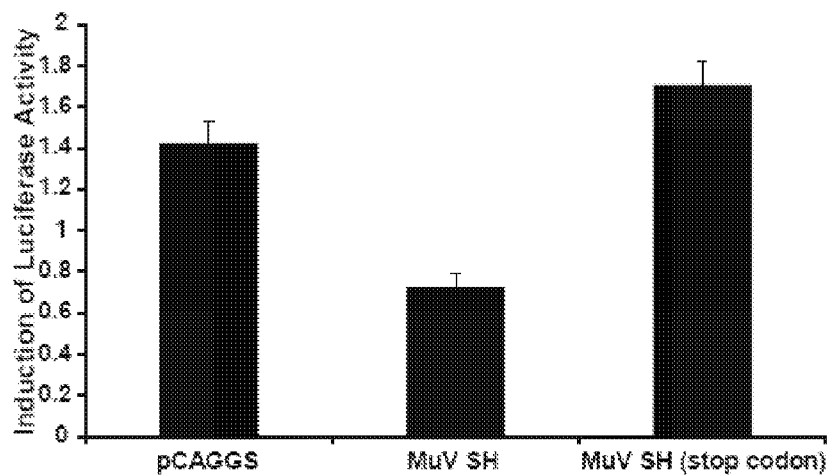

SH of MuV-IA blocked TNF-α signaling in vitro. To investigate whether MuV-IA SH expressed alone can block TNF-α signaling, a plasmid encoding SH of MuV-IA was co-transfected with a NF-κB promoter-luciferase reporter system into L929 cells. At one day post transfection, cells were treated with TNF-α. TNF-α signaling was blocked by SH of MuV-IA as well as SH of PIV5, but not by NP of MuV-IA (FIG. 7A) or the sequence of the SH ORF (FIG. 7B), indicating that the SH protein can block TNF-α-mediated signaling.

rMuVΔSH was attenuated in vivo. MuV is a human virus and there is no ideal animal model in which to study viral pathogenesis. Intracerebral injection of MuV into newborn rats has been used to compare the relative pathogenecities of different strains of MuV (Rubin et al., 2005). To compare the neurotoxicity of the viruses, rMuV or rMuVΔSH was injected intracerebrally into brains of newborn rats. Relative neurotoxicity score was calculated based on relative severity of hydrocephalus. As shown in FIG. 8, rMuVΔSH had a lower neurotoxicity score than rMuV, indicating that deletion of the SH ORF resulted in attenuation in vivo.

Discussion

Immunization against MuV is a part of a 2-dose MMR (mumps, measles and rubella) vaccine regimen that is administrated to children at 1 and 5 years of age in the U.S. Even with a two-dose vaccination schedule, large outbreaks have occurred in vaccinated populations. This example describes the rescue of a wild-type mumps virus that is representative of the strain associated with recent outbreaks in the U.S. and Europe. This example identifies the potential role of the SH protein in regulating TNF-α, and demonstrates that the deletion of the SH ORF resulted in attenuation in vivo, indicating that SH plays a role in viral pathogenesis. The attenuation of rMuVΔSH in vivo suggests that deleting the SH ORF can be a possible strategy to develop attenuated mumps strains. Recombinant MuVs expressing foreign genes such as GFP and RL have been obtained, and interestingly, the expression level of RL in rMuV-RL in Vero cells remained relatively high after 20 passages, indicating that MuV can possibly be used as a vector.

The SH protein of paramyxoviruses was first identified in PIV5-infected cells (Hiebert et al., 1985, *J Virol;* 55:744-751). A similar gene was predicted basing on sequence analysis of the Enders strain of MuV. However, due to a mutation in the intergenic sequence of the putative SH gene, the SH protein of the Enders strain MuV is not expressed in infected cells (Takeuchi et al., 1991, *Virology;* 181:364-366). Thus, the SH protein of MuV has never been detected in MuV-infected cells. Wilson et al. replaced the SH ORF within the genome of PIV5 with the SH ORF of MuV Enders strain and found that the MuV SH can functionally replace the SH ORF of PIV5 (Wilson et al., 2006, *J Virol;* 80(4):1700-09). Thus, it is thought that the function of MuV SH is the same as the function of the SH ORF of PIV5, a closely related paramyxovirus. In this example, the expression of SH was detected in MuV-infected cells for the first time, confirming the existence of the SH protein in MuV-infected cells. Furthermore, taking advantage of the new reverse genetics system, a recombinant MuV lacking the SH ORF (rMuVΔSH) was obtained and analyzed.

One interesting observation was that rMuVΔSH produced larger plaques. A possible explanation is that the deletion of the SH ORF resulted in a virus that promotes cell-to-cell fusion better than the wild type virus. Because there was no change of total number of ORFs or the overall order of genes, we expect that the relative amounts of viral mRNAs and the expression levels of viral proteins of rMuVΔSH should be similar to those of wild type virus (FIGS. 4B, 4C, and 4D). Thus, it is unlikely that the bigger plaque formation by rMuVΔSH was due to a higher level of viral protein expression. Further, a fusion assay using cells transfected with MuV HN and F was performed in the presence or absence of MuV SH, and no difference in the extent of cell-to-cell fusion was observed, suggesting that the SH does not have a role in promoting cell-to-cell fusion. It is possible that the larger plaques farmed by rMuΔSH are due to a higher level of induction of cell death by rMuVΔSH. The viruses infected cells at the same rate; however, the cells infected by rMuVΔSH induced more cell death than rMuV resulting in more rapid cell death at the edge of a plaque.

It is possible that the mRNA of from some ORFs may have biologic functions. For example, the mRNA of the L ORF of PIV5 is capable of activating IFN-β expression (Luthra et al., 2011, *Proc Natl Acad Sci USA;* 108(5):2118-2123). In this example, the ORF of SH was deleted, and the function of the polypeptide encoded by the SH ORF cannot be differentiated from SH mRNA itself. While the SH polypeptide was needed to block TNF-α mediated signaling, not the sequence of the SH ORF, and we favor a critical role of the SH polypeptide in mumps virus pathogenesis; however, it is possible that the small mRNA potentially expressed from the deleted SH gene could have contributed to the phenotype of rMuVΔSH. The reduced neurotoxicity of rMuVΔSH in neonatal rat brain indicates that the SH ORF plays a critical role in viral pathogenesis. We propose that infection with rMuVΔSH induced a higher level of proinflammatory cytokine expression, resulting in a more rapid resolution of infection, thus limiting damage in the infected brain.

Material and Methods

Plasmids, viruses and cells. All molecular cloning was conducted according to standard procedures as previously described (He et al., 1997, *Virology;* 237:249-260). MuV-IA NP, P and L genes were cloned into the pCAGGS expression vector (Niwa et al., 1991, *Gene;* 108:193-200). MuV-IA SH gene was cloned into the pCAGGS expression vector. MuV-IA SH (stop codon) was constructed by introducing three continues stop codon sequence into the SH ORF, six nucleotides downstream of the start codon. Construction of MuV-IA full-length cDNA in pUC19 was analogous to the PIV5 reverse genetics system (He et al., 1997, *Virology;* 237:249-260). To construct pMuVΔSH, the region of the SH ORF from the 4th amino acid to the 57th (156 nt) was substituted with a short six nucleotide sequence designed to facilitate subcloning and to maintain the length of the genome a multiple of six (known as the "rule of six"). pMuV-EGFP and pMuV-RL were constructed by inserting either an EGFP or a renilla luciferase gene between F and SH gene flanked by F gene start and SH gene end.

To rescue an infectious virus from cDNA, plasmid (5 μg) containing a full-length genome or a mutated MuV genome was co-transfected with plasmids pCAGGS-L (1 μg), pCA-GGS-NP (1.5 μg) and pCAGGS-P (200 ng) into BSRT-7 cells. Usually four to seven days post-transfection, syncytia formation could be observed in transfected BSRT-7 cells. Supernatants were plagued in Vero cells. Plaques could be visualized at 4 to 7 dpi. One or two plaques from each independent rescue were amplified in Vero cells and their genomes were sequenced.

Vero, HeLa, MDBK and L929 cells were maintained in Dulbecco's modified Eagle medium (DMEM) with 10% fetal bovine serum (FBS) and 1% penicillin-streptomycin (P/S) (Mediatech Inc., Holu Hill, Fla.), BSRT-7 cell were maintained in DMEM supplemented with 10% FBS, 1% P/S and 10% tryptose phosphate broth (TPB) plus G418 at 400 μg/ml. Cells were cultured at 37° C. with 5% $CO_2$ and passed the day before infection or transfection at appropriate dilution factors to archived 80.90% confluence the next day. For virus infection, cells were infected with viruses in DMEM plus 1% bovine serum albumin (BSA) at MOI of 0.01, 3 or 5 and incubated for 1 to 2 h at 37° C. with 5% $CO_2$. The culturing medium was then replaced with DMEM supplied with 2% FBS and 1% P/S. For transfection, cells were transfected with plasmids using PLUS™ and Lipofectamine™ reagents from Invitrogen following the manufacturer provided protocol.

MuV-IA (MuV/Iowa/US/2006) was isolated at the Iowa Hygenic Laboratory from a buccal swab obtained from a mumps case during the early phase of the outbreak in 2006. Genotype analysis was performed at the CDC (Rota et al., 2009, *J Med Virol;* 81(10):1819-1825) and the accession number for the SH sequence is DQ661745. All mumps viruses were grown in Vero cells and were harvested 4 to 7 dpi. Virus titers were measured in Vero cells by plaque assay followed by Giemsa staining as described before (He and Lamb, 1999, *J Virol;* 73:6228-6234; and He et al., 1997, *Virology;* 237:249-260).

Sequencing of viruses. Viral RNA was extracted from cell culture supernatants using QIAampR viral RNA extraction mini kit from QIAGEN following manufacturer's protocol. Isolated total RNA was reverse transcribed into cDNA using Super ScriptR III reverse transcriptase from Invitrogen with random hexamers. Synthesized cDNA was then served as templates for PCR using mumps virus genome specific primers (Table 1) and Taq polymerase from Invitrogen. Fifteen sets of primers (shown in Table 2), each contained a forward and a reverse primer, were designed as to divide the genome into fifteen overlapped fragments. The primers were used for the subsequent sequencing of the PCR products (Li et al., 2011, *J Virol;* 85(1):32-42). Leader and Trailer sequences were sequenced following standard protocol of Rapid Amplification of cDNA Ends (RACE) (Li et al., 2011, *J Virol;* 85(1):32-42).

Generation of monoclonal and polyclonal antibodies against mumps NP, P and SH. To generate monoclonal antibodies against MuV-IA, the virus was grown in Vero cells. The medium of infected Vero cells was collected, and clarified with low-speed centrifugation at 3 K rpm for 10 min. The clarified media containing virus was overlaid onto a 10 ml 20% sucrose solution and centrifuged at 40 K rpm for 1.5 h at 4° C. The pellet was resuspended in 0.5 ml 10×PBS, mixed with 1.3 ml 80% sucrose solution and overlaid by a decreasing sucrose gradient from bottom to top: 1.8 ml 50% sucrose solution and 0.6 ml 10% sucrose solution. The sucrose gradient with virus at the bottom was centrifuged at 45 K rpm for 3 hours (h) at 4° C. 1 ml fractions were collected, mixed with 10 ml 1×TEN buffer (100 mM NaCl, 10 mM Tris-base, 1 mM EDTA) and spun down at 40 K rpm for 1.5 h at 4° C. The pellet containing virus was suspended in 50 μl of 1×TEN buffer plus 1% NP-40 and used for generation of mouse hybridoma cells. Mouse hybridoma cells generating monoclonal antibodies against MuV-IA NP and P were engineered by the core facility in the Pennsylvania State University. The hybridomas were culture in D-MEM supplied with sodium pyruvate, with addition of 20% FBS and 0.1% Gentamicin at 37° C. with 5% $CO_2$.

To generate polyclonal antibodies against MuV-IA SH, two peptides (N-terminal MPAIQPPLYLTFLLC (SEQ ID NO:10) and C-terminal CYQRSFFHWSFDHSL (SEQ ID NO:11)) were purchased from GenScript Corporation. Two peptides (QFIKQDETGDLIETC (SEQ ID NO:12) and CSRPDNPRGGHRREW (SEQ ID NO:13)) were used to generate polyclonal antibodies against MuV-IA V (GenScript Corporation) in rabbits.

Treatment of infected cells with anti-TNF-α. L929 cells in six well plates were infected with rMuVΔSH or rMuV at a MOI of 5 and cultured in DMEM supplemented with 2% FBS and 1% P/S with neutralizing anti-TNF-α antibody or control antibody (BD Pharmingen) at 50 μg/ml for 1 or 2 days. At 1 day or 2 dpi, cells were photographed with a microscope with a digital camera, and then collected for MuV-NP staining or TUNEL assay.

Flow cytometry and TUNEL assay. Flow cytometry was performed as previously described (Timani et al., 2008, *J Virol;* 82(18):9123-9133). L929 cell in 6 well plates were infected with rMuVΔSH or rMuV or mock infected at MOI of 3 or 5. At 1 or 2 dpi, attached cells were trypsinized and combined with floating cells in the culture media. Cells were centrifuged and resuspended in 0.5% formaldehyde in phosphate buffered saline (PBS) for one hour at 4° C. The fixed cells were then washed with PBS, permeabilized in 50% FCS-50% DMEM plus three volumes of 70% ethanol overnight. Permeabilized cells were subjected for either TUNEL staining for apoptotic cells according to manufacturer's protocol or MuV-NP staining for infection rate. When cells were for NP staining, monoclonal MuV-NP antibody was diluted to 1:200 followed by PE anti-mouse secondary antibody staining at a dilution factor of 1:100.

Vero cells were mock infected or infected with rMuVΔSH or rMuV at a MOI of 0.5 or 0.01. At 24 or 48 hpi, attached cells were collected in combination with floating cells, fixed. For HN surface staining, cells were directly stained with anti-HN at a dilution factor of 1:50; for total staining of HN and NP staining, fixed cells were permeabilized with 0.1% saponin in PBS and stained with anti-NP at a dilution factor of 1:200 or anti-HN at a dilution factor of 1:50.

Assays for detection of activation of NF-κB. L929 cells on glass cover slips in six well plates were infected with rMuVΔSH, or rMuV at MOI of 0.01, or mock infected. At 2 dpi the cover slips were washed with PBS, and fixed in 0.5% formaldehyde. The fixed cells were permeabilized with PBS plus 0.1% saponine and then incubated with mouse anti-P65 (Santa Cruz Biotechnology) in PBS with 0.1% saponine followed by secondary FITC labeled goat antimouse antibody (Jackson Laboratory). The cells were photographed using a fluorescence microscope with a digital camera.

The NF-κB reporter assay system was performed as described previously (Wilson et al., 2006, *J Virol;* 80(4): 1700-09). L929 cells were plated into 24 well plates and transfected using PLUS™ and Lipofectamine™ reagents with either empty vector, pCAGGS-MuV SH, pCAGGS-MuV SH (stop), pCAGGS-PIV5 SH or pCAGGS-MuV NP, plus a picB-TATA-Luc (a reporter plasmid containing a NF-κB promoter region followed by TATA box enhancer and a firefly luciferase gene) and a pCAGGS-RL (a transfection control plasmid expressing renilla luciferase protein). On the second day post transfection, half of the cells were treated with TNF-α (Alexis, San Diego) at a concentration of 10 ng/ml in Optima (Invitrogen) for 4 h at 37° C. with 5% $CO_2$; half of the cells were treated with Optima only. Cells were then lysed with 100 μl 1× passive lysis buffer (Promega, Madison, Wis.) and 10 μl of the lysate were subjected for dual luciferase assay using a dual luciferase assay kit (Promega, Madison, Wis.). The ratio of TNF-α stimulated cells over no TNF-α stimulation is used as "induction of luciferase activity."

Immunoblotting. Vero cells in 6 well plates at about 90% confluence were infected with mock, MuV-IA, rMuV or rMuVΔSH at a MOI of 0.05. Cells were collected and lysed at 0 h, 24 h, 48 h, or 72 h post-infection in 0.5 ml WCEB buffer (50 mM Tris.HCl PH 8.0, 120 mM NaCl, 0.5% NP-40, 0.00076% EGTA, 0.2 mM EDTA, 10% Glycerol) with a mixture of protease inhibitors as described before (Luthra et al., 2008, *J Virol;* 82(21):10887-10895). Cell lysates were briefly centrifuged to remove cell debris. Cell lysates were loaded into 10% or 17.5% polyacrylamide gel and subjected for SDS-PAGE. Protein were transferred to Immobilon-FL transfer membrane (Millipore), incubated with primary antibody (anti-MuV SH 1:250, anti-MuV V 1:500, anti-MuV NP 1:5000, anti-MuV P 1:2000) and corresponding secondary antibodies conjugated to horseradish peroxidase, and detected by Amersham ECL™ western blotting detection kit (GE Healthcare).

Time course of rMuVΔSH, rMuV and MuV-IA infection in cell culture. Cells in 6 cm plates were infected with MuV-IA, rMuV, or rMuVΔSH at MOI of 0.01. 100 μl of supernatant were collected at 0 h, 24 h, 48 h, 72 h postinfection and frozen down at –80° C. supplemented with 1% BSA. Virus titers were determined by plaque assay using Vero cells in 24 well plates in triplicates. After one to two hours incubation with the viruses, growth media were changed into semisolid DMEM with 2% FBS, 1% P/S and 1% low melting point agarose. 4 to 7 dpi, 24 well plates of Vero cells were stained with Giemsa stain and plaques were counted.

Enzyme-linked immunosorbent assay (ELISA) of TNF-α. L929 cells in 6 well plates were infected with mock, rMuV or rMuVΔSH at MOI of 5. Culturing media were collected at 1 dpi, 2 dpi and 3 dpi. The amount of TNF-α secreted into the culturing media was measured using a murine TNF-α detection kit (Amersham Pharmacia) following the procedures described before (Li et al., 2011, *J Virol;* 85(1):32-42).

Real time RT-PCR. Vero cells were mock infected or infected with rMuVΔSH or rMuV at a MOI of 0.005. Viral RNA was extracted from infected cells at 4 dpi using QIAGEN RNeasymini kit and reverse transcribed into cDNA using Oligo-dT as primers. MuV F and HN mRNA specific FAM tagged probes were purchased from Applied Biosystems™. Real time PCR was assembled using Taq-Man® Gene Expression Master Mix, according to manufacturer's protocol. Ratio between HN mRNA verses F mRNA was calculated using Δct.

Examination of MuV neurotoxicity. The rat neurotoxicity test was performed as described before (Rubin et al., 2000, *J Virol;* 74:5382-5384). Newborn rats were inoculated intracerebrally with 100 pfu of rMuV (n=36), or rMuVΔSH (n=24) in 20 μl. EMEM. Animals were sacrificed at one month after injection and the brains were removed, immersion fixed and embedded in paraffin. One 10 μm sagittal section at a constant distance from the anatomical midline from each hemisphere of brain was selected, and stained with haematoxylin and eosin. The neurotoxicity score was calculated based on the cross-sectional area of the brain (excluding the cerebellum) as a percentage of the lateral ventricle on tissue sections from paired brain using Image-Pro Plus image analysis software (Media Cybernetics). The neurotoxicity score was defined as the mean ratio (percentage) of these two measurements on each of the two tissue sections per rat brain. Any rats with signs of pain or distress prior to the planned 1 month end point were humanely euthanized immediately and included in analyses. The NIH Guidelines for the Care and Use of Laboratory Animals were strictly adhered to throughout.

The results of this example can now also be found in Xu et al., "Rescue of wild-type mumps virus from a strain associated with recent outbreaks helps to define the role of the SH ORF in the pathogenesis of mumps virus," *Virology;* 417(1):126-36 (published Aug. 15, 2011; Epub 2011 Jun. 14).

Example 2

The V Protein of Mumps Virus Plays a Critical Role in Pathogenesis

Mumps virus (MuV) causes an acute infection in humans characterized by a wide array of symptoms ranging from relatively mild manifestations, such as parotitis, to more-severe complications, such as meningitis and encephalitis. Widespread mumps vaccination has reduced mumps incidence dramatically; however, outbreaks still occur in vaccinated populations. The V protein of MuV, when expressed in cell culture, blocks interferon (IFN) expression and signaling and interleukin-6 (IL-6) signaling. In this example, a recombinant MuV incapable of expressing the V protein (rMuVΔV) was generated. The rescued MuV was derived from a clinical wild-type isolate from a recent outbreak in the United States (MuV$^{Iowa/US/06}$, G genotype). Analysis of the virus confirmed the roles of V protein in blocking IFN expression and signaling and IL-6 signaling. It was also found that the rMuV$^{Iowa/US/06}$ΔV virus induced high levels of IL-6 expression in vitro, suggesting that V plays a role in reducing IL-6 expression. In vivo, the rMuV$^{Iowa/US/06}$ΔV virus was highly attenuated, indicating that the V protein plays an essential role in viral virulence.

The RNA genome of MuV is 15,384 nucleotides long. It encodes nine known viral proteins. The V protein of MuV has 224 amino acid residues and contains a cysteine (Cys)-rich C terminus that is conserved among all paramyxoviruses. The V protein interrupts the interferon (IFN) signaling pathway through degradation of STAT1, a critical transcription factor for IFN-activated gene expression (Kubota et al., 2002, *J Virol;* 76:12676-12682). A tryptophan-rich motif within the Cys-rich C terminus of the MuV V protein is essential in the ubiquitination and degradation of STAT1 (Kubota et al., 2002, *J Virol;* 76:12676-12682; Kubota et al., 2001, *Biochem Biophys Res Commun;* 283:255-259; and Nishio et al., 2002, *Virology;* 300:92) through the N-terminal region of STAT1 (Yokosawa et al., 2002, *J Virol;* 76:12683-12690). The V protein has also been demonstrated to associate with receptor-activated C kinase (RACK1), which contains Trp-Asp (WD) repeats and mediates interactions between the IFN receptor and STAT1. The V-RACK1 interaction results in the disassociation of STAT1 and RACK1, contributing to the blockade of IFN signaling by V protein (Kubota et al., 2002, *J Virol;* 76:12676-12682). This interaction may be important to block IFN signaling before the complete degradation of STAT1 occurs (Kubota et al., 2005, *J Virol;* 79:4451-4459). The V protein of MuV also interacts with MDA5, a RNA helicase that plays a critical role in the activation of IFN expression in infected cells (Andrejeva et al., 2004, *Proc Natl Acad Sci USA;* 101:17264-17269) and blocks the activation of IFN expression. The Cys-rich C terminus of V protein is essential for its interaction with MDA5 through its helicase C domain (Parisien et al., 2009, *J Virol;* 83:7252-7260; Ramachandran and Horvath, 2010, *J Virol;* 84:11152-11163). The V protein can serve as a substrate for inhibitor of κB kinase ε (IKKe)/tumor necrosis factor receptor associated factor (TRAF) family member-associated NF-κB activator (TANK)-binding kinase 1 (TBK1), resulting in inhibition of the activation of interferon regulatory factor 3 (IRF3). The interaction between V protein and TBK1/IKKe inhibits the activation of IRF3, a critical transcription factor for IFN expression, resulting in the blockade of IFN expression (Lu et al., 2008, *J Biol Chem;* 283:14269-14276). The V protein causes degradation of STAT3, a critical transcription factor for interleukin-6 (IL-6)-mediated signaling and oncogenesis (Ulane et al., 2003, *J Virol;* 77:6385-6393). A point mutation within the V protein (E to D at position 95) results in a V protein that is capable of STAT1 degradation without affecting its ability to target STAT3 for degradation. The ability of V protein to block IFN signaling is thought to be important for viral pathogenesis (Rosas-Murrieta et al., 2010, *Virol J;* 7:263). In this Example a recombinant MuV that it was no longer capable of expressing the V protein (rMuV$^{Iowa/US/06}$ΔV) was generated. The rescued MuV was derived from a clinical wild-type (WT) isolate from a recent outbreak in the United States (MuV$^{Iowa/US/06}$, G genotype). This is the first study of the functions of the V protein of MuV in the context of viral infection.

Materials and Methods

Plasmids, viruses, and cells. The MuV strain, MuV$^{Iowa/US/06}$, was obtained from a patient during the 2006 Midwest mumps outbreak in the United States. A full-length cDNA clone of the virus (pMuV$^{Iowa/US/06}$) was constructed as described in Example 1 (see also Xu et al., 2011, *Virology;* 417:126-136). This plasmid was modified to not express the V protein by changing the editing site of the P/V gene (GGGGGG; nucleotides 1-6 of SEQ ID NO:14) to GAGGAGGG (nucleotides 1-8 of SEQ ID NO:15) and the addition of another four base pairs (CTAG; nucleotides 3-6 of SEQ ID NO:16) to the 3' untranslated region (3' UTR; SEQ ID NO:16) of the gene to comply with "the rule of six" (Kolakofsky et al., 1998, *J Virol;* 72:891-899).

To rescue an infectious virus, plasmid pMuV$^{Iowa/US/06}$ (5 μg), along with plasmids pCAGGS-L (1 μg), pCAGGS-NP (1.5 μg), and pCAGGS-P (200 ng), were transfected into BSRT-7 cells. Three days later, transfected BSRT-7 cells were mixed with Vero cells at 1:1. Ten to 14 days later, when syncytium formation was observed, supernatants containing rMuV$^{Iowa/US/06}$ΔV were collected and plaque purified in Vero cells. Plaques (developing 4 to 7 days postinfection [dpi]) were amplified in Vero cells, and their genomes were sequenced. The rescue procedure was repeated to produce independent stocks of rMuV$^{Iowa/US/06}$ΔV.

Vero, HeLa, MDBK, and L929 cells were maintained in Dulbecco's modified Eagle medium (DMEM) with 10% fetal bovine serum (FBS) and 1% penicillin-streptomycin (P/S) (Mediatech Inc., Holu Hill, Fla.). BSRT-7 cells were maintained in DMEM supplemented with 10% FBS, 1% P/S, and 10% tryptose phosphate broth (TPB), plus 400 μg/ml Geneticin G418 antibiotic. Cells were cultured at 37° C. with 5% $CO_2$ and passaged the day before infection or transfection at appropriate dilution factors to achieve 80 to 90% confluence the next day. For virus infection, cells were inoculated with viruses in DMEM plus 1% bovine serum albumin (BSA) at a multiplicity of infection (MOI) of 0.01, 3, or 5 and incubated for 1 to 2 h at 37° C. with 5% $CO_2$. The inocula were then replaced with DMEM supplemented with 2% FBS and 1% P/S. Cells were transfected with plasmids using PLUS and Lipofectamine reagents (Invitrogen, Carlsbad, Calif.) following the manufacturer-provided protocols.

All mumps viruses were grown in Vero cells and were harvested at 4 to 7 dpi. Virus titers were measured in Vero cells by plaque assay as described previously (He and Lamb, 1999, *J Virol;* 73:6228-6234; He et al., 1997, *Virology;* 237:249-260). Parainfluenza virus 5 (PIV5) and recombinant PIV5 lacking the expression of the C terminus of the V protein (rPIV5VΔC) were grown as described before (He et al., 2002, *Virology;* 303:15-32).

Sequencing of viruses. Viral RNA was extracted from cell culture supernatants by using the QIAamp viral RNA extraction minikit (Qiagen Inc., Valencia, Calif.) following manufacturer's protocol. Isolated viral RNA was reverse transcribed into cDNA by using SuperScript III reverse transcriptase with random hexamers (Invitrogen). Synthesized cDNA then served as templates for PCR using mumps virus genome-specific primers (shown in Table 1) and Taq polymerase (Invitrogen). Fifteen sets of primers (shown in Table 2), each containing a forward and reverse primer, were designed to divide the genome into 15 overlapping fragments. The primers were then used for the subsequent sequencing of the PCR products (Li et al., 2006, *Virology;* 346:219-228). Leader and trailer sequences were sequenced following the standard protocol of rapid amplification of cDNA ends (RACE) (Li et al, 2011, *J Virol;* 85:32-42).

Flow cytometry and TUNEL assay. Flow cytometry was performed as previously described (Sun et al., *J Virol* 85:8376-85). HeLa or Vero cells in 6-well plates were mock infected or infected with $rMuV^{Iowa/US/06}ΔV$, $rMuV^{Iowa/US/06}$, or $MuV^{Iowa/US/06}$ at an MOI of 0.1 or 0.5. At 24 h postinfection (hpi), 48 hpi, 72 hpi, or 96 hpi, attached cells were trypsinized and combined with floating cells in the culture media. Cells were centrifuged and resuspended in 0.5% paraformaldehyde in phosphate-buffered saline (PBS) for 1 h at 4° C. The fixed cells were then washed with PBS and permeabilized in 50% fetal calf serum (FCS)-50% DMEM plus three volumes of 70% ethanol overnight. Permeabilized cells were subjected to either terminal deoxynucleotidyltransferase-mediated dUTP-biotin nick end labeling (TUNEL) staining or $MuV^{Iowa/US/06}$-NP, $MuV^{Iowa/US/06}$-P, or $MuV^{Iowa/US/06}$-HN staining for protein expression level. For NP staining, monoclonal $MuV^{Iowa/US/06}$-NP antibody was diluted 1:200; for P staining, monoclonal $MuV^{Iowa/US/06}$-P antibody (as described in Example 1; see also Xu et al., 2011, *Virology;* 417:126-136) was diluted 1:50 followed by fluorescein isothiocyanate (FITC) anti-mouse secondary antibody (Jackson ImmunoResearch) staining at a dilution of 1:10,000. For HN staining, polyclonal $MuV^{Iowa/US/06}$-HN was diluted 1:50 followed by FITC anti-rabbit secondary antibody staining at a dilution factor of 1:10,000. TUNEL staining was performed as described before following the manufacturer's protocol (Roche) (Sun et al., 2009, *PLoS Pathog;* 5:e1000525; Sun et al., 2004, *J Virol;* 78:5068-5078).

Immunoblotting. Vero cells in 6-well plates at approximately 90% confluence were mock infected or infected with $rMuV^{Iowa/US/06}$ or $rMuV^{Iowa/US/06}ΔV$ at an MOI of 0.01 or 0.5. Cells were lysed and collected at different time points postinfection in 0.5 ml WCEB buffer (50 mM Tris-HCl [pH 8.0], 120 mM NaCl, 0.5% NP-40, 0.00076% EGTA, 0.2 mM EDTA, 10% glycerol) with a mixture of protease inhibitors as described previously (Rubin et al., 2011, *Vaccine;* 29:2850-2855; Rubin et al., 2000, *J Virol;* 74:5382-5384). Cell lysates were briefly centrifuged to remove cell debris and loaded onto a 10% or 17.5% polyacrylamide gel and subjected to SDS-PAGE. Proteins were transferred to an Immobilon-FL transfer membrane (Millipore, Billerica, Mass.), incubated with primary antibody (anti-$MuV^{Iowa/US/06}$ V, 1:500; anti-$MuV^{Iowa/US/06}$ NP, 1:5,000; anti-$MuV^{Iowa/US/06}$ P, 1:2,000 [43], anti-STAT1, 1:200 (#B2410; Santa Cruz Biotechnology, Inc., Santa Cruz, Calif.); anti-STAT2, 1:200 (#07-224; Millipore, Billerica, Mass.); anti-STAT3, 1:200 (#F300; Santa Cruz Biotechnology, Inc., Santa Cruz, Calif.) and corresponding secondary antibodies conjugated to horseradish peroxidase, and detected using an Amersham ECL Western blotting detection kit (GE Healthcare Bioscience, Piscataway, N.J.).

Growth curve of $rMuV^{Iowa/US/06}ΔV$ and $rMuV^{Iowa/US/06}$. Cells in 6-cm plates or 6-well plates were infected with rMuVΔV or rMuV at an MOI of 0.01. One milliliter (6-cm plates) or 100 μl (6-well plates) of supernatant were collected at 0 h, 24 h, 48 h, and 72 h (24 h, 48 h, 72 h, 120 h, 168 h, 216 h, and 264 h in HeLa) postinfection, supplemented with 1% BSA, and stored at 80° C. Virus titers were determined by plaque assay using Vero cells in 6-well plates in triplicate. After one to two hour (h) incubations with the viruses, the growth medium was changed to DMEM with 2% FBS, 1% P/S, and 1% low-melting-point agarose. Four to 7 dpi, 6-well plates of Vero cells were stained with Giemsa stain, and plaques were counted.

ELISA for IFN-β and IL-6. HeLa cells or 293T cells were mock infected or infected with PIV5-WT (MOI 5), rPIV5-VΔC (MOI-5), $rMuV^{Iowa/US/06}$ (MOI 0.5), or $rMuV^{Iowa/US/06}ΔV$ (MOI 0.5) virus in 12-well plates. The supernatants were collected at 24 h and 48 h postinfection. The amount of secreted IL-6 in the medium was measured using the OptEIA human IL-6 enzyme-linked immunosorbent assay (ELISA) kit (BD Biosciences, San Jose, Calif.), and IFN-β was measured using the VeriKine human IFN-β ELISA kit as described before (16, 18) (PBL Interferon-Source, Piscataway, N.J.) according to the manufacturer's instructions.

Neurotoxicity test. The neurovirulence phenotype of the rescued viruses was assessed by measuring the extent of MuV-induced hydrocephalus, the major neuropathologic outcome of MuV infection in rats, as previously described (Rubin et al., 2000, *J Virol;* 74:5382-5384). Briefly, three litters of 8 to 10 newborn Lewis rats were inoculated intracerebrally with 10 μl of DMEM containing 100 PFU of each of the two virus stocks rescued from plasmid $pMuV^{Iowa/US/06}$ and each of the two virus stocks rescued from plasmid $pMuV^{Iowa/US/06}ΔV$. On day 30 postinoculation, the rats were humanely sacrificed by $CO_2$ asphyxiation following the NIH Guidelines for the Care and Use of Laboratory Animals. Brains were removed and immersion fixed in 10% neutral-buffered formalin at 4° C. for 4 to 5 days, followed by paraffin embedding. Sagittal sections obtained at a standard distance from either side of the rostral-caudal midline were stained with hematoxylin and eosin.

The neurovirulence score was determined by calculating the ratio between the cross-sectional area of the brain (excluding the cerebellum) and the cross-sectional area of the lateral ventricle (which is enlarged following infection with neurovirulent MuV strains), measured using Image Pro Plus image analysis software (Media Cybernetics, Silver Spring, Md.). The mean ratio (given in percent) of these two measurements on each of the two tissue sections per rat brain is the neurovirulence score for that particular brain. The neurovirulence score for each virus is the mean neurovirulence score for all brains within the treatment group. All comparisons were made using at test or, with nonnormal data (failed Shapiro-Wilk test), the Mann-Whitney rank sum test (α=0.05).

Results

Recovery of a recombinant MuV lacking expression of V protein (rMuVΔV). To investigate the role of the V protein in viral pathogenesis in the context of viral infection, we constructed a cDNA of the MuV$^{Iowa/US/06}$ genome containing mutations to ablate the V protein expression (pMuV$^{Iowa/US/06}$ΔV) (the accession number for MuV$^{Iowa/US/06}$ genome is JN012242) (Xu et al., 2011, *Virology;* 417:126-136). Ablation of the V protein expression from the genome was achieved by changing the editing site (GGGGGG; nucleotides 1-6 of SEQ ID NO:14) in the P/V gene into GAGGAGGG (nucleotides 1-8 of SEQ ID NO:15). Therefore, only a transcript encoding the P protein is generated from P/V gene transcription (FIG. 9A). Infectious viruses abolishing the expression of the V protein (rMuV$^{Iowa/US/06}$ΔV) were rescued from the cloned DNA through transfection of pMuV$^{Iowa/US/06}$ΔV into BSRT-7 cells. Rescued viruses were further plaque purified and amplified in Vero cells. To confirm the presence of the genetic changes to shut off the V protein expression in the rescued virus genome, viral RNAs were extracted from virus stocks and reverse transcribed into cDNA for sequencing (FIGS. 9B and 9C).

Sequencing of the genome of the rescued virus revealed the presence of nucleotide substitutions in the NP gene end (GE) sequence and at the P/V gene start (GS) sequence comparing to input cDNA sequence as well as the changes that would ablate the expression of the V protein (FIG. 9C). Immunoblotting of infected cells was performed to confirm the absence of the V protein expression in rMuV$^{Iowa/US/06}$ΔV-infected Vero cells (FIG. 9D). To further investigate, the virus was rescued from the cDNA plasmid seven more times (FIG. 10A). Viruses from seven out of the total eight rescued viruses contained a point mutation at either the NP GE (six) or P/V GS region (one), while one contained a point mutation in the L gene (FIG. 10B). All of the rescued rMuV$^{Iowa/US/06}$ΔV viruses contained at least one point mutation in their genome, and the most frequent point mutation was at position 1899 in the genome; thus, this virus was used as a representative virus and designated as rMuV$^{Iowa/US/06}$ΔV for this work, unless otherwise noted.

Analysis of rMuVΔV in tissue culture cell lines. To analyze the growth rate of rMuV$^{Iowa/US/06}$ΔV in cell lines, Vero cells or HeLa cells were infected with rMuV$^{Iowa/US/06}$ΔV or rMuV$^{Iowa/US/06}$ at an MOI of 0.01, medium was collected at multiple time points postinfection, and viral titers were determined using plaque assay (FIG. 11A). rMuV$^{Iowa/US/06}$ΔV grew at a rate comparable to that of rMuV$^{Iowa/US/06}$V in Vero cells during the first 48 h postinfection (hpi), and then the growth of rMuV$^{Iowa/US/06}$ΔV decreased and remained approximately 1 log lower in titer than rMuV$^{Iowa/US/06}$ throughout the studied time course (FIG. 11A). Plaque size of rMuV$^{Iowa/US/06}$ΔV in Vero cells showed no significant differences from that of rMuV$^{Iowa/US/06}$ (FIG. 11B). Protein expression levels of rMuV$^{Iowa/US/06}$ΔV or rMuV$^{Iowa/US/06}$ low-MOI-infected Vero cells were examined by immunoblotting with anti-NP, P, and V or anti-β-actin (FIG. 11C). Consistent with the time course, the viral protein expression levels of rMuV$^{Iowa/US/06}$ΔV were similar to those of rMuV$^{Iowa/US/06}$ at 48, 72, and 96 hpi (adjusting for the levels of β-actin). In HeLa cells, the growth of rMuV$^{Iowa/US/06}$ΔV was reduced (FIG. 11D). The absence of a functional V protein reduced the virus titer of rMuV$^{Iowa/US/06}$ΔV by almost 2 $\log_{10}$ from 72 hpi to 168 hpi compared with rMuV$^{Iowa/US/06}$. Nevertheless, the both viruses reached similar titers at later time points.

Expression of viral genes in rMuV$^{Iowa/US/06}$ΔV-infected cells. Mutations at either the NP GE or P/V GS in recovered rMuV$^{Iowa/US/06}$ΔV viruses suggested that a modulation of viral protein expression levels between NP and P might be critical for the recovery of rMuV$^{Iowa/US/06}$ΔV from cDNA. To investigate the viral protein expression pattern in rMuV$^{Iowa/US/06}$ΔV, Vero cells infected with a high MOI were stained for NP and P proteins at different time points postinfection and assessed by flow cytometry (FIG. 12). To quantify the possible changes in the NP and P expression pattern, P protein expression levels were normalized to that of the corresponding NP levels (FIGS. 12A and 12B). The P/NP ratio of rMuVΔV was significantly higher than that of rMuV at 12, 16, 24, and 48 hpi, indicating an elevated P protein expression in the rMuV$^{Iowa/US/06}$ΔV virus. This difference was no longer evident by 72 hpi.

Figure 12C:
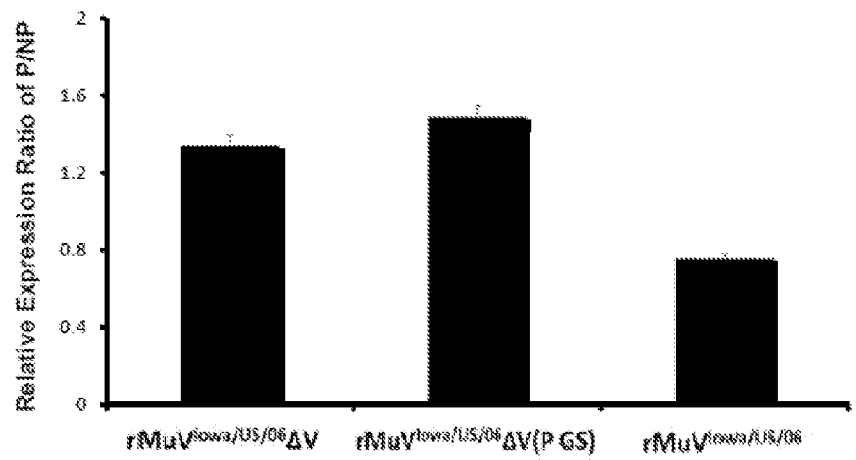
Figure 12D:
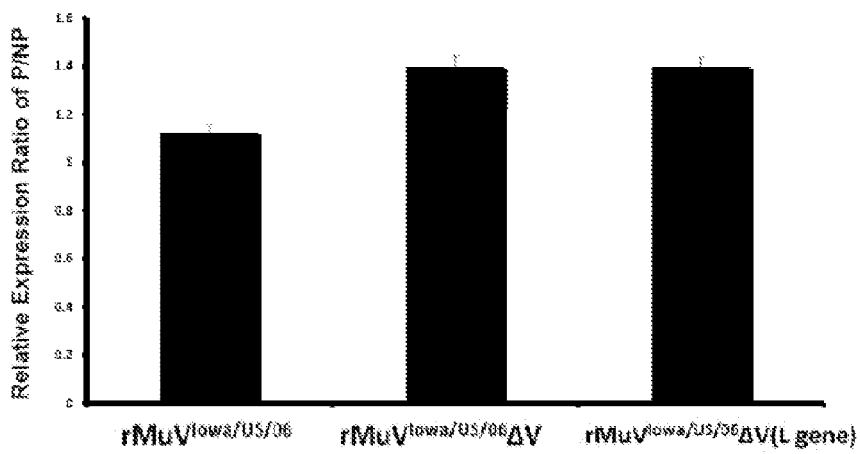

To investigate if this altered NP and P expression pattern was unique for this rMuV$^{Iowa/US/06}$ΔV strain, an rMuV$^{Iowa/US/06}$ΔV containing a P GS mutation (rMuV$^{Iowa/US/06}$ΔV [P GS]) and an rMuV$^{Iowa/US/06}$ΔV containing a L open reading frame (ORF) mutation (rMuV$^{Iowa/US/06}$ΔV [L gene]) were also examined (FIGS. 12C and 12D). Similar to rMuV$^{Iowa/US/06}$ΔV, both rMuV$^{Iowa/US/06}$ΔV (PGS) and rMuV$^{Iowa/US/06}$ΔV (L gene) had a P protein expression level greater than that of rMuV$^{Iowa/US/06}$, suggesting that this altered NP and P expression pattern was typical for the recovered rMuV$^{Iowa/US/06}$ΔV viruses.

Figure 14B:
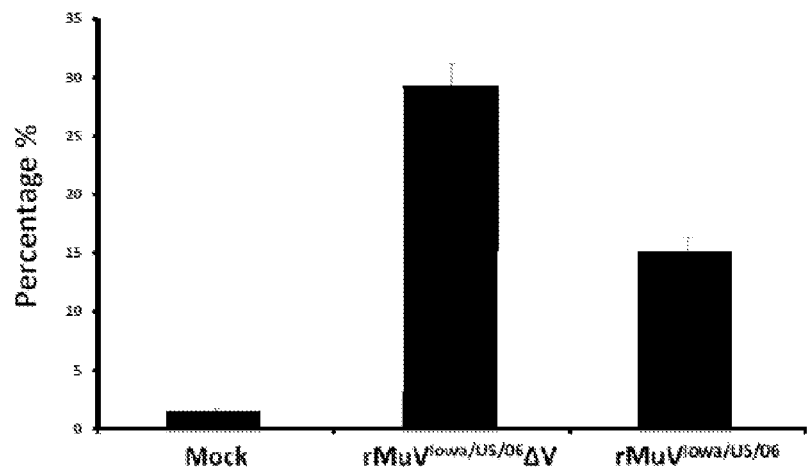
Figure 14C:
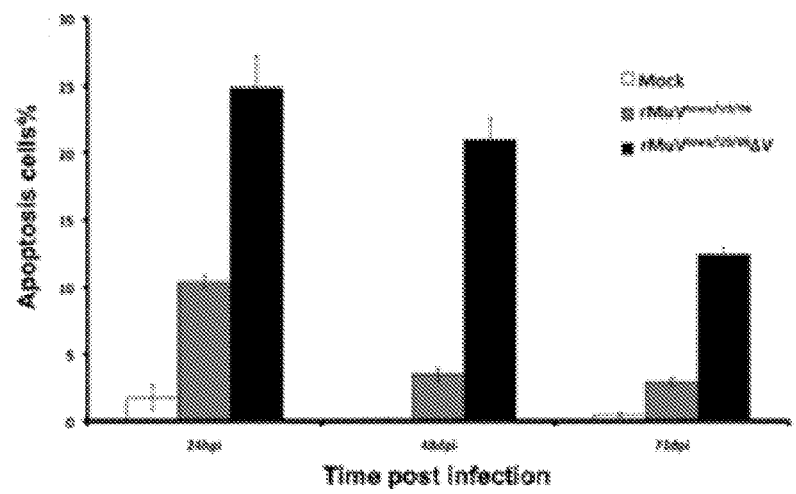

To examine if downstream viral protein expression was affected by either deletion of the V protein or the point mutation in NP GE, HN expression levels were examined using flow cytometry. Vero cells were either mock infected or infected with rMuV$^{Iowa/US/06}$ΔV or rMuV$^{Iowa/US/06}$ at an MOI of 0.5, and then cells were collected at 24 hpi and subjected to NP and HN staining (FIG. 13). No significant changes in the HN-to-NP ratio were observed.

rMuV$^{Iowa/US/06}$ΔV-induced accelerated CPE in tissue culture cell lines. rMuV$^{Iowa/US/06}$ΔV-induced cytopathic effects (CPE) were compared in three different cell culture lines from three different organisms. HeLa (human), Vero (monkey), and MDBK (bovine) cells were infected with rMuV$^{Iowa/US/06}$ΔV or rMuV$^{Iowa/US/06}$ at an MOI of 0.5, and the cells were photographed at 72 hpi. rMuV$^{Iowa/US/06}$ΔV caused the most-severe CPE in HeLa cells. More and larger syncytia were observed in rMuV$^{Iowa/US/06}$ΔV-infected HeLa cells, which may be a major contributing factor to cell death (FIG. 14A). To examine whether the cell death was caused by apoptosis, the TUNEL assay was performed (FIG. 14B). HeLa cells infected with rMuV$^{Iowa/US/06}$ΔV at an MOI of 0.5 showed at least a 2-fold higher level of apoptosis than cells infected with rMuV. Similarly, rMuV$^{Iowa/US/06}$ΔV induced a higher level of apoptosis in Vero cells (FIG. 14C). That the lack of V led to an increase in apoptosis in infected cells suggests that the V protein might play a role in blocking induction of apoptosis in infected cells.

Status of STAT proteins in MuV$^{Iowa/US/06}$-infected cells. Previous studies have shown that the V protein is involved in blocking the IFN signaling pathway by targeting STAT proteins for degradation. To determine whether MuV$^{Iowa/US/06}$V protein is the only virus-encoding antagonist of the IFN pathway, STAT family protein levels were examined in Vero cells infected with rMuV$^{Iowa/US/06}$ΔV or rMuV$^{Iowa/US/06}$ (FIGS. 15A and 15B). Consistent with previous in vitro transfection studies, STAT1 and STAT3, but not STAT2, were completely degraded in rMuV$^{Iowa/US/06}$-infected Vero cells, while rMuV$^{Iowa/US/06}$ΔV, which lacks expression of the V protein, failed to target any STAT proteins for degradation, indicating that the V protein might be essential and necessary for STAT protein degradation by MuV$^{Iowa/US/06}$. There is a time lag between the occurrence of a detectable V protein and the degradation of STAT protein (FIGS. 15A and 15B), implying that the degradation of STATs might require accumulation of the V protein.

PIV5, a paramyxovirus closely related to MuV, prevents induction of IFN-β in infected cells, while recombinant PIV5 lacking the expression of the conserved C terminus of the V protein does not (He et al., 2002, Virology; 303:15-32; Poole et al., 2002, Virology; 303:33-46). To compare IFN-β inductions by rMuV$^{Iowa/US/06}$ΔV and rMuV$^{Iowa/US/06}$, IFN-β concentration in the medium of infected 293T cells was measured by using ELISA. At 48 hpi, rMuV$^{Iowa/US/06}$ΔV induced IFN-β production higher than that induced by rMuV$^{Iowa/US/06}$ (FIG. 16A), indicating that the V protein of MuV$^{Iowa/US/06}$ plays a role in limiting IFN-β expression.

rMuV$^{Iowa/US/06}$ΔV led to a higher level of IL-6 induction. To investigate whether the absence of a functional V protein in MuV$^{Iowa/US/06}$ infection would lead to induction of other cytokines, IL-6 production levels in the medium of rMuV$^{Iowa/US/06}$ΔV and rMuV$^{Iowa/US/06}$-infected cells were examined. At 48 hpi, rMuV$^{Iowa/US/06}$ΔV led to a higher level of IL-6 production than rMuV$^{Iowa/US/06}$ in HeLa cells (FIG. 16B), indicating that IL-6 induction was reduced by the presence of the V protein. Intriguingly, rMuV$^{Iowa/US/06}$ infection also induced a significant amount of IL-6 production. This is consistent with MuV being an inflammatory disease.

Neurotoxicity of rMuV$^{Iowa/US/06}$ΔV. To examine the effect of the V protein on virus neurovirulence, viruses from two independent rescues using plasmid pMuV$^{Iowa/US/06}$ΔV (rMuV$^{Iowa/US/06}$ΔV) (FIG. 10A) were tested in rats, along with rMuV$^{Iowa/US/06}$ and the highly attenuated Jeryl Lynn (JL) vaccine virus as controls. As shown in FIG. 17, the ΔV viruses were highly attenuated compared to rMuV$^{Iowa/US/06}$ and JL vaccine virus.

Discussion

The results of this example confirm these findings through the study of a recombinant virus derived from a clinical isolate (genotype G) ablating the expression the V protein in the context of in vitro infection.

The lack of V protein expression also led to the induction of a higher level of IL-6, a proinflammatory cytokine, suggesting that the V protein plays a role in suppressing IL-6 expression. The lack of V protein expression in infected cells likely resulted in the attenuation of this strain in an animal model, suggesting that the V protein plays an essential role in viral virulence. It is possible that the inability of rMuV$^{Iowa/US/06}$ΔV to counter IFN action limited the replication of the virus in vivo, and the induction of a higher level of IL-6 by rMuV$^{Iowa/US/06}$ΔV attracted monocytes to clear the infection quickly, resulting in the attenuation of rMuV$^{Iowa/US/06}$ΔV in vivo.

Genetically, the closest virus to MuV is parainfluenza virus 5 (PIV5). The V proteins of MuV and PIV5 share many identical functions, including blocking IFN expression through MDA5, blocking IFN signaling through degradation of STAT1, and inhibiting expression of IL-6 in virus-infected cells. Interestingly, a recombinant PIV5 lacking the entire V protein has never been obtained in tissue culture cells, suggesting that the V protein of PIV5 plays a more critical role in virus replication (Dillon and Parks, 2007, J Virol 81:11116-11127; He et al., 2002, Virology; 303:15-32) than the V protein does for MuV. The viability of rMuV$^{Iowa/US/06}$ΔV suggests that the role of MuV$^{Iowa/US/06}$ V protein in virus replication is dispensable, at least in tissue culture cells.

In this example, a recombinant virus incapable of producing the V protein (rMuV$^{Iowa/US/06}$ΔV) was generated using a reverse genetics system for MuV based on a clinical isolate from a recent outbreak. This virus grew to titers similar to those for wild-type virus in Vero cells, a cell line that is used for vaccine production, as well as in other cell types. Most importantly, the virus exhibited low neurotoxicity in rats, supporting it as a vaccine candidate.

The V/P gene of MuV encodes three proteins, V, I, and P, through a process of "RNA editing," in which nontemplate G residues are inserted into mRNA during transcription at a specific site to generate mRNAs that can be translated into three different ORFs (Saito et al., 1996, Microbiol Immunol; 40:271-275). The V protein is translated from the "unedited" copy of mRNA, P from the mRNA with two G residue insertions, and the I protein from the mRNA with one or four G residue insertions. All of these proteins have identical N termini of 155 amino acid residues. The P protein has 391 amino acid residues and plays an essential role in viral RNA synthesis. The I protein has 170 amino acid residues, and its function is unclear. It is possible that the I mRNA is a by-product of RNA editing and it may not have any significant functions. The strategy we used to generate rMuV$^{Iowa/US/06}$ΔV also eliminated expression of the I protein. Because the mRNA for 1 counts only for less than 2% of total V, I, and P transcripts, and its sequence is very similar to the N termini of V and P (I has about 170 amino acid residues and 155 of them are identical to the N termini of V and P) (Paterson and Lamb, 1990, J Virol; 64:4137-4145; Takeuchi et al., 1990, Virology; 178:247-253), the phenotypes of rMuV$^{Iowa/US/06}$ΔV is attributed to the lack of V protein. However, a possible role for the I protein cannot be excluded.

All changes except the one in the L gene occurred in the gene junction between NP and P/P genes to generate viable infectious MuV incapable of expressing the V protein. It is interesting that a mutation in the L gene was able to allow the rescue of a virus lacking the V protein. While the possibility that the mutation in the L gene occurred fortuitously cannot be excluded and is immaterial to the function of L, one can speculate that the particular mutation may play a role in modulating interactions between NP-P and L, considering that all other viruses rescued had mutations to modulate the levels of NP and P. Further analysis of the virus may lead to a better understanding of the function of L.

The results of this example can now also be found in Xu et al., "The v protein of mumps virus plays a critical role in pathogenesis," J Virol; 86(3):1768-76 (February 2012; Epub 2011 Nov. 16).

Example 3

Immunogenicity of MuVΔSH and MuVΔV in Mice

The immunogenicity of rMuVΔSH and rMuVΔV in mice was determined and MuV-specific immune responses measured. Mice in a group of 10 were inoculated with PBS, or $10^6$ pfu of MuV, rMuVΔV or rMuVΔSH intranasally. At 21 days post inoculation, blood samples from the mice were collected. Titers of anti-MuV antibodies in the sera were measured using ELISA. The 96-well plates for ELISA were coated with purified MuV virion. P values for MuV and rMuVΔSH, MuV and MuVΔV at highest dilution and lowest dilution of sera were lower than 0.05. The results are shown in FIG. 18.

Further humoral immunity (antibody) analysis will include a determination of anti-MuV antibodies in bronchoalveolar lavage (BAL), as measured by MuV-specific ELISA. In ELISA assays, the isotypes (IgA, IgG1, IgG2a, IgG2b, and IgG3) of the antibodies will also be determined using appropriate secondary antibodies. MuV-specific antibody titers will also be measured by virus. Neutralization assays against heterogonous JL or homologous MuV-IA will be performed on serum and BAL wash samples.

Cell mediated immunity (T cell) may be measured by antigen-specific IFNγ production. Specifically, lymphocytes from the BAL, spleen and/or draining lymph node will be assayed for MuV-specific T cell responses by restimulation with MuV-infected APCs or with purified MuV virions that are disrupted with mild detergent. IFN-γ responses will be determined by intracellular cytokine staining and/or ELISPOT assays.

Since the site of induction of immune responses can alter the nature of the immune response and dramatically impact protective efficacy, local and systemic immunity to MuV will be measured at various time points after immunization. Intranasal (IN) MuV immunization has the potential to induce local MuV-specific T cell and immunoglobulin responses that mediate protection against MuV challenge. Local (i.e. lung) MuV-specific immune responses will be assessed by analysis of BAL samples collected at time points after immunization or challenge. Infiltrating lymphocyte populations will be collected by centrifugation and the bronchoalveolar lavage (BAL) will be analyzed for mucosal Ig. Systemic responses will be assessed by analysis of serum antibody and splenic or mediastinal lymph node (MLN) lymphocytes.

Current MMR vaccination regimen calls for two-dose intramuscular (IM) inoculation. A similar regimen was used in a mouse model to evaluate efficacies of vaccines (Cusi et al., 2001, *Arch Virol;* 146(7):1241-1248). Initially, immunogenicity may be assayed using such a two dose/IM regiment. The mice will be injected with a primary dose and followed by an injection at two weeks after initial injection. At one month after last immunization, the mice will be sacrificed for immunological assays as described above. This experiment will generate a baseline of immune responses after inoculation with the vaccine candidates, along with the JL vaccine in our hand.

The immunogenicity of a rMuV vaccine construct as described herein may be examined using a two-dose/intranasal (IN) protocol. Both humoral and cell-mediated immune responses will be measured. It has been reported that the IN route generated better immune responses for some vaccines, including a robust cell mediated immune responses. In addition, IN inoculation has the benefit of generating mucosal immune responses and higher titers of IgA. Because of the success of using the IN route for influenza virus vaccination, the IN route will be feasible route for the new vaccine to be introduced to a large human population.

In a similar fashion, a three-dose inoculation regimen will also be tested. As the most likely target for initial Phase I clinical trials will be healthy individual who have already been vaccinated with two-dose MMR, the immune responses after two dose/IM inoculation with the JL vaccine followed by a third dose of JL (as a control) or a third dose of MuV vaccine either by IM or IN will be examined. If a MuV vaccine construct as described herein used as a boost (third dose) is safe and generates robust anti-genotype G immune responses, it may be used to replace the second dose of MMR and may eventually replace JL in the two-dose MMR.

The immunogenicity of any of the rMuV constructs described herein may be assayed in mice, as described in this example. Similar immunogenicity and efficacy studies may also be undertaken in additional animal model systems, including, but not limited to, ferret and non-human primate model systems.

Example 4

Generation and Analysis of rMuVΔSHΔV

Because MuV vaccine is used in 1-year old infants, safety is a paramount consideration in developing a new vaccine. While both rMuVΔSH and rMuVΔV demonstrate attenuation in a rat brain-based neurotoxicity test, to further reduce any potential risk, a recombinant virus lacking both SH and V (rMuVΔSHΔV) was generated using the reverse genetics system.

Briefly, following protocols described in more detail in Example 1 (see, for example, FIG. 3A), the ablation of SH protein expression from the MuVΔSHΔV genome was achieved by deleting 156 nucleotides in the SH gene open reading frame (ORF) of the SH gene from pMuV-IA. And, following protocols described in more detail in Example 2 (see, for example, FIG. 9A), the ablation of the V protein expression from the MuVΔSHΔV genome was achieved by changing the editing site (GGGGGG) in the P/V gene into GAGGAGGG. Therefore, only a transcript encoding the P protein is generated from P/V gene transcription. Infectious viruses abolishing the expression of both the SH protein and the V protein (rMuVΔSHΔV) were rescued from the cloned DNA through transfection of pMuVΔSHΔV into BSRT-7 cells. Rescued viruses were further plaque purified and amplified in Vero cells. To confirm the presence of the genetic changes to shut off both SH and V protein expression in the rescued virus rMuVΔSHΔV genome, viral RNAs were extracted from virus stocks, reverse transcribed into cDNA, and sequenced.

Following procedures described in more detail in Example 1 and Example 2, immunoblotting of infected cells will be performed to confirm the absence of SH and V protein expression in rMuVΔSHΔV-infected cells. The expression, function, immunogenicity, and pathogenicity of rMuVΔSHΔV will be analyzed by a variety of methods, including, but not limited to, any of those described herein, for example, as described in the Examples included herewith. Studies may include examination of the neurotoxicity of rMuVΔSHΔV in the neonatal rat brain and examination of immunogenicity in mice.

Example 5

Improving Recombinant MuV as a Vaccine Candidate

In this example, rMuV constructs will be further mutated using the reverse genetics system to introduce mutations at desirable locations. The resultant MuV mutants will be analyzed in tissue culture cells. Neurotoxicity will be evaluated in a rat model and immunogenicity of the viruses examined in mice, ferrets, and primates. It is likely that rMuV lacking the V and SH plus additional point mutations will be the most attenuated and the least likely to be reverted.

Generation and analysis of additional MuV mutants. The closest virus to MuV is parainfluenza virus 5 (PIV5). These two viruses have identical number of genes and gene order. In recent studies of PIV5, residues within PIV5 proteins have been identified that are capable of enhancing viral gene expression and inducing expression of cytokines such as type I interferon (Sun et al., 2009, PLoS Pathog; 5(7): e1000525). It was found that the residue of S157 of the P protein of PIV5 is a binding site for host kinase PLK1 and the residue of 5308 of the P protein of PIV5 is a phosphorylation site of PLK1. Mutating S157 or 5308 to amino acid residue A, results in a virus that increases viral gene expression as well as induction of interferon-β expression. Increasing viral gene expression will potentially increase immune responses because of increased amount of antigens and increasing IFN expression will likely cause attenuation because of anti-viral effects of IFN. Corresponding residues within the P protein of MuV are T147 and S307. These residues will be mutated and the impact of changing these residues on viral gene expression and induction of interferon will be examined.

Generation and analysis of rMuV lacking I and rMuVΔV expressing I. The strategy used in Example 2 to generate rMuVΔV also eliminated expression of the I protein besides the expression of V. The I protein is an editing product of VI//P gene. Its function is not known. Because its expression level is very low compare with V or P, and its sequence is very similar to the N-terminal of V and P (I has about 170 amino acid residues and 155 of them are identical to the N-terminal of V and P), the effect of deleting the I protein has often been overlooked. For the purposes of developing an effective vaccine, deleting I along with V may be advantageous for attenuation. However, it is possible that the I protein does have a role in viral pathogenesis and contributes to efficacy of a vaccine. To investigate the role of the I protein in virus life cycle in general, and in generating immune responses in particular, a recombinant virus lacking the I protein will be generated. The rMuVΔV genome will be used as a backbone to insert V between P and M. As a result of the mutations at the editing site, no I or V will be made from the P gene, but the V protein will be made from the newly inserted V. Similarly, the I gene will be inserted between HN and L in the backbone of the rMuVΔV genome to generate a recombinant rMuVΔV expressing I (rMuVΔ V+I). The reason for two different gene junctions to be inserted is that the V protein expression level ought to be high to reflect the wild type virus infection and expression level of I should be low as in wild type virus infected cells. Gene junction closer to the leader sequence (P-M junction) will give higher viral gene expression levels than the distant one (HN-L junction). The resultant viral construct will be analyzed as described in the previous examples.

Generation and analysis of revertants. In the case of rMuVΔV, several point mutations were introduced into the genome of MuV to give rise to the V protein deletion phenotype. It is possible that mutations that will revert the phenotype may be generated over a period of time. While a revertant of rMuVΔV has not been obtained after passing the virus in Vero cells over 20 passages, this experiment will be repeated in interferon competent cell lines. Vero cells are WHO and FDA-approved for vaccine production and do not produce type I IFN. That rMuVΔV has been stable in this cell line is encouraging for future mass production of rMuVΔV as a vaccine. However, Vero cells are defective in IFN production due to a deletion of IFN gene locus. Thus, the rate of revertant of rMuVΔV in an interferon competent environment will be examined. A549 cells, a human lung cell line that produces and responses to interferons, will be infected with rMuVΔV at a MOI of 0.1 and at 4 days post infection, media of the infected cells will be collected and used to infect fresh A549 cells at about 0.1 MOI. In preliminary studies, it was observed that rMuVΔV reached about $10^6$ pfu/ml and this titer will be used as a rough estimation for our experiment. Virus will be collected at every passage from the media of rMuVΔV-infected A549 cells and initially sequence viruses from passage 5, 10, 15 and 20. Similarly, other MuV mutants such as rMuVΔSH and rMuV-P-T147A will be examined.

Recombinant viruses that demonstrate enhanced viral gene expression and/or increased interferon induction will be tested for neurotoxicity and immunogenicity, as described in the previous example. Even mutations that do not achieve attenuation equal to rMuVΔV will be tested, because of their potential in induction of type I interferon. While Type I interferon is well known for its anti-viral activities, it also plays a positive role in inducing adaptive immunity (Iwasaki et al., 2004, Nat Immunol; 5(10):987-95). It promotes proliferation of memory T cells and prevents apoptosis of T cell. It plays a critical role in antigen cross presentation. It enhances humoral immunity and stimulates dendritic cells. It will be of significant interest if these IFN inducing MuV mutants generate more robust immune responses than its parent. If these mutations indeed produce better immune responses, these mutations will be incorporated into the rMuV genome.

It is possible that the I mRNA is a by-product of RNA editing and it may not have any significant functions. Investigating whether the I protein has a role in virus replication and pathogenesis will not only reveal potential novel functions about the I protein, it will also be important for vaccine development. In case rMuVΔV is too attenuated, expressing I in the backbone of rMuVΔV may help to design a virus with desirable level of attenuation. In the case of human PIV2 vaccine development, deleting the V protein resulting in a virus that is too attenuated to be effective (Schaap-Nutt et al., 2010, Virology; 397(2):285-98). Thus, adding V or I back may be result in a more appropriately attenuated MuV vaccine.

It is possible that the residues in the P protein of MuV that are responsible for PLK1 binding and phosphorylation may be different than predicted above. They will be searched using an approach similar to that used for PIV5: there are two PLK1 binding motifs within the P of MuV. Analogous residues in MuV will be examined. In preliminary studies, it has been found that the P protein and PLK1 interacted, indicating that a PLK1 binding site is within the P protein. In addition, mutations within P have been identified that enhanced its ability to facilitate viral gene expression, i.e., increased viral gene expression phenotype. Besides mutating the P protein, mutations will also be made in other genes. For instance, mutations in the L gene of PIV5 that enhances viral gene expression have been identified. The same mutations will be incorporated into the L gene of MuV.

Example 6

Immunogenicity of Recombinant Mumps Viruses in Ferrets

The immunogenicity and efficacy as a vaccine candidate of any of the MuV described herein will be tested in ferrets. The ferret is a small animal model system for the study of the pathogenesis of MuV infection. There is a remarkable similarity in the lung physiology and morphology between ferrets and humans. Ferrets are highly susceptible to infection with respiratory viruses. Ferrets have been established as an animal model for several other respiratory pathogens. Most importantly, MuV has been isolated from infected ferrets and pathological changes were observed in the lungs of infected animals (Gordon et al., 1956, *J Immunol;* 76(4): 328-33). Studies may include the infection of ferrets with a rMuV construct, the determination of immunogenicity of a rMuV construct in ferrets, and an examination of the efficacies of a such vaccine candidate in reducing virus load and pathological changes in lungs after challenge. As previously described (Gordon et al., 1956, *J Immunol;* 76(4):328-33), ferrets in a group of 5 will be infected with $10^7$ pfu of wild type MuV or a rMuV construct in 1 ml volume. Animals will be monitored for fever daily in the first week and every other day in second week after infection. At 3, 4, 5, 7, 9 and 11 days after inoculation, nasal washes and blood samples will be collected and titers of virus in them will be determined using plaque assay. At 3, 4, 7, 11 and 14 days after inoculation, ferrets will be sacrificed and lungs and turbinates will be collected and titers of virus will be determined. Pathological changes in lungs and turbinates will be examined using H&E staining. The immunogenicity of MuV mutants in ferrets will be examined, as described in the previous examples. Humoral immunity and cellular immunity against MuV will be examined after inoculation with the vaccine candidates as well as the JL vaccine and wild type MuV. Two-dose IN inoculation and three-dose (two-dose IM inoculation with JL followed by a single IN inoculation of the vaccine candidates) may be used. Besides immunological tests, vaccinated animals will be challenged with wild type MuV. Reagents for immunological assays in ferrets, including reagents for assaying cellular immune responses, will be generated. Such reagents may include monoclonal antibodies against CD3, CD4, CD8, IFN-β, IFN-γ, IL-6, and IL-8.

Example 7

Mumps Virus as a Vector for Respiratory Syncytial Virus Vaccine Development

Respiratory syncytial virus (RSV) is the most important cause of pediatric viral respiratory infection and is a major cause of morbidity and mortality among infants as well as immunocompromised subjects and the elderly (Collins, P. L., R. M. Chanock, and B. R. Murphy, Respiratory syncytial virus, in Fields Virology, D. M. Knipe and P. M. Howley, Editors. 2001, Lippincott, Williams and Wilkins: Philadelphia. p. 1443-1485.). In addition, severe RSV infection can result in wheezing and asthma later in life. Unlike infection by other respiratory viruses, RSV does not induce long-lasting protective immunity against subsequent infection. Thus, most individuals are infected multiple times throughout the course of their lives. Currently, there is no vaccine for RSV, nor are there effective curative treatments for severe RSV disease although aerosolized ribavirin and prophylactic immunoglobulin therapy are used in the clinical setting. However, the high cost of palivizumab prophylaxis raises the question of cost-effectiveness relative to health benefits due to the need for monthly injections during RSV season. Therefore, there is a pressing need for safe and effective vaccine for RSV.

As a negative non-segmented single-stranded RNA virus (NNSV), MuV is a good viral vector candidate for vaccine development because it does not have a DNA (or nuclear) phase in its life cycle, and thus the possible unintended consequences of genetic modifications of host cell DNA through recombination or insertion are avoided. In comparison to positive strand RNA viruses, the genome structure of MuV is stable. Thus, MuV is better suited as a vaccine vector than positive strand RNA viruses since the genomes of positive strand RNA viruses recombine and often delete the inserted foreign genes quickly.

Generation and analysis of MuV-F containing RSV F. The F gene of RSV (A2 strain) will be inserted between F and SH of MuV genome using the same strategy as for the generation of MuV-GFP (MuV-F). Briefly, the F gene will be combined with the gene end (GE), intergenic region (I) and gene start (GS) (which are important for viral mRNA synthesis), using a four-primer PCR approach (He et al., 1995, *Gene;* 164:75-79). The sequences will be inserted between GS of NP and the coding sequence of the NP gene. Although the "rule of six", which viral RNA genome requires to be multiple of six to be effective, is not absolute for MuV, the length of the genome with F will be maintained to be a multiple of six. Expression levels of F in MuV-F-infected cells will be examined using immunoprecipitation in comparison to RSV-infected cells. Growth rates of the virus at high and low MOI will be compared to MuV.

Generation and examination of MuV-F containing 3'-proximal F as a vaccine candidate. Negative strand RNA viruses, such as MuV, initiate transcription from the 3' end leader sequence, and transcription levels of the viral genes are affected by their distances to the leader sequence. For example, the NP gene of MuV, which is the closest to the leader sequence, is the most abundantly transcribed, whereas the L gene that is the located most distant from the leader sequence is least transcribed (FIG. 19). It is expected that the efficacy of the vaccine candidate will be enhanced by increasing the expression level of the F protein (as has been shown for recombinant RSV (Krempl et al., 2002, *J Virol;* 76(23):11931-42)). To increase the expression level of the F gene, the F gene will be inserted immediately downstream of the leader sequence and upstream of the NP gene (F-MuV) (FIG. 19).

The RSV G protein can be similarly expressed as the RSV F protein using mumps virus as a vector.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE LISTING FREE TEXT

SEQ ID NO:1 Mumps virus genome including V/P gene encoding a V protein and SH gene encoding a small hydrophobic protein
SEQ ID NO:2 Mumps virus V protein SEQ ID NO:3 Mumps virus small hydrophobic protein
SEQ ID NO:4 SH protein sequence for Mumps virus strain Glouc1/UK96
SEQ ID NO:5 SH protein sequence for Mumps virus strain UK01-22
SEQ ID NO:6 SH protein sequence for Mumps virus strain MuV-IA
SEQ ID NO:7 nucleic acid sequence upstream of SH gene
SEQ ID NO:8 recombinant nucleic acid sequence resulting from deletion of SH gene
SEQ ID NO:9 PCR product sequenced to confirm deletion of SH protein
SEQ ID NO:10 MuV-IA SH N-terminal peptide sequence used to generate antibody
SEQ ID NO:11 MuV-IA SH C-terminal peptide sequence used to generate antibody
SEQ ID NOs:12-13 MuV-IA V protein peptide sequence used to generate antibody
SEQ ID NO:14 nucleic acid editing sequence within the P/V gene
SEQ ID NO:15 recombinant nucleic acid sequence eliminating V protein expression
SEQ ID NO:16 recombinant nucleic acid sequence resulting from modification of P/V gene
SEQ ID NO:17 PCR product sequenced to confirm deletion of V protein
SEQ ID NO:18 nucleic acid sequence from the end of the NP gene to the start of the P/V gene a Mumps virus having a V protein deletion
SEQ ID NO:19-25 rescued nucleic acid sequence from the end of the NP gene to the start of the P/V gene in a Mumps virus having a V protein deletion
SEQ ID NO:26-81 synthetic oligonucleotide primer

SEQUENCE LISTING

```
<160> NUMBER OF SEQ ID NOS: 81

<210> SEQ ID NO 1
<211> LENGTH: 15384
<212> TYPE: DNA
<213> ORGANISM: Mumps virus
<220> FEATURE:
<221> NAME/KEY: CDS
<222> LOCATION: (1979)..(2653)
<223> OTHER INFORMATION: V/P gene encoding a V protein
<220> FEATURE:
<221> NAME/KEY: CDS
<222> LOCATION: (6268)..(6441)
<223> OTHER INFORMATION: SH gene encoding a small hydrophobic protein

<400> SEQUENCE: 1
accaagggga aaatgaagat gggatattgg tagaacaaat agtgtaagaa acagtaagcc      60
cggaagtggt gttttgcgat ttcgaggccg ggctcgatcc tcacctttca ttgtcaatag     120
gggacacttt gacactacct tgaaaatgtc gtccgtgctc aaagcatttg agcgattcac     180
tatagaacag gaacttcaag acaggggtga ggagggttca attccgccgg agactttaaa     240
gtcagcagtc aaagtcttcg ttattaacac acccaatccc accacacgct accagatgct     300
aaacttttgc ctaagaataa tttgcagtca aaatgctagg gcatctcaca gggtaggtgc     360
attgataaca ttattctcac ttccctcggc aggtatgcaa aatcatatta gactagcaga     420
tagatcaccc gaagcccaga tagaacgctg tgagattgat ggctttgagc ctggcacata     480
taggctgatt ccgaatgcac gcgccaatct tactgccaat gaaattgctg cctatgcttt     540
gcttgcagat gacctccctc caaccataaa taatggaact ccttatgtac atgcagatgt     600
tgaagggcag ccatgtgatg aaattgaaca attcctggat cgatgctaca gtgtactaat     660
ccaggcttgg gtgatggtct gtaaatgtat gacagcttac gaccaacctg ctggatctgc     720
tgatcggcga tttgcgaaat accagcagca aggtcgcctg gaagcaagat acatgctgca     780
gccagaagcc caaaggttga ttcaaactgc catcaggaaa agtcttgttg ttagacagta     840
tcttaccttt gaactccaac tggcaagacg gcaggggttg ctatcaaaca gatactatgc     900
aatggtgggt gacattggaa agtacattga gaattcaggc cttactgcct tctttctcac     960
cctcaaatat gcactaggta ccaaatggag tcctctgtca ttggccgcat tcaccggtga    1020
actcactaag ctccgatcct tgatgatgtt atatcgagat ctcggagaac aagccagata    1080
ccttgctttg ttggaggctc cccaaataat ggactttgct cccgggggct acccattgat    1140
attcagttat gctatgggag ttggtacagt cctagatgtc caaatgcgaa attacactta    1200
```

```
tgcacgacct ttcctaaatg gttactattt ccagattggg gttgagaccg cacgacggca    1260
acaaggcact gttgacaaca gagtagcaga tgatctaggc ctgactcctg aacaaagaac    1320
tgaggtcact cagcttgttg acaggcttgc aagaggcaga ggtgcgggaa taccaggtgg    1380
gccggtgaat ccctttgttc ctccagttca acagcaacaa cctgctgccg tatatgagga    1440
cattcctgca ttggaggaat cagatgacga tggtgatgaa gatggaggtg caggattcca    1500
aaatggagca caagcaccag ctgtaagaca gggaggtcaa aatgacttta gagcacagcc    1560
gttacaggat ccaattcaag cacaactctt catgccatta tatcctcaag tcagcaacat    1620
cccaaatcat cagaatcatc agattaatcg catcggggggg atggaacacc aagatttatt    1680
acgatacaac gagaatggtg attctcagca ggatgcaagg ggcgaacacg gaaatacctt    1740
cccaaacaat cccaatcaaa acgcacagtc acaagtgggt gactgggatg agtagatcac    1800
tgacatgacc aaactacccc caactgcaac aaactcagaa caatctagcc acagccaact    1860
gctcaaatcc actacattcc attcatattt agtctttaag aaaaaattag gcccggaaag    1920
aattagttct acgagcatcg acacgattat cttgatcgtg tttctttccg ggcaagcc      1978 atg gat caa ttt ata aaa caa gat gaa act ggt gat tta att gag aca      2026
Met Asp Gln Phe Ile Lys Gln Asp Glu Thr Gly Asp Leu Ile Glu Thr
1               5                   10                  15 gga atg aat gtt gca aat cac ttc cta tct gcc ccc att cag gga acc      2074
Gly Met Asn Val Ala Asn His Phe Leu Ser Ala Pro Ile Gln Gly Thr
            20                  25                  30 aac ttg ttg agc aag gcc aca atc atc ccc ggc gtt gca cca gta ctc      2122
Asn Leu Leu Ser Lys Ala Thr Ile Ile Pro Gly Val Ala Pro Val Leu
        35                  40                  45 att ggc aat cca gag caa aag aac att cag tac ccc act gca tca cat      2170
Ile Gly Asn Pro Glu Gln Lys Asn Ile Gln Tyr Pro Thr Ala Ser His
50                  55                  60 cag gga tcc aag tca aag gga aga agc tca ggg gcc aag ccc atc ata      2218
Gln Gly Ser Lys Ser Lys Gly Arg Ser Ser Gly Ala Lys Pro Ile Ile
65                  70                  75                  80 gtc tca tct tcc gaa gta ggc act gga ggg act cag att cct gag ccc      2266
Val Ser Ser Ser Glu Val Gly Thr Gly Gly Thr Gln Ile Pro Glu Pro
                85                  90                  95 ctt ttc gca caa acc gga caa ggt ggc act gtc acc acc gtt tat caa      2314
Leu Phe Ala Gln Thr Gly Gln Gly Gly Thr Val Thr Thr Val Tyr Gln
            100                 105                 110 gat cca act atc caa cca aca ggt tca tac cga agt gtg gaa ttg gct      2362
Asp Pro Thr Ile Gln Pro Thr Gly Ser Tyr Arg Ser Val Glu Leu Ala
        115                 120                 125 aag ata gga aaa gag aga atg att aat cga ttt gtt gaa aaa ccc agg      2410
Lys Ile Gly Lys Glu Arg Met Ile Asn Arg Phe Val Glu Lys Pro Arg
130                 135                 140 acc tca acg ccg gta aca gaa ttt aag agg ggg gcc ggg agc ggc tgc      2458
Thr Ser Thr Pro Val Thr Glu Phe Lys Arg Gly Ala Gly Ser Gly Cys
145                 150                 155                 160 tca agg cca gac aat cca aga gga ggg cat aga cgg gaa tgg agc ctc      2506
Ser Arg Pro Asp Asn Pro Arg Gly Gly His Arg Arg Glu Trp Ser Leu
                165                 170                 175 agc tgg gtc caa gga gag gtc cgg gtc ttt gag tgg tgc aac ccc ata      2554
Ser Trp Val Gln Gly Glu Val Arg Val Phe Glu Trp Cys Asn Pro Ile
            180                 185                 190 tgc tca cct atc act gcc gca gca aga ttc cac tcc tgc aaa tgt ggg      2602
Cys Ser Pro Ile Thr Ala Ala Ala Arg Phe His Ser Cys Lys Cys Gly
        195                 200                 205
```

| | | |
|---|---|---|
| aat tgc cca gca aag tgc gat cag tgc gaa cga gat tat gga cct cct<br>Asn Cys Pro Ala Lys Cys Asp Gln Cys Glu Arg Asp Tyr Gly Pro Pro<br>210                       215                    220 | | 2650 |
| tag agggatggat gctcgcctgc aacatcttga acaaaaggtg gacaaggtgc | | 2703 |
| ttgcacaggg cagcatggtg acccaaataa agaatgaatt atcaacagta aagacaacac | | 2763 |
| tagctacaat tgaaggaatg atggcgacag taaagatcat ggatcctgga aacccgacag | | 2823 |
| gggtcccagt tgatgagctt agaagaagtt ttagtgatca tgtaacaatt gttagtggac | | 2883 |
| caggagatgt gtcattcagc tccagtgaag aacccacact gtatttggat gaactagcga | | 2943 |
| ggcctatccc caagcctcgt cctgcaaagc agccaaaacc ccaaccagta aaggatttag | | 3003 |
| caggacggaa ggtgatgata accaaaatga tcactgactg tgtggccaat cctcaaatga | | 3063 |
| agcaggcgtt cgagcaacga ttggcaaagg ccagcaccga ggatgccctg aatgatatca | | 3123 |
| agcgagacat catacgaagc gccatatgaa cctaccaaga acaccagact cacgggaaaa | | 3183 |
| tccatgaact gatagccgca atgattccct attaaataaa aaataagcac gaacacaagt | | 3243 |
| ccaatccagc cacagcagca atggccggat cacagatcaa aattcctctt ccgaagcccc | | 3303 |
| ccgattcaga ttctcaaaga ctaaatgcat tccctgtaat catggctcaa gaaggcaaag | | 3363 |
| ggcgactcct cagacagatc agacttagga aaatattatc aggggatccg tctgatcagc | | 3423 |
| aaattacatt tgtgaataca tatggattca tccgtgctac tccagaaaca tcagagttca | | 3483 |
| tctctgaatc atcacaacaa aaggtaactc ctgtagtgac ggcgtgcatg ttatccttcg | | 3543 |
| gtgctggacc agtactagaa gacccacaac atatgctgaa agctcttgat cagacagata | | 3603 |
| tcagggttcg gaagacagca agtgataaag agcagatctt atttgagatc aaccgcattc | | 3663 |
| ccaatctatt caggcatcat caaatatctg cggaccatct gattcaggcc agctccgata | | 3723 |
| aatatgtcaa gtcaccagct aagttgattg caggagtaaa ttacatttac tgtgtcacat | | 3783 |
| ttttatccgt gacagtttgt tctgcctcac tcaagtttcg agttgcgcgc ccattgcttg | | 3843 |
| ctgcacgatc tagattagtg agagcagttc agatggaagt tttgcttcgg gtaacctgca | | 3903 |
| aaaaagactc tcaaatggca aagagcatgc taaatgaccc tgatggagaa ggttgcattg | | 3963 |
| catccgtgtg gttccacctg tgtaatctgt gcaaaggcag gaacaaactt agaagttacg | | 4023 |
| atgaaaatta ttttgcatct aagtgccgta agatgaattt gacagtcagc ataggggaca | | 4083 |
| tgtggggacc aaccattcta gtccatgcag gcggtcacat tccgacaact gcaaaacctt | | 4143 |
| tcttcaactc aagaggctgg gtctgtcacc ccatccatca atcatcacca tcgttggcga | | 4203 |
| agacccatg gtcatctggg tgtgaaatca aggctgccag tgctatcctc cagggctcag | | 4263 |
| actatgcatc actcgcaaaa actgatgaca taatatattc aaagataaag gtcgacaagg | | 4323 |
| atgcagccaa ctacaaggga gtatcctgga gtccatttag gaagtctgcc tcaatgagca | | 4383 |
| acctatgata attttctcta ttcccactga tgcctccagg aggatcaaca atcaggccga | | 4443 |
| tttgaccggt gataacttga ttgaaattat agaaaaaata agcctagaaa gatatcttac | | 4503 |
| ttctcgactt tcctactttg aaaatagaat tgatcagtaa tcatgaaggt ttctttagtt | | 4563 |
| acttgcttgg gctttgcagt cttttcattt tccatatgtg tgaatatcaa tatcttgcag | | 4623 |
| caaattggat atatcaagca acaagtcagg caactgagct attactcaca aagttcaagc | | 4683 |
| tcctacatag tggtcaagct tttaccgaat atccaaccca ctgataacag ctgtgaattc | | 4743 |
| aagagtgtaa cacaatacaa taagaccttg agtaatttgc ttcttccaat tgcagaaaac | | 4803 |
| ataaacaata ttgcatcgcc ctcacctgga tcaagacgtc ataaaaggtt tgctggcatt | | 4863 |
| gccattggca ttgctgcact cggtgttgca accgcagcac aagtaactgc cgctgtctca | | 4923 |

```
ttagttcaag cacagacaaa tgcacgcgca atagcggcga tgaaaaattc aatacaggca      4983
actaatcgag cagtcttcga agtgaaagaa ggcacccaac agttagctat agcggtacaa      5043
gcaatacaga accacatcaa tactattatg aacacccaat tgaacaatat gtcctgtcag      5103
attcttgata accagcttgc aacctccta ggattatacc taacagaatt aacaacagtg       5163
tttcagccac aattaattaa tccggcattg tcaccgatta gtatacaagc cttgaggtct      5223
ttgcttggaa gtatgacacc tgcagtggtt caagcaacat tatctacttc aatttctgct      5283
gctgaaatac taagtgccgg tctaatggag ggtcagattg tttctgttct gctggatgag      5343
atgcaggtga tagttaagat aaatattcca accattgtca cacaatcaaa tgcattggtg      5403
attgacttct actcaatttc gagctttatt aataatcagg aatccataat tcaattacca      5463
gacaggatct tggagatcgg gaatgaacaa tggagctatc cagcaaaaaa ttgtaagttg      5523
acaagacaca acatattctg ccaatacaat gaggcagaga ggctgagctt agaatcaaaa      5583
ctatgccttg caggcaatat aagtgcctgt gtgttctcac ccatagcagg gagttatatg      5643
aggcgatttg tagcactgga tggaacaatt gttgcaaact gtcgaagtct aacgtgtcta      5703
tgcaagagtc catcttatcc tatataccaa cctgaccatc atgcagtcac gaccattgat      5763
ctaaccgcat gtcagacggt gtccctagac ggattggatt tcagcattgt ctctctaagc      5823
aacatcactt acgctgagaa ccttaccatt tcattgtctc agacaatcaa tactcaaccc      5883
attgacatat caactgaact gatcaaggtc aatgcatccc tccaaaatgc cgttaagtac      5943
ataaaggaga gcaaccatca actccaatct gtgagtataa attctaaaat cggagctata      6003
atcatagcag ccttagtttt gagcatcctg tcaatgatca tttcactgtt gttttgctgc      6063
tgggcttaca ttgcaactaa agagatcaga agaatcaact tcaaaacaaa tcatatcaac      6123
acaatatcaa gtagtgtcga tgatctcatc aggtactaat cctaacatgg tgattcattc      6183
tgtatttaga aaatatttag aaaaaaacta aattaagaat gaatctcatg gggtcgtaac      6243
gtctcgtgac cctgccgttg cact atg ccg gcg atc caa ccc cca tta tac          6294
                              Met Pro Ala Ile Gln Pro Pro Leu Tyr
                              225                 230
ctc aca ttt cta ttg cta att ctt ctt tat ctg atc ata act ttg tat         6342
Leu Thr Phe Leu Leu Leu Ile Leu Leu Tyr Leu Ile Ile Thr Leu Tyr
    235             240                 245
gtc tgg att ata tta act gtt act tat aag act gcg gtg cga cat gca         6390
Val Trp Ile Ile Leu Thr Val Thr Tyr Lys Thr Ala Val Arg His Ala
250             255                 260                 265
gca ctg tac cag aga tcc ttc ttt cac tgg agt ttc gat cac tca ctc         6438
Ala Leu Tyr Gln Arg Ser Phe Phe His Trp Ser Phe Asp His Ser Leu
            270                 275                 280
taa gaagatcccc agttaggaca agtcccgatc catcatgcaa gaacaatctg              6491
catttgaata atgccgttca atcatgagac ataaagaaaa aaccaagcca gaacaaactt       6551
agggtcataa tacaacacaa aaccttagct gctatctcaa ttgtgctccg accgctcgaa       6611
agatggagcc ctcgaaattc ttcacaatat cggacagtgc cacctttgca cctgggcctg      6671
ttagcaatgc ggctaacaag aagacattcc gaacctgctt ccgaatactg gcactatctg      6731
tacaagctgt caccttata ttagttattg tcactttagg tgagcttgta aggatgatca       6791
atgatcaagg cttgagcaat cagttgtctt caattacaga caagataaga gagtcagcta      6851
ctatgattgc atctgctgtg ggagtaatga atcaagttat tcatggagta acggtatcct      6911
taccccctaca aattgaggga aaccaaaatc aattgttagc cacacttgcc acaatctgca      6971
```

```
ccagccaaaa acaagtctca aactgctcta caaacatccc cttagtcaat gacctcaggt     7031
ttataaatgg gatcaataaa ttcatcattg aagattacgc aactcatgat ttctctatcg     7091
gccatccact caatatgccc agctttatcc caactgcaac ttcacccaat ggttgcacaa     7151
gaattccatc cttttcttta ggtaagacac actggtgcta cacacataat gtaattaatg     7211
ccaactgcaa ggaccatact tcgtctaacc aatatgtgtc catggggatt ctcgttcaga     7271
ccgcgtcagg ttatcctatg ttcaaaacct taaaaatcca atatctcagt gatggcctga     7331
atcggaaaag ctgctcaatt gcaacagtcc ctgatgggtg cgcgatgtac tgttatgtct     7391
caactcaact tgaaaccgac gactatgcgg ggtccagtcc acccacccaa aaacttaccc     7451
tgttattcta taatgacacc gtcacagaaa ggacaatatc tccatctggt cttgaaggga     7511
attgggctac tttggtgcca ggagtgggga gtgggatata ttttgagaat aagttgatct     7571
tccctgcata tggtggtgtc ttgcccaata gtacactcgg ggttaaatta gcaagagaat     7631
ttttccggcc tgttaatcca tataatccat gttcagggcc acaacaagat ttagatcagc     7691
gtgctttgag gtcatacttc ccaagttatt tctctaatcg aagaatacag agtgcatttc     7751
ttgtctgtgc ctggaatcag atcctagtta caaattgtga gctagttgtc ccctcaagca     7811
atcagacaat gatgggtgca gaagggagag ttttattgat caataatcga ctattatatt     7871
atcagagaag taccagctgg tggccgtatg aactcctcta cgagatatca ttcacattta     7931
caaactctgg tccatcatct gtaaatatgt cctggatacc tatatattca ttcactcgtc     7991
ctggttcagg caattgcagt ggtgaaaatg tgtgcccgac tacttgtgtg tcaggggttt     8051
atcttgatcc ctggccatta actccatata gccaccaatc aggtattaac agaaatttct     8111
atttcacagg tgctctatta aattcaagta caactagagt aaatcctacc ctttatgtct     8171
ctgctcttaa taatcttaaa gtattagccc catatggtac tcaaggactg tttgcctcgt     8231
acaccacaac cacctgcttt caagataccg gtgatgctag tgtgtattgt gtttatatta     8291
tggaactagc atcaaatatt gttggagaat tccaaattct acctgtgcta actagattga     8351
ctatcacttg aatcatagtg aatgcagcgg gaagccctat tggcgtgtct caattttat      8411 cgattattaa gaaaaaacag gccagaatgg cgggcctaaa tgagatactc ctacctgaag     8471
tacatttaaa ctcacccatc gttagatata agcttttcta ctatatatta catggccagt     8531 taccaaaatga tttggagcca gatgacttgg gcccactagc aaatcagaat tggaaggcaa     8591
ttcgagctga agaatcccag gttcatgcac gtttaaaaca gatcagagta gaactcatcg     8651
caaggattcc tagtctccgg tggacccgct ctcaaagaga gattgctata ctcatttggc     8711
caagaatact tccaatcctc caagcatatg atcttcggca aagtatgcaa ttgcccacag     8771
tatgggagaa attgactcaa tccacagtta atcttataag tgatggtcta gaacgagttg     8831
tattacacat cagcaatcaa ctgacaggca agccaaactt gtttaccaga tctcgaacag     8891
gacaagacac aaaggattac tcaattccat ccactagaga gctatctcaa atatggttta     8951
acaatgagtg gagtggatct gtaaagacct ggcttatgat taaatataga atgaggcaac     9011
taatcacaaa ccaaaagaca ggtgagttaa cagatttagt aaccattgtg gatactaggt     9071
ccactctatg cattattacc ccagaattag ttgctttata ctctaatgag cacaaagcat     9131
taacgtacct caccttgaa atggtactaa tggtcactga tatgttggaa ggacgactga     9191
atgtttcttc tttgtgcaca gctagtcatt atctgtcccc actaaagaaa agaatcgaaa     9251
ttctcctaac attagttgat gaccttgctc tactcatggg ggacaaagta tacgtgttg      9311 tctcttcact tgagagtttt gtttacgccc aattacagta tggtgatcct gttgtagaca     9371
```

```
ttaagggtac attctatgga tttatatgta atgagattct cgatctgctg actgaggaca   9431
acatctttac tgaggaggag gcaaacaagg ttctcctgga cttgacgtca cagtttgaca   9491
atctatcccc tgatttaact gctgaactcc tctgcattat gagactttgg ggccacccca   9551
cattaaccgc cagccaagca gcatccaagg tccgagagtc catgtgcgct cccaaggtgt   9611
tagatttcca aacaataatg aagaccctgg ctttctttca cgcaatcctt attaacggtt   9671
ataggaggag ccataatgga atctggcctc ctactactct tcatggcaat gccccaaaa   9731 gcctcattga gatgcggcat gataattcag agcttaagta tgagtatgtc ctcaagaatt   9791
ggaaaagtat atctatgtta agaatacaca atgctttga tgcatcacct gatgaagatc   9851
tcagcatatt catgaaggat aaggcaataa gctgtccaaa gcaagactgg atgggagtat   9911
ttaggaggag cctcataaaa cagcgatatc gagatgcgaa tcgacctcta ccacaaccat   9971
tcaaccgacg gctactgttg aattttctag aggatgacag attcgatccc attaaagagc  10031
ttgagtatgt caccagtgga gaatatctta gggacccaga attttgtgca tcttactctc  10091
tcaaagagaa ggagataaag gctacaggtc gaatatttgc aaaaatgaca aagagaatga  10151
gatcgtgcca agtaattgcg gaatcattgt tggccaatca tgcaggtaaa ttaatgagag  10211
aaaatggagt tgttttagac cagttaaaat tgacaaaatc tttgttaacg atgaaccaaa  10271
ttggtattat atcagagcac agccgaagat ccactgctga caacatgact ttggcacact  10331
ccggttcaaa taagcacaga attaataata gtcaattcaa gaagaataaa gacaataaac  10391
atgagatgcc tgatgatggt tttgagatag cagcctgctt tctaacaact gacctcacaa  10451
aatactgctt aaattggagg taccaagtca tcatcccctt tgcgcgtaca ttgaattcaa  10511
tgtatggtat acctcacctg ttcgaatgga tacatttaag gctaatgcga agcactctct  10571
atgtcggtga tcccttcaat cctccatcag atcctaccca acttgacctt gatacagctc  10631
tcaatgatga tatatttata gtttctcctc gaggaggaat cgagggttta tgtcaaaaat  10691
tatggactat gatttccatc tcaacaatca tattatctgc aactgaggca acactagag   10751 ttatgagcat ggtccagggt gacaaccaag cgattgcaat caccactaga gtagtacgct  10811
cgctcagtca ttccgagaag aaggagcaag cttataaagc aagtaaatta ttctttgaaa  10871
ggcttagagc caacaatcat ggaattggac accacttgaa agaacaagaa acaatcctta  10931
gttctgattt cttcatatac agtaagagag tgttttacaa aggtcggatt ttgactcaag  10991
cattaaagaa cgtgagcaag atgtgcttaa cagccgatat actagggac tgttcacaag  11051 catcatgctc caatttagct actactgtaa tgcgcctgac tgagaatggg gtcgagaaag  11111
atttgtgtta ctttctgaat gcattcatga caatcagaca gttatgttat gatctagtat  11171
ttccccaaac taaatctctt agtcaggaca tcactaatgc ttatcttaac catccaatac  11231
ttatctcaag attgtgtcta ttaccatctc aattgggggg cctaaacttt ctctcatgta  11291
gtcgcctgtt caatagaaac atcggagacc cattagtgtc tgcaattgct gatgtgaaac  11351
gattaattaa agctggctgt ctagatatct gggtcctata acatccttt ggaaggaggc  11411 ctggaaaagg taagtggagc actctggcag ctgatcctta tactctaaac atagattatt  11471
tagttccttc aacaactttt ttaaagaagc atgcccaata tacattgatg aacggagtg   11531 ttaatcccat gctccgtgga gtattcagtg aaaatgcagc tgaggaagaa gaggaactcg  11591
cacagtatct attagatcgt gaggtagtca tgcccagggt tgcacatgta atacttgccc  11651
agtctagttg cggtagaaga aaacagattc aaggttactt ggattccact agaactatta  11711
```

-continued

```
tcaggtattc actggaggtg agaccattgt cagcaaagaa gctaaataca gtaatagaat    11771
ataacttatt gtatctatcc tacaatttgg agattattga aaaacccaat atagtccaac    11831
cttttttgaa tgcaatcaat gttgatactt gtagcatcga tatagccagg tcccttagaa    11891
aactatcctg gcaacttta cttaatggac gtcccatcga gggattagaa acacctgatc     11951
ccattgaatt ggtacatggg tgtttgataa ttgggtcaga tgaatgtgag cattgcagta    12011
gtggtgatga taaattcacc tggttttttcc tacccaaggg gataaggcta gataatgatc   12071
cggcatccaa cccacccata agagtacctt acatcggatc taaaacagat gagcggaggg    12131
ttgcgtcaat ggcttacatc aaaggagcat ctgtatcact gaaatcagca ctcaggttag    12191
cgggagtata tatttgggct ttcggagata cagaagaatc atggcaggac gcctatgagt    12251
tagcttccac tcgtgttaat ctcacactag agcaattgca atctctcact cctttaccaa    12311
catctgctaa cctagtacac agattagatg atggcaccac tcaattaaaa tttaccccgg    12371
caagctccta tgcattctct agcttcgttc atatatctaa cgactgtcaa gttctggaga    12431
tcgatgatca ggttaaagat tctaacctga tttaccaaca agttatgatt actggccttg    12491
ctttaattga cacatggaac aatcctccaa tcaacttctc tgtctatgag actacactac    12551
acttgcacac aggctcatct tgctgtataa gacctgtcga atcttgtgta gtaaatcctc    12611
ctttgcttcc tgtacccttc attaatgttc ctcaaatgaa taaatttgta tatgaccctg    12671
aaccactcag tttgctagaa atggaaaaaa ttgaggatat tgcttatcag accagaatcg    12731
gtggtttaga tcaaatccca cttctggaaa aaatacccctt actagctcac ctcaccgcca   12791
agcagatggt aaacagcatc actgggcttg atgaagcaac atctatagtg aatgatgctg    12851
tagttcaagc agattacact agcaattgga ttagtgaatg ctgctacact tacattgatt    12911
ctgtgtttgt ttactctggc tgggcattat tattggagct ttcatatcaa atgtactact    12971
taagaattca aggcatccaa ggaattctag actatgtgta tatgaccttg aggaggatac    13031
caggaatggc tataacaggc atctcatcca cgattagtca ccctcgtata ctcagaagat    13091
gcatcaattt ggatgtaata gccccaatca attctccaca catagcttca ctggattaca    13151
caaaattgag catagatgca gtaatgtggg gaactaagca ggttttgacc aacatttcgc    13211
aaggtatcga ttatgagata gtagttcctt ctgaaagcca actaacactt agtgatagag    13271
ttctaaatct agttgctcga aaattatcac tactggcaat catctgggcc aattataact    13331
atcctccaaa ggttaaaggt atgtcacctg aggacaaatg tcaggcttta actacacatc    13391
taatccaaac tgtcgaatat gttgagcaca ttcagattga aagacaaac atcaggagga     13451
tgattcttga accaaaatta actgcctacc ctagtaattt gttttatcta tctcgaaagt    13511
tgcttaatgc tattcgagat tctgaagaag acaatttctct gattgcatcc tattataaca   13571
gttttggatt tctggaacca atactaatgg aatctaaaat attcaatcta aattcatccg    13631
aatcagcatc tcttacagaa tttgatttca tcctcaactt ggaattgtct gaagccagtc    13691
ttgagaaata ctctctccca agtttgttga tgacggctga gaatatggat aacccatttc    13751
ctcaaccacc ccttcatcat gttctcagac cactaggatt atcatccact tcatggtata    13811
aaacaatcag tgttttgaat tatattagcc atatgaaaat atctgacggt gcccatctat    13871
acttggcaga gggaagcggg gcctctatgt cacttataga gactttcttg cccggtgaaa    13931
caatatggta caacagccta ttcaatagtg tgagaatcc tcccaacgc aattttgctc      13991
ctttgcccac ccagttttatt gaaagtgtcc cttacagatt gattcaagca ggtatagcag    14051
caggaagtgg tgtagtgcaa agtttctatc cactctggaa cggtaacagc gatatcactg    14111
```

```
acttgagcac gaaaaccagt gtcgaataca ttattcacaa ggtaggagct gatacatgtg   14171
cattggtcca tgtggatttg gagggtgtgc ccggctcaat gaacagcatg ttggagagag   14231
cccaagtgca tgcgctactg atcacagtaa ctgtattaaa gccaggcggc ttactaatct   14291
tgaaagcttc atgggaacct tttaatcgat tttccttttt actcacaata ctctggcaat   14351
tcttctccac aataaggatc ctgcgatctt catactccga cccgaataat cacgaggtat   14411
acataatagc tacactagca gttgatccca ccacatcctc ctttacaact gctctgaata   14471
gagcgcgcac cctgaatgaa caggggtttt cacttatccc acctgaatta gtgagcgagt   14531
actggaggag gcgtgttgaa caagggcaga ttatacagga tcgtatagat aaagtcatat   14591
cagagtgtgt cagagaccaa tatctgacgg acaacaacat tatccttcag gcgggaggga   14651
ctccaagcac aagaaaatgg ttggatctac ctgactatcc gtcgttcaat gaattacaat   14711
cagagatggc cagactcata acaattcatc tcaaagaggt aatagaaatc ctaaaaggcc   14771
aatcatcaga tcatgacacc ctattattta cttcatacaa tgtaggtccc ctcgggaaaa   14831
taaatacgat actcaggttg attgttgaga gaattcttat gtacactgta agaaactggt   14891
gtatcttgcc cacccaaact cgtctcacct tacgacagtc tatcgagctt ggagagttta   14951
gactaaggga cgtgataaca cccatggaga tccttaaatt atccccaac aggaaatatc    15011
tgaagtctgc attaaaccaa tcaacattca atcatctaat gggagaaaca tctgacatat   15071
tgttaaatcg agcctatcaa aagagaattt ggaaagccat tgggtgtgta atctattgct   15131
ttggtttgct tactcctgat gttgaagatt ccgagcgcat tgatattgac aatgatatac   15191
ctgattatga tatccacggg gacataattt aaatcgacta agactcctc tggcacgata    15251
cgtcaccaaa aggtgccaca ccggcatcaa aactcctcta gaccgcacac gacctcgaac   15311
aatcacaacc acatcagtat tgaatccata atatcatttt aagaaaaaat tgattttact   15371
ttctccccct tggt                                                     15384

<210> SEQ ID NO 2
<211> LENGTH: 224
<212> TYPE: PRT
<213> ORGANISM: Mumps virus

<400> SEQUENCE: 2

Met Asp Gln Phe Ile Lys Gln Asp Glu Thr Gly Asp Leu Ile Glu Thr
1               5                   10                  15

Gly Met Asn Val Ala Asn His Phe Leu Ser Ala Pro Ile Gln Gly Thr
                20                  25                  30

Asn Leu Leu Ser Lys Ala Thr Ile Ile Pro Gly Val Ala Pro Val Leu
        35                  40                  45

Ile Gly Asn Pro Glu Gln Lys Asn Ile Gln Tyr Pro Thr Ala Ser His
    50                  55                  60

Gln Gly Ser Lys Ser Lys Gly Arg Ser Gly Ala Lys Pro Ile Ile
65                  70                  75                  80

Val Ser Ser Ser Glu Val Gly Thr Gly Gly Thr Gln Ile Pro Glu Pro
                85                  90                  95

Leu Phe Ala Gln Thr Gly Gln Gly Gly Thr Val Thr Thr Val Tyr Gln
                100                 105                 110

Asp Pro Thr Ile Gln Pro Thr Gly Ser Tyr Arg Ser Val Glu Leu Ala
        115                 120                 125

Lys Ile Gly Lys Glu Arg Met Ile Asn Arg Phe Val Glu Lys Pro Arg
    130                 135                 140
```

```
Thr Ser Thr Pro Val Thr Glu Phe Lys Arg Gly Ala Gly Ser Gly Cys
145                 150                 155                 160

Ser Arg Pro Asp Asn Pro Arg Gly Gly His Arg Arg Glu Trp Ser Leu
            165                 170                 175

Ser Trp Val Gln Gly Glu Val Arg Val Phe Glu Trp Cys Asn Pro Ile
        180                 185                 190

Cys Ser Pro Ile Thr Ala Ala Ala Arg Phe His Ser Cys Lys Cys Gly
    195                 200                 205

Asn Cys Pro Ala Lys Cys Asp Gln Cys Glu Arg Asp Tyr Gly Pro Pro
210                 215                 220

<210> SEQ ID NO 3
<211> LENGTH: 57
<212> TYPE: PRT
<213> ORGANISM: Mumps virus

<400> SEQUENCE: 3

Met Pro Ala Ile Gln Pro Pro Leu Tyr Leu Thr Phe Leu Leu Leu Ile
1               5                   10                  15

Leu Leu Tyr Leu Ile Ile Thr Leu Tyr Val Trp Ile Ile Leu Thr Val
            20                  25                  30

Thr Tyr Lys Thr Ala Val Arg His Ala Ala Leu Tyr Gln Arg Ser Phe
        35                  40                  45

Phe His Trp Ser Phe Asp His Ser Leu
    50                  55

<210> SEQ ID NO 4
<211> LENGTH: 57
<212> TYPE: PRT
<213> ORGANISM: Mumps virus
<220> FEATURE:
<221> NAME/KEY: MISC_FEATURE
<222> LOCATION: (1)..(57)
<223> OTHER INFORMATION: SH protein sequence for Mumps virus strain
      Glouc1/UK96

<400> SEQUENCE: 4

Met Pro Ala Ile Gln Pro Pro Leu Tyr Leu Thr Phe Leu Leu Leu Ile
1               5                   10                  15

Leu Leu Tyr Leu Ile Ile Thr Leu Tyr Val Trp Ile Ile Leu Thr Ile
            20                  25                  30

Thr Tyr Lys Thr Ala Val Arg His Ala Ala Leu Tyr Gln Arg Ser Phe
        35                  40                  45

Phe His Trp Ser Phe Asp His Ser Leu
    50                  55

<210> SEQ ID NO 5
<211> LENGTH: 57
<212> TYPE: PRT
<213> ORGANISM: Mumps virus
<220> FEATURE:
<221> NAME/KEY: MISC_FEATURE
<222> LOCATION: (1)..(57)
<223> OTHER INFORMATION: SH protein sequence for Mumps virus strain
      UK01-22

<400> SEQUENCE: 5

Met Pro Ala Ile Gln Pro Pro Leu Tyr Leu Thr Phe Leu Leu Leu Ile
1               5                   10                  15

Leu Leu Tyr Leu Ile Ile Thr Ser Tyr Val Trp Ile Ile Leu Thr Ile
            20                  25                  30
```

```
Thr Tyr Lys Thr Ala Val Arg His Ala Ala Leu Tyr Gln Arg Ser Phe
        35                  40                  45

Phe His Trp Ser Phe Asp His Ser Leu
    50                  55

<210> SEQ ID NO 6
<211> LENGTH: 57
<212> TYPE: PRT
<213> ORGANISM: Mumps virus
<220> FEATURE:
<221> NAME/KEY: MISC_FEATURE
<222> LOCATION: (1)..(57)
<223> OTHER INFORMATION: SH protein sequence for Mumps virus strain
      MuV-IA

<400> SEQUENCE: 6

Met Pro Ala Ile Gln Pro Pro Leu Tyr Leu Thr Phe Leu Leu Leu Ile
1               5                   10                  15

Leu Leu Tyr Leu Ile Ile Thr Leu Tyr Val Trp Ile Ile Leu Thr Val
            20                  25                  30

Thr Tyr Lys Thr Ala Val Arg His Ala Ala Leu Tyr Gln Arg Ser Phe
        35                  40                  45

Phe His Trp Ser Phe Asp His Ser Leu
    50                  55

<210> SEQ ID NO 7
<211> LENGTH: 15
<212> TYPE: DNA
<213> ORGANISM: Mumps virus
<220> FEATURE:
<221> NAME/KEY: misc_feature
<222> LOCATION: (1)..(15)
<223> OTHER INFORMATION: nucleic acid sequence upstream of SH gene

<400> SEQUENCE: 7
atgccggcga tccaa                                                    15

<210> SEQ ID NO 8
<211> LENGTH: 18
<212> TYPE: DNA
<213> ORGANISM: artificial
<220> FEATURE:
<223> OTHER INFORMATION: recombinant nucleic acid sequence resulting
      from deletion of SH gene

<400> SEQUENCE: 8
atgccggcgg ctagctaa                                                 18

<210> SEQ ID NO 9
<211> LENGTH: 34
<212> TYPE: DNA
<213> ORGANISM: artificial
<220> FEATURE:
<223> OTHER INFORMATION: PCR product sequenced to confirm deletion of
      SH protein

<400> SEQUENCE: 9
ttgcactatg ccggcggcta gctaagaaga tccc                               34

<210> SEQ ID NO 10
<211> LENGTH: 15
<212> TYPE: PRT
<213> ORGANISM: artificial
<220> FEATURE:
<223> OTHER INFORMATION: MuV-IA SH N-terminal peptide sequence used to
```

-continued

```
      generate antibody

<400> SEQUENCE: 10

Met Pro Ala Ile Gln Pro Pro Leu Tyr Leu Thr Phe Leu Leu Cys
1               5                   10                  15

<210> SEQ ID NO 11
<211> LENGTH: 15
<212> TYPE: PRT
<213> ORGANISM: artificial
<220> FEATURE:
<223> OTHER INFORMATION: MuV-IA SH C-terminal peptide sequence used to
      generate antibody

<400> SEQUENCE: 11

Cys Tyr Gln Arg Ser Phe Phe His Trp Ser Phe Asp His Ser Leu
1               5                   10                  15

<210> SEQ ID NO 12
<211> LENGTH: 15
<212> TYPE: PRT
<213> ORGANISM: artificial
<220> FEATURE:
<223> OTHER INFORMATION: MuV-IA V protein pept

```
<211> LENGTH: 12
<212> TYPE: DNA
<213> ORGANISM: artificial
<220> FEATURE:
<223> OTHER INFORMATION: recombinant nucleic acid sequence resulting
      from modification of P/V gene
<220> FEATURE:
<221> NAME/KEY: 3'UTR
<222> LOCATION: (1)..(12)
<220> FEATURE:
<221> NAME/KEY: misc_feature
<222> LOCATION: (3)..(6)
<223> OTHER INFORMATION: nucleotides inserted to maintain genome length

<400> SEQUENCE: 16
agctagctag ca                                                            12

<210> SEQ ID NO 17
<211> LENGTH: 34
<212> TYPE: DNA
<213> ORGANISM: artificial
<220> FEATURE:
<223> OTHER INFORMATION: PCR product sequenced to confirm deletion of
      V protein

<400> SEQUENCE: 17
aatttaagag aggagggccg ggagcggctg ctca                                    34

<210> SEQ ID NO 18
<211> LENGTH: 32
<212> TYPE: DNA
<213> ORGANISM: Mumps virus
<220> FEATURE:
<221> NAME/KEY: misc_feature
<222> LOCATION: (1)..(32)
<223> OTHER INFORMATION: nucleic acid sequence from the end of the NP
      gene to the start of the P/V gene a Mumps virus having a V protein
      deletion

<400> SEQUENCE: 18
agtctttaag aaaaaattag gcccggaaag aa                                      32

<210> SEQ ID NO 19
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 19
agtctttatg aaaaaattag gcccggaaag aa                                      32

<210> SEQ ID NO 20
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 20
agtctttaag aaaaaattag gctcggaaag aa                                      32

<210> SEQ ID NO 21
<211> LENGTH: 32
<212> TYPE: DNA
```

```
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 21
agtctttagg aaaaaattag gctcggaaag aa                                      32

<210> SEQ ID NO 22
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 22
agtctttagg aaaaaattag gcccggaaag aa                                      32

<210> SEQ ID NO 23
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 23
agtctgtaag aaaaaattag gcccggaaag aa                                      32

<210> SEQ ID NO 24
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 24
agtctttagg aaaaaattag gcccggaaag aa                                      32

<210> SEQ ID NO 25
<211> LENGTH: 32
<212> TYPE: DNA
<213> ORGANISM: artificial
<220> FEATURE:
<223> OTHER INFORMATION: rescued nucleic acid sequence from the end of
      the NP gene to the start of the P/V gene in a Mumps virus having
      a V protein deletion

<400> SEQUENCE: 25
agtcttgaag aaaaaattag gcccggaaag aa                                      32

<210> SEQ ID NO 26
<211> LENGTH: 23
<212> TYPE: DNA
<213> ORGANISM: artificial
<220> FEATURE:
<223> OTHER INFORMATION: synthetic oligonucleotide primer

<400> SEQUENCE: 26
tgaatcatag tgaatgcagc agg                                                23
```

<210> SEQ ID NO 27
<211> LENGTH: 19
<212> TYPE: DNA
<213> ORGANISM: artificial
<220> FEATURE:
<223> OTHER INFORMATION: synthetic oligonucleotide primer

<400> SEQUENCE: 27
gccctattgg cgtgtctca                                            19

<210> SEQ ID NO 28
<211> LENGTH: 20
<212> TYPE: DNA
<213> ORGANISM: artificial
<220> FEATURE:
<223> OTHER INFORMATION: synthetic oligonucleotide primer

<400> SEQUENCE: 28
tggtgacgta tcgtgccaga                                           20

<210> SEQ ID NO 29
<211> LENGTH: 19
<212> TYPE: DNA
<213> ORGANISM: artificial
<220> FEATURE:
<223> OTHER INFORMATION: synthetic oligonucleotide primer

<400> SEQUENCE: 29
aacagtaagc ccggaagtg                                            19

<210> SEQ ID NO 30
<211> LENGTH: 20
<212> TYPE: DNA
<213> ORGANISM: artificial
<220> FEATURE:
<223> OTHER INFORMATION: synthetic oligonucleotide primer

<400> SEQUENCE: 30
ccaatgagta ctggtgcaac                                           20

<210> SEQ ID NO 31
<211> LENGTH: 18
<212> TYPE: DNA
<213> ORGANISM: artificial
<220> FEATURE:
<223> OTHER INFORMATION: synthetic oligonucleotide primer

<400> SEQUENCE: 31
gcgactggga tgagtaaa                                             18

<210> SEQ ID NO 32
<211> LENGTH: 19
<212> TYPE: DNA
<213> ORGANISM: artificial
<220> FEATURE:
<223> OTHER INFORMATION: synthetic oligonucleotide primer

<400> SEQUENCE: 32
tggattggac ttgtgttcg                                            19

<210> SEQ ID NO 33
<211> LENGTH: 18
<212> TYPE: DNA
<213> ORGANISM: artificial
<220> FEATURE:
<223> OTHER INFORMATION: synthetic oligonucleotide primer

```
<400> SEQUENCE: 33
gcgagacatc atacgaag                                            18

<210> SEQ ID NO 34
<211> LENGTH: 20
<212> TYPE: DNA
<213> ORGANISM: artificial
<220> FEATURE:
<223> OTHER INFORMATION: synthetic oligonucleotide primer

<400> SEQUENCE: 34
aagcttgacc actatgtagg                                          20

<210> SEQ ID NO 35
<211> LENGTH: 19
<212> TYPE: DNA
<213> ORGANISM: artificial
<220> FEATURE:
<223> OTHER INFORMATION: synthetic oligonucleotide primer

<400> SEQUENCE: 35
cctcaatgag caacctatg                                           19

<210> SEQ ID NO 36
<211> LENGTH: 22
<212> TYPE: DNA
<213> ORGANISM: artificial
<220> FEATURE:
<223> OTHER INFORMATION: synthetic oligonucleotide primer

<400> SEQUENCE: 36
ttagtacctg atgagatcat cg                                       22

<210> SEQ ID NO 37
<211> LENGTH: 22
<212> TYPE: DNA
<213> ORGANISM: artificial
<220> FEATURE:
<223> OTHER INFORMATION: synthetic oligonucleotide primer

<400> SEQUENCE: 37
gaattcatgc cggcgatcca ac                                       22

<210> SEQ ID NO 38
<211> LENGTH: 26
<212> TYPE: DNA
<213> ORGANISM: artificial
<220> FEATURE:
<223> OTHER INFORMATION: synthetic oligonucleotide primer

<400> SEQUENCE: 38
gctagcttag agtgagtgat cgaaac                                   26

<210> SEQ ID NO 39
<211> LENGTH: 19
<212> TYPE: DNA
<213> ORGANISM: artificial
<220> FEATURE:
<223> OTHER INFORMATION: synthetic oligonucleotide primer

<400> SEQUENCE: 39
atggagccct cgaaattct                                           19

<210> SEQ ID NO 40
<211> LENGTH: 21
```

```
<212> TYPE: DNA
<213> ORGANISM: artificial
<220> FEATURE:
<223> OTHER INFORMATION: synthetic oligonucleotide primer

<400> SEQUENCE: 40
aacgatgggt gagtttaaat g                                              21

<210> SEQ ID NO 41
<211> LENGTH: 20
<212> TYPE: DNA
<213> ORGANISM: artificial
<220> FEATURE:
<223> OTHER INFORMATION: synthetic oligonucleotide primer

<400> SEQUENCE: 41
ggcttgggtg atggtctgta                                                20

<210> SEQ ID NO 42
<211> LENGTH: 20
<212> TYPE: DNA
<213> ORGANISM: artificial
<220> FEATURE:
<223> OTHER INFORMATION: synthetic oligonucleotide primer

<400> SEQUENCE: 42
cattttggaa tcctgcacct                                                20

<210> SEQ ID NO 43
<211> LENGTH: 20
<212> TYPE: DNA
<213> ORGANISM: artificial
<220> FEATURE:
<223> OTHER INFORMATION: synthetic oligonucleotide primer

<400> SEQUENCE: 43
tgcaaggacc atacttcgtc                                                20

<210> SEQ ID NO 44
<211> LENGTH: 19
<212> TYPE: DNA
<213> ORGANISM: artificial
<220> FEATURE:
<223> OTHER INFORMATION: synthetic oligonucleotide primer

<400> SEQUENCE: 44
gagttcatac ggccaccag                                                 19

<210> SEQ ID NO 45
<211> LENGTH: 20
<212> TYPE: DNA
<213> ORGANISM: artificial
<220> FEATURE:
<223> OTHER INFORMATION: synthetic oligonucleotide primer

<400> SEQUENCE: 45
ctcaacgccg gtaacagaat                                                20

<210> SEQ ID NO 46
<211> LENGTH: 24
<212> TYPE: DNA
<213> ORGANISM: artificial
<220> FEATURE:
<223> OTHER INFORMATION: synthetic oligonucleotide primer

<400> SEQUENCE: 46
```

| atgaaggttc ctttagttac ttgc | 24 |

<210> SEQ ID NO 47
<211> LENGTH: 20
<212> TYPE: DNA
<213> ORGANISM: artificial
<220> FEATURE:
<223> OTHER INFORMATION: synthetic oligonucleotide primer

<400> SEQUENCE: 47

| agccaactgc tcaaatccac | 20 |

<210> SEQ ID NO 48
<211> LENGTH: 19
<212> TYPE: DNA
<213> ORGANISM: artificial
<220> FEATURE:
<223> OTHER INFORMATION: synthetic oligonucleotide primer

<400> SEQUENCE: 48

| atgtcgtccg tgctcaaag | 19 |

<210> SEQ ID NO 49
<211> LENGTH: 19
<212> TYPE: DNA
<213> ORGANISM: artificial
<220> FEATURE:
<223> OTHER INFORMATION: synthetic oligonucleotide primer

<400> SEQUENCE: 49

| cggtctcaac cccaatctg | 19 |

<210> SEQ ID NO 50
<211> LENGTH: 20
<212> TYPE: DNA
<213> ORGANISM: artificial
<220> FEATURE:
<223> OTHER INFORMATION: synthetic oligonucleotide primer

<400> SEQUENCE: 50

| gggggctacc cattgatatt | 20 |

<210> SEQ ID NO 51
<211> LENGTH: 20
<212> TYPE: DNA
<213> ORGANISM: artificial
<220> FEATURE:
<223> OTHER INFORMATION: synthetic oligonucleotide primer

<400> SEQUENCE: 51

| gaaaaggggc tcaggaatct | 20 |

<210> SEQ ID NO 52
<211> LENGTH: 20
<212> TYPE: DNA
<213> ORGANISM: artificial
<220> FEATURE:
<223> OTHER INFORMATION: synthetic oligonucleotide primer

<400> SEQUENCE: 52

| ttcagtaccc cactgcatca | 20 |

<210> SEQ ID NO 53
<211> LENGTH: 20
<212> TYPE: DNA
<213> ORGANISM: artificial

```
<220> FEATURE:
<223> OTHER INFORMATION: synthetic oligonucleotide primer

<400> SEQUENCE: 53
ggctggattg gacttgtgtt                                                    20

<210> SEQ ID NO 54
<211> LENGTH: 20
<212> TYPE: DNA
<213> ORGANISM: artificial
<220> FEATURE:
<223> OTHER INFORMATION: synthetic oligonucleotide primer

<400> SEQUENCE: 54
cgaggatgcc ctgaatgata                                                    20

<210> SEQ ID NO 55
<211> LENGTH: 20
<212> TYPE: DNA
<213> ORGANISM: artificial
<220> FEATURE:
<223> OTHER INFORMATION: synthetic oligonucleotide primer

<400> SEQUENCE: 55
gcatagtctg agccctggag                                                    20

<210> SEQ ID NO 56
<211> LENGTH: 20
<212> TYPE: DNA
<213> ORGANISM: artificial
<220> FEATURE:
<223> OTHER INFORMATION: synthetic oligonucleotide primer

<400> SEQUENCE: 56
cacattccga caactgcaaa                                                    20

<210> SEQ ID NO 57
<211> LENGTH: 20
<212> TYPE: DNA
<213> ORGANISM: artificial
<220> FEATURE:
<223> OTHER INFORMATION: synthetic oligonucleotide primer

<400> SEQUENCE: 57
tgaaccactg caggtgtcat                                                    20

<210> SEQ ID NO 58
<211> LENGTH: 20
<212> TYPE: DNA
<213> ORGANISM: artificial
<220> FEATURE:
<223> OTHER INFORMATION: synthetic oligonucleotide primer

<400> SEQUENCE: 58
gcttgcaacc tccctaggat                                                    20

<210> SEQ ID NO 59
<211> LENGTH: 20
<212> TYPE: DNA
<213> ORGANISM: artificial
<220> FEATURE:
<223> OTHER INFORMATION: synthetic oligonucleotide primer

<400> SEQUENCE: 59
tggcactgtc cgatattgtg                                                    20
```

```
<210> SEQ ID NO 60
<211> LENGTH: 24
<212> TYPE: DNA
<213> ORGANISM: artificial
<220> FEATURE:
<223> OTHER INFORMATION: synthetic oligonucleotide primer

<400> SEQUENCE: 60
gtgtcgatga tctcatcagg tact                                           24

<210> SEQ ID NO 61
<211> LENGTH: 20
<212> TYPE: DNA
<213> ORGANISM: artificial
<220> FEATURE:
<223> OTHER INFORMATION: synthetic oligonucleotide primer

<400> SEQUENCE: 61
acctcaaagc acgctgatct                                                20

<210> SEQ ID NO 62
<211> LENGTH: 20
<212> TYPE: DNA
<213> ORGANISM: artificial
<220> FEATURE:
<223> OTHER INFORMATION: synthetic oligonucleotide primer

<400> SEQUENCE: 62
gggaattggg ctactttggt                                                20

<210> SEQ ID NO 63
<211> LENGTH: 20
<212> TYPE: DNA
<213> ORGANISM: artificial
<220> FEATURE:
<223> OTHER INFORMATION: synthetic oligonucleotide primer

<400> SEQUENCE: 63
gtgcatgaac ctgggattct                                                20

<210> SEQ ID NO 64
<211> LENGTH: 21
<212> TYPE: DNA
<213> ORGANISM: artificial
<220> FEATURE:
<223> OTHER INFORMATION: synthetic oligonucleotide primer

<400> SEQUENCE: 64
gataccggtg atgctagtgt g                                              21

<210> SEQ ID NO 65
<211> LENGTH: 21
<212> TYPE: DNA
<213> ORGANISM: artificial
<220> FEATURE:
<223> OTHER INFORMATION: synthetic oligonucleotide primer

<400> SEQUENCE: 65
gaaagaaagc cagggtcttc a                                              21

<210> SEQ ID NO 66
<211> LENGTH: 20
<212> TYPE: DNA
<213> ORGANISM: artificial
<220> FEATURE:
<223> OTHER INFORMATION: synthetic oligonucleotide primer
```

```
<400> SEQUENCE: 66
gctctactca tgggggacaa                                              20

<210> SEQ ID NO 67
<211> LENGTH: 22
<212> TYPE: DNA
<213> ORGANISM: artificial
<220> FEATURE:
<223> OTHER INFORMATION: synthetic oligonucleotide primer

<400> SEQUENCE: 67
atcaaggtca agttgggtag ga                                           22

<210> SEQ ID NO 68
<211> LENGTH: 20
<212> TYPE: DNA
<213> ORGANISM: artificial
<220> FEATURE:
<223> OTHER INFORMATION: synthetic oligonucleotide primer

<400> SEQUENCE: 68
ccaagtcatc atcccctttg                                              20

<210> SEQ ID NO 69
<211> LENGTH: 20
<212> TYPE: DNA
<213> ORGANISM: artificial
<220> FEATURE:
<223> OTHER INFORMATION: synthetic oligonucleotide primer

<400> SEQUENCE: 69
ttgctgacaa tggtctcacc                                              20

<210> SEQ ID NO 70
<211> LENGTH: 22
<212> TYPE: DNA
<213> ORGANISM: artificial
<220> FEATURE:
<223> OTHER INFORMATION: synthetic oligonucleotide primer

<400> SEQUENCE: 70
catgcccaat atacattgat gg                                           22

<210> SEQ ID NO 71
<211> LENGTH: 21
<212> TYPE: DNA
<213> ORGANISM: artificial
<220> FEATURE:
<223> OTHER INFORMATION: synthetic oligonucleotide primer

<400> SEQUENCE: 71
tgaagggtac aggaagcaaa g                                            21

<210> SEQ ID NO 72
<211> LENGTH: 21
<212> TYPE: DNA
<213> ORGANISM: artificial
<220> FEATURE:
<223> OTHER INFORMATION: synthetic oligonucleotide primer

<400> SEQUENCE: 72
ctggccttgc tttaattgag a                                            21

<210> SEQ ID NO 73
```

```
<211> LENGTH: 21
<212> TYPE: DNA
<213> ORGANISM: artificial
<220> FEATURE:
<223> OTHER INFORMATION: synthetic oligonucleotide primer

<400> SEQUENCE: 73
agagatgctg attcggatga a                                              21

<210> SEQ ID NO 74
<211> LENGTH: 23
<212> TYPE: DNA
<213> ORGANISM: artificial
<220> FEATURE:
<223> OTHER INFORMATION: synthetic oligonucleotide primer

<400> SEQUENCE: 74
gaaccaaaat taactgccta ccc                                            23

<210> SEQ ID NO 75
<211> LENGTH: 20
<212> TYPE: DNA
<213> ORGANISM: artificial
<220> FEATURE:
<223> OTHER INFORMATION: synthetic oligonucleotide primer

<400> SEQUENCE: 75
ccgcctgaag gataatgttg                                                20

<210> SEQ ID NO 76
<211> LENGTH: 20
<212> TYPE: DNA
<213> ORGANISM: artificial
<220> FEATURE:
<223> OTHER INFORMATION: synthetic oligonucleotide primer

<400> SEQUENCE: 76
ccctgaatga acagggggttt                                               20

<210> SEQ ID NO 77
<211> LENGTH: 19
<212> TYPE: DNA
<213> ORGANISM: artificial
<220> FEATURE:
<223> OTHER INFORMATION: synthetic oligonucleotide primer

<400> SEQUENCE: 77
cttttgctgg cctttttgct                                                19

<210> SEQ ID NO 78
<211> LENGTH: 20
<212> TYPE: DNA
<213> ORGANISM: artificial
<220> FEATURE:
<223> OTHER INFORMATION: synthetic oligonucleotide primer

<400> SEQUENCE: 78
ctgctaacaa agcccgaaag                                                20

<210> SEQ ID NO 79
<211> LENGTH: 20
<212> TYPE: DNA
<213> ORGANISM: artificial
<220> FEATURE:
<223> OTHER INFORMATION: synthetic oligonucleotide primer

<400> SEQUENCE: 79
```

```
aagttgcagg accacttctg                                               20

<210> SEQ ID NO 80
<211> LENGTH: 20
<212> TYPE: DNA
<213> ORGANISM: artificial
<220> FEATURE:
<223> OTHER INFORMATION: synthetic oligonucleotide primer

<400> SEQUENCE: 80
tgactccccg tcgtgtagat                                               20

<210> SEQ ID NO 81
<211> LENGTH: 20
<212> TYPE: DNA
<213> ORGANISM: artificial
<220> FEATURE:
<223> OTHER INFORMATION: synthetic oligonucleotide primer

<400> SEQUENCE: 81
agacgtcagg tggcactttt                                               20
```

What is claimed is:

1. An isolated nucleotide sequence comprising a cDNA sequence encoding the full length RNA genome of a mumps virus, wherein the cDNA sequence encoding the full length RNA genome of the mumps virus comprises one or more mutations to the V/I/P gene abrogating expression of a V protein product, wherein the mumps virus is an infectious mumps virus, wherein the one or more mutations to the V/I/P gene abrogating expression of the V protein comprise replacing the nucleotide sequence GGGGGG with the nucleotide sequence GAGGAGGG at the editing site in the P/V gene, wherein only a transcript encoding the P protein is generated from the P/V transcript.

2. The isolated nucleotide sequence of claim 1, the cDNA sequence encoding the full length RNA genome of a mumps virus further comprising a deletion of the open reading frame (ORF) encoding the SH protein, a mutation converting a start codon into a stop codon, or a mutation in the region between the ORF encoding the F polypeptide and the ORF encoding the SH polypeptide that disrupts transcription of the SH gene.

3. The isolated nucleotide sequence of claim 1 further comprising a mutation and/or deletion in the cDNA sequence encoding the full length RNA genome of a mumps virus.

4. The isolated nucleotide sequence of claim 3 wherein the mutation or deletion effects phosphorylation of the P protein of the mumps virus.

5. The isolated nucleotide sequence claim 3 comprising a mutation of the L gene of the mumps virus.

6. The isolated nucleotide sequence of claim 1 wherein the nucleotide sequence expresses an I protein product.

7. The isolated nucleotide sequence of claim 1 wherein the mumps virus is MuV/IowaUS/2006 (MuV-IA).

8. A recombinant mumps virus (rMuV) comprising a full-length genome comprising a sequence equivalent to the cDNA sequence of claim 1.

9. A plasmid comprising the isolated nucleotide sequence of claim 1.

10. A method of inducing an immune response to mumps virus in a subject, the method comprising administering an effective amount of an isolated nucleotide sequence of claim 1 to the subject.

11. A method of vaccinating a subject against mumps, the method comprising administering an effective amount of an isolated nucleotide sequence of claim 1 to the subject.

12. The isolated nucleotide sequence comprising the cDNA sequence encoding the full length RNA genome of a mumps virus of claim 1, wherein the mumps virus further encodes a heterologous polypeptide.

13. The isolated nucleotide sequence comprising the cDNA sequence encoding the full length RNA genome of a mumps virus of claim 1 further comprising the deletion of 156 nucleotides of the ORF encoding the SH protein.

14. The isolated nucleotide sequence comprising the cDNA sequence encoding the full length RNA genome of a mumps virus of claim 1 further comprising the addition of four nucleotides to the 3' untranslated region of the transcript encoding the P protein.

15. The isolated nucleotide sequence comprising the cDNA sequence encoding the full length RNA genome of a mumps virus of claim 1, wherein the mumps virus is genotype A or genotype G.

16. A composition comprising an isolated nucleotide acid sequence of claim 1.

17. The isolated nucleotide sequence of claim 7, wherein the cDNA sequence encoding the full length RNA genome of the MuV/IowaUS/2006 (MuV-IA) virus comprises SEQ ID NO:1.

18. An infectious recombinant mumps virus (rMuV) comprising a full-length genome comprising a sequence equivalent to the cDNA sequence of claim 1.

19. A method of inducing an immune response to mumps virus in a subject, the method comprising administering an effective amount of a recombinant mumps virus (rMuV) of claim 18 to the subject.

20. An infectious recombinant mumps virus (rMuV) comprising a full-length genome comprising a sequence equivalent to the cDNA sequence of claim 2.

21. A method of inducing an immune response to mumps virus in a subject, the method comprising administering an effective amount of a recombinant mumps virus (rMuV) of claim 20 to the subject.

22. The isolated nucleotide sequence of claim 3 comprising a mutation encoding amino acid residue 147 and/or amino acid residue 307 of the P protein.

23. A composition comprising an infectious viral particle of claim 18.

24. The composition of claim 23 further comprising a rubella and/or measles antigenic determinant.

* * * * *

UNITED STATES PATENT AND TRADEMARK OFFICE
CERTIFICATE OF CORRECTION

PATENT NO. : 9,649,371 B2  
APPLICATION NO. : 14/001228  
DATED : May 16, 2017  
INVENTOR(S) : Biao He et al.

Page 1 of 1

It is certified that error appears in the above-identified patent and that said Letters Patent is hereby corrected as shown below:

On the Title Page

Item (75) Inventors, please add --Steven A. Rubin, Buckeystown, MD (US)-- as a named inventor.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*